(12) United States Patent
Caplin et al.

(10) Patent No.: US 10,669,574 B2
(45) Date of Patent: Jun. 2, 2020

(54) DNA AMPLIFICATION TECHNOLOGY

(71) Applicant: Fluoresentric, Inc., Park City, UT (US)

(72) Inventors: Brian Caplin, Park City, UT (US); Bryson Green, Heber, UT (US)

(73) Assignee: XCR Diagnostics, Inc., Salt Lake City, UT (US)

( * ) Notice: Subject to any disclaimer, the term of this patent is extended or adjusted under 35 U.S.C. 154(b) by 272 days.

(21) Appl. No.: 15/324,218

(22) PCT Filed: Jul. 10, 2015

(86) PCT No.: PCT/US2015/040035
§ 371 (c)(1),
(2) Date: Jan. 5, 2017

(87) PCT Pub. No.: WO2016/007914
PCT Pub. Date: Jan. 14, 2016

(65) Prior Publication Data
US 2017/0198342 A1    Jul. 13, 2017

Related U.S. Application Data

(60) Provisional application No. 62/023,123, filed on Jul. 10, 2014, provisional application No. 62/075,769, (Continued)

(51) Int. Cl.
*C12Q 1/6853*    (2018.01)
*C12Q 1/6811*    (2018.01)
(Continued)

(52) U.S. Cl.
CPC .......... *C12Q 1/6853* (2013.01); *C12Q 1/686* (2013.01); *C12Q 1/689* (2013.01); *C12Q 1/6811* (2013.01); *C12Q 2600/158* (2013.01)

(58) Field of Classification Search
None
See application file for complete search history.

(56) References Cited

U.S. PATENT DOCUMENTS 4,683,195 A    7/1987    Mullis et al.
4,965,188 A    10/1990    Mullis et al.
(Continued)

FOREIGN PATENT DOCUMENTS

EP    2065465 A2    6/2009
EP    2530466 A1    12/2012
(Continued)

OTHER PUBLICATIONS

Chen et al. Methods in Molecular Biology 2002; 192: 19-29. (Year: 2002).*
(Continued)

*Primary Examiner* — Angela M. Bertagna
(74) *Attorney, Agent, or Firm* — Cooley LLP

(57) ABSTRACT

Methods and reagents suitable for conducing polymerase chain reaction are described. In particular, a nucleic acid amplification design strategy and thermal cycling profile to enable efficient amplification of multiple nucleic acid targets along with improved sensitivity is disclosed. The present disclosure also describes methods and devices for increasing the melting temperature (Tm) of a primer.

24 Claims, 49 Drawing Sheets

Specification includes a Sequence Listing.

Related U.S. Application Data filed on Nov. 5, 2014, provisional application No. 62/115,559, filed on Feb. 12, 2015.

(51) Int. Cl.
*C12Q 1/689* (2018.01)
*C12Q 1/686* (2018.01)

(56) References Cited

U.S. PATENT DOCUMENTS

| | | |
|---|---|---|
| 5,219,727 A | 6/1993 | Wang et al. |
| 5,314,809 A | 5/1994 | Erlich et al. |
| 5,476,774 A | 12/1995 | Wang et al. |
| 5,491,063 A | 2/1996 | Fisher et al. |
| 5,538,848 A | 7/1996 | Livak et al. |
| 5,571,673 A | 11/1996 | Picone |
| 5,573,906 A | 11/1996 | Bannwarth et al. |
| 5,660,988 A | 8/1997 | Duck et al. |
| 5,804,375 A | 9/1998 | Gelfand et al. |
| 6,001,611 A | 12/1999 | Will |
| 6,033,881 A | 3/2000 | Himmler et al. |
| 6,040,166 A | 3/2000 | Erlich et al. |
| 6,197,563 B1 | 3/2001 | Erlich et al. |
| 6,214,587 B1 | 4/2001 | Dattagupta et al. |
| 6,506,568 B2 | 1/2003 | Shriver |
| 6,617,137 B2 | 9/2003 | Dean et al. |
| 6,692,918 B2 | 2/2004 | Kurn |
| 6,740,745 B2 | 5/2004 | Auerbach et al. |
| 6,815,165 B2 | 11/2004 | Lee et al. |
| 6,821,727 B1 | 11/2004 | Livak et al. |
| 6,977,148 B2 | 12/2005 | Dean et al. |
| 7,074,600 B2 | 7/2006 | Dean et al. |
| 7,081,226 B1 | 7/2006 | Wittwer et al. |
| 7,160,998 B2 | 1/2007 | Wittwer et al. |
| 7,838,235 B2 | 11/2010 | Caplin |
| 8,119,352 B2 | 2/2012 | Kozma et al. |
| 8,455,190 B2 | 6/2013 | Makrigiorgos |
| 9,139,882 B2 | 9/2015 | Caplin |
| 9,353,408 B2 | 5/2016 | Caplin |
| 9,670,531 B2 | 6/2017 | Caplin |
| 10,337,056 B2 | 7/2019 | Caplin |
| 10,370,707 B2 | 8/2019 | Caplin |
| 2003/0073147 A1 | 4/2003 | Alderete et al. |
| 2004/0053254 A1 | 3/2004 | Wangh et al. |
| 2004/0058378 A1 | 3/2004 | Kong et al. |
| 2004/0248105 A1 | 12/2004 | Kumar |
| 2004/0259100 A1 | 12/2004 | Gunderson et al. |
| 2005/0181394 A1 | 8/2005 | Steemers et al. |
| 2005/0227257 A1 | 10/2005 | Abravaya et al. |
| 2005/0233363 A1 | 10/2005 | Harding et al. |
| 2005/0244835 A1 | 11/2005 | Chou |
| 2006/0063175 A1 | 3/2006 | Ku et al. |
| 2006/0147955 A1 | 7/2006 | Allawi et al. |
| 2007/0020672 A1 | 1/2007 | Wittwer et al. |
| 2007/0054276 A1 | 3/2007 | Sampson |
| 2007/0054311 A1 | 3/2007 | Kamberov et al. |
| 2007/0219122 A1 | 9/2007 | Glazer et al. |
| 2008/0044812 A1 | 2/2008 | Molly et al. |
| 2008/0070241 A1* | 3/2008 | Rabbani ............... C12Q 1/6844 435/6.12 |
| 2008/0241893 A1 | 10/2008 | Weisburg et al. |
| 2008/0305478 A1* | 12/2008 | Chun ................... C12Q 1/6848 435/6.11 |
| 2009/0011408 A1 | 1/2009 | Sorge et al. |
| 2009/0068641 A1 | 3/2009 | Bergeron et al. |
| 2009/0075269 A1* | 3/2009 | Caplin ................ C12Q 1/6827 435/6.18 |
| 2009/0226881 A1 | 9/2009 | Godfrey et al. |
| 2009/0325156 A1 | 12/2009 | Figg et al. |
| 2011/0097764 A1 | 4/2011 | Johnson et al. |
| 2011/0143357 A1 | 6/2011 | Caplin |
| 2012/0315642 A1* | 12/2012 | Kankia ................ C12Q 1/6816 435/6.12 |
| 2014/0274756 A1 | 9/2014 | Nguyen et al. |
| 2014/0329702 A1* | 11/2014 | Vats .................... C12Q 1/6853 506/9 |
| 2015/0099659 A1 | 4/2015 | Caplin |
| 2015/0376689 A1 | 12/2015 | Caplin |
| 2016/0230218 A1 | 8/2016 | Caplin |
| 2017/0226576 A1 | 8/2017 | Caplin |
| 2019/0271036 A1 | 9/2019 | Caplin |

FOREIGN PATENT DOCUMENTS

| | | |
|---|---|---|
| RU | 2186112 C2 | 7/2002 |
| RU | 2251552 C2 | 5/2005 |
| RU | 2427648 C1 | 8/2011 |
| RU | 2451086 C1 | 5/2012 |
| WO | WO 1998/045474 A1 | 10/1998 |
| WO | WO 2000/043545 A2 | 7/2000 |
| WO | WO 2006/074334 A2 | 7/2006 |
| WO | WO 2008/119081 A1 | 10/2008 |
| WO | WO 2010/013017 A1 | 2/2010 |
| WO | WO 2011/030145 A1 | 3/2011 |
| WO | WO 2011/053987 A1 | 5/2011 |
| WO | WO 2012/095639 A2 | 7/2012 |
| WO | WO 2012/096430 A1 | 7/2012 |
| WO | WO 2012/145725 A2 | 10/2012 |
| WO | WO 2013/113748 A1 | 8/2013 |
| WO | WO 2015/054516 A2 | 4/2015 |
| WO | WO 2016/007914 A1 | 1/2016 |

OTHER PUBLICATIONS

Eritja et al. Nucleic Acids Research 1986; 14: 5869-5884. (Year: 1986).*
Extended European Search Report for Application No. EP 15818265.9 dated May 23, 2018, 15 pages.
HIV-1 Sequence (K02007.1) in Genebank downloaded Apr. 29, 2018 (Year: 1985), 6 pages.
Holland, et al., "Detection of specific polymerase chain reaction product by utilizing the 5'→3' exonuclease activity of Thermus aquaticus DNA polymerase." PNAS (1991); 88 (16): 7276-7280.
Lyamichev, et al., "Polymorphism identification and quantitative detection of genomic DNA by invasive cleavage of oligonucleotide probes." Nature Biotechnology (1999); 17: 292-296.
Rudert, et al., "Double-Labeled Fluorescent Probes for 5' Nuclease Assays: Purification and Performance Evaluation." Biotechniques (1997); 22 (6): 1140-1145.
Sanchez-Pescador, et al., "Nucleotide sequence and expression of an AIDS-associated retrovirus (ARV-2)." Science (1985); 227 (4686): 484-492.
Written Opinion in PCT/US2014/059935 dated Mar. 20, 2015, 7 pages.
Anonymous: "Performing Fast PCR Using Bio-Rad Thermal Cyclers", Jan. 1, 2005 (Jan. 1, 2005), XP55402836, Retrieved from the Internet: URL:http://www.bio-rad.com/LifeScience/jobs/2005/05-0739/fast_pcr.pdf [retrieved on Aug. 31, 2017], 21 pages.
Sullivan, D., et al., "Fast PCR: General Considerations for Minimizing Run Times and Maximizing Throughput." Mar. 7, 2007 (Mar. 7, 2007), XP55402819, Retrieved from the Internet: URL:http://www.bio-rad.com/webroot/web/pdf/lsr/literature/Bulletin_5362.pdf [retrieved on Aug. 31, 2017], 6 pages.
Bannwarth et al., "219. Bathophenanthroline-ruthenium(II) Complexes as Non-Radioactive Labels for Oligonucleotides which Can Be Measured by Time-Resolved Fluorescence Techniques," Helv. Chim. Acta 71: 2085-2099 (1988).
Database Online GenBank CT737339.6 Jul. 27, 2006 [downloaded Feb. 8, 2018], 30 pages.
Definition of Minimum Performance Requirements for Analytical Methods of GMO Testing, European Network of GMO Laboratories, Oct. 2008.
International Preliminary Report on Patentability for International Application No. PCT/US2014/059935 dated Apr. 12, 2016, 8 pages.
International Search Report in PCT/US2014/059935 dated Mar. 20, 2015 (5 pages).
Partial Supplementary European Search Report for Application No. EP 15818265.9 dated Feb. 7, 2018, 16 pages.

(56) References Cited

OTHER PUBLICATIONS

Rychlik et al., A computer program for choosing optimal oligonucleotides for filter hybridization, sequencing and in vitro amplification of DNA, Nucleic Acids Res., 1989, 17:8543-8551.
Sambrook, et al., Molecular cloning—A Laboratory Manual, 1985, Cold Springs Harbor, N.Y., pp. 8.9-8-10.
Supplementary European Search Report, EP Appl. No. 14852079.4, 8 pages (dated May 23, 2017).
Allawi, Hatim T., and Santalucia, Jr., John. "Thermodynamics and NMR of Internal G♦T Mismatches in DNA." Biochemistry (1997); 36.34: 10581-10594.
Arya et al. "Basic principles of real-time quantitative PCR," Expert Review of Molecular Diagnostics (2005); vol. 5, No. 2, pp. 209-219.
Auer, Tatiana et al., "Selective amplification of RNA utilizing the nucleotide analog dITP and Thermus thermophilus DNA polymerase", Nucleic Acids Research, 1996, pp. 5021-5025, vol. 24, No. 24.
Breslauer, K.J., et al., "Predicting DNA duplex stability from the base sequence." PNAS (1986); vol. 83, No. 11, pp. 3746-3750.
Bustin, Stephen A., et al. "The MIQE Guidelines: Minimum Information for Publication of Quantitative Real-Time PCR Experiments." Clinical Chemistry (2009); 55.4: 611-622.
Carr, J.F. et al., "Severity of the Streptomycin Resistance and Streptomycin Dependence Phenotypes of Ribosomal Protein S12 of Thermus Thermophilus Depends on the Identity of Highly Conserved Amino Acid Residues," Journal of Bacteriology, May 2005, pp. 3548-3550, vol. 187, No. 10.
Chinese First Office Action, Chinese Application No. 200880018252.X, dated May 31, 2012, 13 pages.
Chinese Second Office Action, Chinese Application No. 200880018252.X, dated Mar. 4, 2013, 13 pages.
Chinese Third Office Action, Chinese Application No. 200880018252.X, dated Nov. 12, 2013, 10 pages.
Edwards, K.J. et al., "Detection of rpoB Mutations in *Mycobacterium tuberculosis* by Biprobe Analysis," Journal of Clinical Microbiology, Sep. 2001, pp. 3350-3352, vol. 39, No. 9.
Definition of Minimum Performance Requirements for Analytical Methods of GMO Testing, European Network of GMO Laboratories, Oct. 2008, 8 pages.
European Supplementary Search Report, European Application No. 08744694.4, dated Jul. 26, 2010, 14 pages.
European Examination Report, European Application No. 08744694.4, dated Apr. 7, 2011, 4 pages.
European Examination Report, European Application No. 12187764.1, dated Mar. 24, 2014, 4 pages.
European Extended Search Report, European Application No. 12187764.1, dated Mar. 1, 2013, 7 pages.
Extended European Search Report in Application No. 16161557.0, dated Oct. 10, 2016, 6 pages.
Giannakakou, P. et al., "A Common Pharmacophore for Epothilone and Taxanes: Molecular Basis for Drug Resistance Conferred by Tubulin Mutations in Human Cancer Cells," PNAS, Mar. 14, 2000, pp. 2904-2909, vol. 97, No. 6.
Gilbert et al., "Resistance of herpesviruses to antiviral drugs: clinical impacts and molecular mechanisms," Drug Resistance Updates, 2002, vol. 5, pp. 88-114.
Hazbon, M.H. et al., "Population Genetics Study of Isoniazid Resistance Mutations and Evolution of Multidrug-Resistant *Mycobacterium tuberculosis*," Antimicrobial Agents and Chemotherapy, Aug. 2006, pp. 2640-2649, vol. 50, No. 8.
Hymas et al., "Use of lyophilized standards for the calibration of a newly developed real time PCR assay for human herpes type six (HHV6) variants A and B," J. Virol. Meth., 2005, vol. 128, pp. 143-150.
Indian Office Action, Indian Application No. 6340/CHENP/2009, dated Mar. 20, 2013, 2 pages.
International Preliminary Report on Patentability for International Application No. PCT/US2008/058786, dated Sep. 29, 2009, 6 pages.
International Search Report and Written Opinion for International Application No. PCT/US2008/058786, dated Aug. 29, 2008, 8 pages.
International Search Report and Written Opinion for International Application No. PCT/US2015/040035, dated Oct. 30, 2015, 18 pages.
International Preliminary Report on Patentability for International Application No. PCT/US2015/040035, dated Jan. 10, 2017, 16 pages.
Lavender, C. et al., "Molecular Characterization of Isoniazid-Resistant *Mycobacterium tuberculosis* Isolates Collected in Australia," Antimicrobial Agents and Chemotherapy, Oct. 2005, pp. 4068-4074, vol. 49, No. 10.
Leber, R. et al., "Molecular Mechanism of Terbinafine Resistance in *Saccharomyces cerevisiae*," Antimicrobial Agents and Chemotherapy, Dec. 2003, pp. 3890-3900, vol. 47, No. 12.
Li, Cheuk M., et al. "Association of a polymorphism in the P2X7 gene with tuberculosis in a Gambian population." Journal of Infectious Diseases (2002); 186.10: 1458-1462.
Lowe, Todd, et al. "A computer program for selection of oligonucleotide primers for polymerase chain reactions." Nucleic Acids Research (1990); 18.7: 1757-1761.
Masny, A. et al., "Ligation Mediated PCR Performed at Low Denaturation Temperatures—PCT Melting Profiles," Nucleic Acids Research, Sep. 15, 2003, pp. 1-6, vol. 31, No. 18.
Maus, C.E. et al., "Molecular Analysis of Cross-Resistance to Capreomycin, Kanamycin, Amikacin, and Viomycin in *Mycobacterium tuberculosis*," Antimicrobial Agents and Chemotherapy, Aug. 2005, pp. 3192-3197, vol. 49, No. 8.
Mayor, A. G. et al., "Prevalence of the K76T Mutation in the Putative Plasmodium falciparum Chloroquine Resistance Transporter (pfcrt) Gene and Its Relation to Chloroquine Resistance in Mozambique," The Journal of Infectious Diseases, 2001, pp. 1413-1416, vol. 183.
McCammon, M.T. et al., "Detection of rpoB Mutations Associated with Rifampin Resistance in *Mycobacterium tuberculosis* Using Denaturing Gradient Gel Electrophoresis," Antimicrobial Agents and Chemotherapy, Jun. 2005, pp. 2200-2209, vol. 49, No. 6.
Meier, A. et al., "Genetic Alterations in Streptomycin-Resistant *Mycobacterium tuberculosis*: Mapping of Mutations Conferring Resistance," Antimicrobial Agents and Chemotherapy, Feb. 1994, pp. 228-233, vol. 38, No. 2.
Mwangi, M.M. et al., "Tracking the In Vivo Evolution of Multidrug Resistance in *Staphylococcus aureus* by Whole-Genome Sequencing," PNAS, May 29, 2007, pp. 9451-9456, vol. 104, No. 22.
Neo, Jia Ling, and Uttamchandani, Mahesh. "Visual DNA Detection and SNP Genotyping Using Asymmetric PCR and Split DNA Enzymes." Nucleic Acid Detection: Methods and Protocols (2013): 141-151.
Notomi, T. et al., "Loop-Mediated Isothermal Amplification of DNA," Nucleic Acids Research, Jan. 2000, pp. 1-7, vol. 28, No. 12.
Ramaswamy, S.V. et al., "Molecular Genetic Analysis of Nucleotide Polymorphims Associated with Ethambutol Resistance in Human Isolates of *Mycobacterium tuberculosis*," Antimicrobial Agents and Chemotherapy, Feb. 2000, pp. 326-336, vol. 44, No. 2.
Ramaswamy, S.V. et al., "Single Nucleotide Polymorphisms in Genes Associated with Isoniazid Resistance in *Mycobacterium tuberculosis*," Antimicrobial Agents and Chemotherapy, Apr. 2003, pp. 1241-1250, vol. 47, No. 4.
Rychlik, Wojciech, and Rhoads, Robert E. "A computer program for choosing optimal oligonudeotides for filter hybridization, sequencing and in vitro amplification of DNA." Nucleic Acids Research (1989); 17.21: 8543-8551.
Santalucia, Jr., John. "A unified view of polymer, dumbbell, and oligonucleotide DNA nearest-neighbor thermodynamics." Proceedings of the National Academy of Sciences (1998); 95.4: 1460-1465.
Somoskovi, A. et al., "Sequencing of the pncA Gene in Members of the *Mycobacterium tuberculosis* Complex Has Important Diagnostic Applications: Identification of a Species-Specific pncA Mutation in "*Mycobacterium canetti*!" and the Reliable and Rapid Predictor of Pyrazinamide Resistance," Journal of Clinical Microbiology, Feb. 2007, pp. 595-599, vol. 45, No. 2.

(56) References Cited

OTHER PUBLICATIONS

Springer, B. et al., "Mechanisms of Streptomycin Resistance: Selection of Mutations in the 16S rRNA Gene Conferring Resistance," Antimicrobial Agents and Chemotherapy, Oct. 2001, pp. 2877-2884, vol. 45, No. 10.

Sreevatsan, S. et al., "Analysis of the oxyR-ahpC Region in Isoniazid-Resistant and -Susceptible *Mycobacterium tuberculosis* Complex Organisms Recovered from Diseased Humans and Animals in Diverse Localities," Antimicrobial Agents and Chemotherapy, Mar. 1997, pp. 600-606, vol. 41, No. 3.

Sun, Z. et al., "The pncA Gene from Naturally Pyrazinamide-Resistant *Mycobacterium avium* Encodes Pyrazinamidase and Confers Pyrazinamide Susceptibility to Resistant M. Tuberculosis Complex Organisms," Microbiology, 1997, pp. 3367-3373, vol. 143.

Telenti, A., et al. "Genotypic assessment of isoniazid and rifampin resistance in *Mycobacterium tuberculosis*: a blind study at reference laboratory level." Journal of Clinical Microbiology (1997); 35.3: 719-723.

Torres, M.J. et al., "Improved Real-Time PCR for Rapid Detection of Rifampin and Isoniazid Resistance in *Mycobacterium tuberculosis* Clinical Isolates," Diagnostic Microbiology and Infectious Diseases, Mar. 2003, pp. 207-212, vol. 45, No. 3.

Tracevska, T. et al., "Spectrum of pncA Mutations in Multidrug-Resistant *Mycobacterium tuberculosis* Isolates Obtained in Latvia," Antimicrobial Agents and Chemotherapy, Aug. 2004, pp. 3209-3210, vol. 48, No. 8.

Van Doorn, H.R. et al., "Detection of a Point Mutation Associated with High-Level Isoniazid Resistance in *Mycobacterium tuberculosis* by Using Real-Time PCR Technology with 3'-Minor Groove Binder-DNA Probes," Journal of Clinical Microbiology, Oct. 2003, pp. 4630-4635, vol. 41, No. 10.

Williams, D.L. et al., "Characterization of Rifampin Resistance in Pathogenic *Mycobacteria*," Antimicrobial Agents and Chemotherapy, Oct. 1994, pp. 2380-2386, vol. 38, No. 10.

Yap, S-H. et al., "N3481 in the Connection of Domain of HIV-1 Reverse Transcriptase Confers Zikovudine and Nevirapine Resistance," PLOS Medicine, Dec. 2007, pp. 1887-1900, vol. 4, Issue 12, [Online] [Retrieved on Aug. 9, 2011] Retrieved from the Internet<URL:www.plosmedicine.org>.

Yue, J. et al., "Mutations in the rpoB Gene of Multidrug-Resistant *Mycobacterium tuberculosis* Isolates from China," Journal of Clinical Microbiology, May 2003, pp. 2209-2212, vol. 41, No. 5.

Boniotto, et al., "Novel Hairpin-Shaped Primer Assay to Study the Association of the -44 Single-Nucleotide Polymorphism of the DEFB1 Gene with Early-Onset Periodontal Disease". Clinical and Diagnostic Laboratory Immunology (Jul. 2004); 11(4): 766-769.

Zhou, et al., "Enrichment and Detection of Rare Alleles by Means of Snapback Primers and Rapid-Cycle PCR", Clinical Chemistry (Mar. 2010); 56(5): 814-822.

\* cited by examiner

Quenched

Quenched

Ex494 Em650

```
                              SEQUENCE LISTING

<160> NUMBER OF SEQ ID NOS: 59

<210> SEQ ID NO 1
    <211> LENGTH: 72
    <212> TYPE: DNA
    <213> ORGANISM: artificial
    <220> FEATURE:
    <223> OTHER INFORMATION: Folded hairpin-like probe example

<400> SEQUENCE: 1
acctccaatg ccaaacatta ctccttgact caatgtttcc tgtgccagca tgcgcttatt      60
agacccatgg cc                                                          72

<210> SEQ ID NO 2
    <211> LENGTH: 67
    <212> TYPE: DNA
    <213> ORGANISM: artificial
    <220> FEATURE:
    <223> OTHER INFORMATION: Folded hairpin-like probe example

<400> SEQUENCE: 2
agcactcagt tattctgctg gtgcacttgc cagttgcatg ggcctcatat acaacaggat      60
gggggct                                                               67

<210> SEQ ID NO 3
    <211> LENGTH: 83
    <212> TYPE: DNA
    <213> ORGANISM: artificial
    <220> FEATURE:
    <223> OTHER INFORMATION: Folded hairpin-like probe example

<400> SEQUENCE: 3
atggacgtgg cttagcgtat atttatgctg atggaaaaat ggtaaacgaa gctttagttc      60
gtcaaggctt ggctaaagtt gct                                             83

<210> SEQ ID NO 4
    <211> LENGTH: 83
    <212> TYPE: DNA
    <213> ORGANISM: artificial
    <220> FEATURE:
    <223> OTHER INFORMATION: Folded hairpin-like probe example

<400> SEQUENCE: 4
atggacgtgg cttagcgtat atttatgctg atggaaaaat ggtaaacgaa gctttagttc      60
gtcaaggctt ggctaaagtt gct                                             83
```

<210> SEQ ID NO 5
<211> LENGTH: 67
<212> TYPE: DNA
<213> ORGANISM: artificial
<220> FEATURE:
<223> OTHER INFORMATION: Folded hairpin-like probe example

<400> SEQUENCE: 5
agcactcagt tattctgctg gtgcacttgc cagttgcatg ggcctcatat acaacaggat    60
gggggct                                                              67

<210> SEQ ID NO 6
<211> LENGTH: 38
<212> TYPE: DNA
<213> ORGANISM: artificial
<220> FEATURE:
<223> OTHER INFORMATION: Folded hairpin-like probe example

<400> SEQUENCE: 6
tggcaatccc aggttttctt ttctacctgt ttgctcaa                            38

<210> SEQ ID NO 7
<211> LENGTH: 36
<212> TYPE: DNA
<213> ORGANISM: artificial
<220> FEATURE:
<223> OTHER INFORMATION: Folded hairpin-like probe example

<400> SEQUENCE: 7
cagacccatc ccccaggtga gggactatgg cctcct                              36

<210> SEQ ID NO 8
<211> LENGTH: 30
<212> TYPE: DNA
<213> ORGANISM: artificial
<220> FEATURE:
<223> OTHER INFORMATION: Folded hairpin-like probe example

<400> SEQUENCE: 8
tcaatggctg aggtgaggta ccccgcaggg                                     30

<210> SEQ ID NO 9
<211> LENGTH: 42
<212> TYPE: DNA
<213> ORGANISM: artificial
<220> FEATURE:
<223> OTHER INFORMATION: Folded hairpin-like probe example

<400> SEQUENCE: 9
tttgctctga gagttccccc tgtcccctcc accttccctc ag                       42

<210> SEQ ID NO 10
<211> LENGTH: 45
<212> TYPE: DNA
<213> ORGANISM: artificial
<220> FEATURE:
<223> OTHER INFORMATION: Folded hairpin-like probe example

<400> SEQUENCE: 10
tgcaagagtc accaaaattg ccgagaggcc ccagttagca tccca                    45

<210> SEQ ID NO 11
<211> LENGTH: 47
<212> TYPE: DNA
<213> ORGANISM: artificial

```
<220> FEATURE:
<223> OTHER INFORMATION: Made in lab

<400> SEQUENCE: 11
gatcgatgct agctatggcc cctcagagcc ggctctgagg ggccata                47

<210> SEQ ID NO 12
<211> LENGTH: 36
<212> TYPE: DNA
<213> ORGANISM: artificial
<220> FEATURE:
<223> OTHER INFORMATION: Salmonella forward primer without tag

<400> SEQUENCE: 12
cgacgaccct tcttttttcct caatactgag cggctg                           36

<210> SEQ ID NO 13
<211> LENGTH: 60
<212> TYPE: DNA
<213> ORGANISM: artificial
<220> FEATURE:
<223> OTHER INFORMATION: Salmonella reverse primer without tag

<400> SEQUENCE: 13
cgctgccggt atttgttatt ttatcggtgg ttttaagcgt actcttctat tttaaattcc  60

<210> SEQ ID NO 14
<211> LENGTH: 41
<212> TYPE: DNA
<213> ORGANISM: artificial
<220> FEATURE:
<223> OTHER INFORMATION: Salmonella forward primer with tag

<400> SEQUENCE: 14
cgtcgcgacg acccttcttt ttcctcaata ctgagcggct g                      41

<210> SEQ ID NO 15
<211> LENGTH: 65
<212> TYPE: DNA
<213> ORGANISM: artificial
<220> FEATURE:
<223> OTHER INFORMATION: Salmonella reverse primer with tag

<400> SEQUENCE: 15
cagcgcgctg ccggtatttg ttattttatc ggtggtttta agcgtactct tctattttaa  60
attcc                                                              65

<210> SEQ ID NO 16
<211> LENGTH: 143
<212> TYPE: DNA
<213> ORGANISM: artificial
<220> FEATURE:
<223> OTHER INFORMATION: target sequence for first primer binding

<400> SEQUENCE: 16
cgacgaccct tcttttttcct caatactgag cggctgctcg cctttgctgg ttttaggttt  60
ggcggcgcta cgttttgctt cacggaattt aaaatagaag agtacgctta aaaccaccga  120
taaaataaca aataccggca gcg                                          143

<210> SEQ ID NO 17
<211> LENGTH: 31
<212> TYPE: DNA
<213> ORGANISM: artificial
<220> FEATURE:
```

<223> OTHER INFORMATION: shorter Salmonella forward primer without tag

<400> SEQUENCE: 17 accettctttt tcctcaata ctgagcggct g                               31

<210> SEQ ID NO 18
<211> LENGTH: 55
<212> TYPE: DNA
<213> ORGANISM: artificial
<220> FEATURE:
<223> OTHER INFORMATION: shorter Salmonella reverse primer without tag

<400> SEQUENCE: 18
ccggtatttg ttattttatc ggtggtttta agcgtactct tctattttaa attcc     55

<210> SEQ ID NO 19
<211> LENGTH: 133
<212> TYPE: DNA
<213> ORGANISM: artificial
<220> FEATURE:
<223> OTHER INFORMATION: target for second primer binding

<400> SEQUENCE: 19
acccttcttt ttcctcaata ctgagcggct gctcgccttt gctggtttta ggtttggcgg   60
cgctacgttt tgcttcacgg aatttaaaat agaagagtac gcttaaaacc accgataaaa  120
taacaaatac cgg                                                    133

<210> SEQ ID NO 20
<211> LENGTH: 153
<212> TYPE: DNA
<213> ORGANISM: artificial
<220> FEATURE:
<223> OTHER INFORMATION: target for complete primer with tag binding

<400> SEQUENCE: 20
cgtcgcgacg acccttcttt ttcctcaata ctgagcggct gctcgccttt gctggtttta   60
ggtttggcgg cgctacgttt tgcttcacgg aatttaaaat agaagagtac gcttaaaacc  120
accgataaaa taacaaatac cggcagcgcg ctg                              153

<210> SEQ ID NO 21
<211> LENGTH: 180
<212> TYPE: DNA
<213> ORGANISM: Mycobacterium avium subsp. paratuberculosis str. k10

<400> SEQUENCE: 21
tcgaatccct ctccccgccc gggcggtacg acgcgccgag gaagcggtgc accagggcgc   60
gctcggcggc cgggtccttg agcggccagc cccataacgc caggaagacg cggatcagcc  120
actgcgccgc cagcgggtcg tcgtggccgg gcccgagcat ctcggcggcc agggccgtca  180

<210> SEQ ID NO 22
<211> LENGTH: 33
<212> TYPE: DNA
<213> ORGANISM: artificial
<220> FEATURE:
<223> OTHER INFORMATION: forward primer to amplify M. avium target

<400> SEQUENCE: 22
taccgcccgg gcccgggcgg tacgacgcgc cga                              33

<210> SEQ ID NO 23
<211> LENGTH: 33

<212> TYPE: DNA
<213> ORGANISM: artificial
<220> FEATURE:
<223> OTHER INFORMATION: reverse primer to amplify M. avium target

<400> SEQUENCE: 23
ggccgggccc gggcccggcc acgacgaccc gct 33

<210> SEQ ID NO 24
<211> LENGTH: 35
<212> TYPE: DNA
<213> ORGANISM: artificial
<220> FEATURE:
<223> OTHER INFORMATION: Mfo1275fmut2 primer

<400> SEQUENCE: 24
cgtgcacacc cggccaaggt cgttgcggcc cagag 35

<210> SEQ ID NO 25
<211> LENGTH: 45
<212> TYPE: DNA
<213> ORGANISM: artificial
<220> FEATURE:
<223> OTHER INFORMATION: Mfo1490rmut2 primer

<400> SEQUENCE: 25
acggcgtttt cgattgtcgg atccaccccg gaggccctgc tcacc 45

<210> SEQ ID NO 26
<211> LENGTH: 120
<212> TYPE: DNA
<213> ORGANISM: artificial
<220> FEATURE:
<223> OTHER INFORMATION: M. fortuitum synthetic template

<400> SEQUENCE: 26
cgtgcacacc cggccgaggt cgttgcggcc gagatcgact cggtcgcccc gcgccagcga 60
gtgcccgcga tcgacggtga ccagggcctc cgggctggat ccgacaatcg aaaacgccgt 120

<210> SEQ ID NO 27
<211> LENGTH: 29
<212> TYPE: DNA
<213> ORGANISM: artificial
<220> FEATURE:
<223> OTHER INFORMATION: SPWXMF_mut4 primer

<400> SEQUENCE: 27
ccagccaccc accaattcct gtgccagat 29

<210> SEQ ID NO 28
<211> LENGTH: 33
<212> TYPE: DNA
<213> ORGANISM: artificial
<220> FEATURE:
<223> OTHER INFORMATION: SPWXMR_mut4 primer

<400> SEQUENCE: 28
accggaggtc acttttgatg gccatgggtc tat 33

<210> SEQ ID NO 29
<211> LENGTH: 178
<212> TYPE: DNA
<213> ORGANISM: artificial
<220> FEATURE:
<223> OTHER INFORMATION: template for SPWXM primers

<400> SEQUENCE: 29
ctcgttagag gggctaaagc taacccacca attcctgtgc cagagaatat ataggcggt    60 gcatgaacaa tagccggtag gtatgtcaga aaacctccaa tgccaaacat tactccttga   120
caccgcctat atttagaccc atggccatca aaagtgaccc gagcaccatc gtttgttg    178

<210> SEQ ID NO 30
<211> LENGTH: 390
<212> TYPE: DNA
<213> ORGANISM: Xenorhabdus nematophila

<400> SEQUENCE: 30
tttatttttt agttatcaat atatctgagt tttattttt agctacagtg tttttatttg    60 ttttttagc agccttactt aacagtattt tgttaatatc aacatatata agatatatta   120
ttatttcttt actatgctca ataactctat ctttacattt agatatatta ccatcatttg   180
atttaatatt tttcttgcct atatttattt ttgttttat ctataaattt aatctcgtca    240
aaaaaagact ataattatat tgattaattt aagttttcag atgatataat caaattttat   300
tccaataata ccaatcatca ctgaaattgc ttaatttata ctgaagattt ggttatgtat   360
taaatagtta attcttatca tatactccct                                   390

<210> SEQ ID NO 31
<211> LENGTH: 109
<212> TYPE: DNA
<213> ORGANISM: artificial
<220> FEATURE:
<223> OTHER INFORMATION: exemplary forward primer for X. nematophila
       target

<400> SEQUENCE: 31 ttttagtta tcaatatatc tgagttttat ttttagcta cagtgttttt atttgttttt    60
ttagcagcct tacttaacag tattttgtta atatcaacat atataagat              109

<210> SEQ ID NO 32
<211> LENGTH: 31
<212> TYPE: DNA
<213> ORGANISM: artificial
<220> FEATURE:
<223> OTHER INFORMATION: Triplex forming region sequence
<220> FEATURE:
<221> NAME/KEY: misc_feature
<222> LOCATION: (18)..(18)
<220> FEATURE:
<221> NAME/KEY: misc_feature
<222> LOCATION: (18)..(18)
<223> OTHER INFORMATION: n is a, c, g, or t

<400> SEQUENCE: 32
gtgtgggaag aggggganga gggggaggag c                                 31

<210> SEQ ID NO 33
<211> LENGTH: 30
<212> TYPE: DNA
<213> ORGANISM: artificial
<220> FEATURE:
<223> OTHER INFORMATION: Triplex forming region sequence
<220> FEATURE:
<221> NAME/KEY: misc_feature
<222> LOCATION: (14)..(14)
<220> FEATURE:
<221> NAME/KEY: misc_feature
<222> LOCATION: (14)..(14)
<223> OTHER INFORMATION: n is a, c, g, or t

```
<400> SEQUENCE: 33
gctgcctccc ctcntccctc ttccccacac                                    30

<210> SEQ ID NO 34
<211> LENGTH: 31
<212> TYPE: DNA
<213> ORGANISM: artificial
<220> FEATURE:
<223> OTHER INFORMATION: Triplex forming region sequence
<220> FEATURE:
<221> NAME/KEY: misc_feature
<222> LOCATION: (18)..(18)
<220> FEATURE:
<221> NAME/KEY: misc_feature
<222> LOCATION: (18)..(18)
<223> OTHER INFORMATION: n is a, c, g, or t

<400> SEQUENCE: 34
gtgtgggaag aggggganga gggggaggag c                                  31

<210> SEQ ID NO 35
<211> LENGTH: 30
<212> TYPE: DNA
<213> ORGANISM: artificial
<220> FEATURE:
<223> OTHER INFORMATION: Triplex forming region sequence
<220> FEATURE:
<221> NAME/KEY: misc_feature
<222> LOCATION: (14)..(14)
<220> FEATURE:
<221> NAME/KEY: misc_feature
<222> LOCATION: (14)..(14)
<223> OTHER INFORMATION: n is a, c, g, or t

<400> SEQUENCE: 35
gctgcctccc ctcntccctc ttccccacac                                    30

<210> SEQ ID NO 36
<211> LENGTH: 22
<212> TYPE: DNA
<213> ORGANISM: artificial
<220> FEATURE:
<223> OTHER INFORMATION: Triplex forming sequence

<400> SEQUENCE: 36 ggaggggag aagggagaag gg                                             22

<210> SEQ ID NO 37
<211> LENGTH: 22
<212> TYPE: DNA
<213> ORGANISM: artificial
<220> FEATURE:
<223> OTHER INFORMATION: Triplex forming sequence

<400> SEQUENCE: 37
cccttctccc ttctccccct cc                                            22

<210> SEQ ID NO 38
<211> LENGTH: 22
<212> TYPE: DNA
<213> ORGANISM: artificial
<220> FEATURE:
<223> OTHER INFORMATION: Triplex forming sequence

<400> SEQUENCE: 38
ggtgggggtg ttgggtgttg gg                                            22
```

```
<210> SEQ ID NO 39
<211> LENGTH: 22
<212> TYPE: DNA
<213> ORGANISM: artificial
<220> FEATURE:
<223> OTHER INFORMATION: Triplex forming sequence

<400> SEQUENCE: 39
ggtgggggtg ttgggtgttg gg                                              22

<210> SEQ ID NO 40
<211> LENGTH: 31
<212> TYPE: DNA
<213> ORGANISM: artificial
<220> FEATURE:
<223> OTHER INFORMATION: Triplex forming sequence
<220> FEATURE:
<221> NAME/KEY: misc_feature
<222> LOCATION: (18)..(18)
<220> FEATURE:
<221> NAME/KEY: misc_feature
<222> LOCATION: (18)..(18)
<223> OTHER INFORMATION: n is a, c, g, or t

<400> SEQUENCE: 40
gtgtgggaag aggggganga gggggaggag c                                    31

<210> SEQ ID NO 41
<211> LENGTH: 30
<212> TYPE: DNA
<213> ORGANISM: artificial
<220> FEATURE:
<223> OTHER INFORMATION: Triplex forming sequence
<220> FEATURE:
<221> NAME/KEY: misc_feature
<222> LOCATION: (14)..(14)
<220> FEATURE:
<221> NAME/KEY: misc_feature
<222> LOCATION: (14)..(14)
<223> OTHER INFORMATION: n is a, c, g, or t

<400> SEQUENCE: 41
gctgcctccc ctcntccctc ttccccacac                                      30

<210> SEQ ID NO 42
<211> LENGTH: 13
<212> TYPE: DNA
<213> ORGANISM: unknown
<220> FEATURE:
<223> OTHER INFORMATION: Naturally occurring TFR sequence in double
      stranded DNA

<400> SEQUENCE: 42 tttttctcccg tcc                                                       13

<210> SEQ ID NO 43
<211> LENGTH: 12
<212> TYPE: DNA
<213> ORGANISM: unknown
<220> FEATURE:
<223> OTHER INFORMATION: Naturally occurring TFR sequence in double
      stranded DNA

<400> SEQUENCE: 43
ggacgggaaa aa                                                         12

<210> SEQ ID NO 44
<211> LENGTH: 17
<212> TYPE: DNA
```

```
<213> ORGANISM: Spirometra erinaceieuropaei

<400> SEQUENCE: 44 ggcgagggggg gagcggg                                                17

<210> SEQ ID NO 45
<211> LENGTH: 17
<212> TYPE: DNA
<213> ORGANISM: Toxocara canis

<400> SEQUENCE: 45
cccgctcccc cctcgcc                                                 17

<210> SEQ ID NO 46
<211> LENGTH: 13
<212> TYPE: DNA
<213> ORGANISM: unknown
<220> FEATURE:
<223> OTHER INFORMATION: Naturally occurring TFR sequence in double
      stranded DNA

<400> SEQUENCE: 46
ggaggtgggg gag                                                     13

<210> SEQ ID NO 47
<211> LENGTH: 13
<212> TYPE: DNA
<213> ORGANISM: unknown
<220> FEATURE:
<223> OTHER INFORMATION: Naturally occurring TFR sequence in double
      stranded DNA

<400> SEQUENCE: 47
ctcccccacc tcc                                                     13

<210> SEQ ID NO 48
<211> LENGTH: 13
<212> TYPE: DNA
<213> ORGANISM: unknown
<220> FEATURE:
<223> OTHER INFORMATION: Naturally occurring TFR sequence in double
      stranded DNA

<400> SEQUENCE: 48
ggaggtgggg gag                                                     13

<210> SEQ ID NO 49
<211> LENGTH: 14
<212> TYPE: DNA
<213> ORGANISM: unknown
<220> FEATURE:
<223> OTHER INFORMATION: Naturally occurring TFR sequence in double
      stranded DNA

<400> SEQUENCE: 49 ctcccccac ctcc                                                     14

<210> SEQ ID NO 50
<211> LENGTH: 30
<212> TYPE: DNA
<213> ORGANISM: Streptococcus dysgalactiae

<400> SEQUENCE: 50
ggagaaggtg aggaagaaga agaggaagaa                                   30
```

```
<210> SEQ ID NO 51
<211> LENGTH: 38
<212> TYPE: DNA
<213> ORGANISM: artificial
<220> FEATURE:
<223> OTHER INFORMATION: exemplary forward primer for X. nematophila
      target

<400> SEQUENCE: 51
tttttagtta tcaatatatc tgagttttat tttttagc                               38

<210> SEQ ID NO 52
<211> LENGTH: 38
<212> TYPE: DNA
<213> ORGANISM: artificial
<220> FEATURE:
<223> OTHER INFORMATION: exemplary reverse primer for X. nematophila
      target

<400> SEQUENCE: 52
atcttatata tgttgatatt aacaaaatac tgttaagt                               38

<210> SEQ ID NO 53
<211> LENGTH: 30
<212> TYPE: DNA
<213> ORGANISM: artificial
<220> FEATURE:
<223> OTHER INFORMATION: exemplary probe for X. nematophila target

<400> SEQUENCE: 53
cagtgttttt atttgttttt ttagcagcct                                       30

<210> SEQ ID NO 54
<211> LENGTH: 372
<212> TYPE: DNA
<213> ORGANISM: Trichomonas foetus

<400> SEQUENCE: 54
cggtaggtga acctgccgtt ggatcagttt cgttaataat tacaaacata ttttttttaat       60 gtctataact atttatacaa aattaaacac ataatctaaa aaatttagac cttaggcaat      120
ggatgtcttg gcttcttaca cgatgaagaa cgttgcataa tgcgataagc ggctggatta      180
gctttctttg cgacaagttc gatctttgaa tgcacattgc gcgccgtttt agcttgctag      240
aacacgcata tatgttacag taacccatat taatttaata ccaaattctc ttttaagca      300 aaagagcgaa aaacaaatat gtattaacaa aagggttctg tctcatatag aagacccgc      360 tgaactgaag ca                                                         372

<210> SEQ ID NO 55
<211> LENGTH: 266
<212> TYPE: DNA
<213> ORGANISM: Trichomonas foetus

<400> SEQUENCE: 55
agaccttagg caatggatgt cttggcttct tacacgatga agaacgttgc ataatgcgat       60
aagcggctgg attagctttc tttgcgacaa gttcgatctt tgaatgcaca ttgcgcgccg      120
ttttagcttg ctagaacacg catatatgtt acagtaaccc atattaattt aataccaaat      180
tctcttttta agcaaaagag cgaaaaacaa atatgtatta acaaaagggt tctgtctcat      240
ataggaagac ccgctgaact gaagca                                          266

<210> SEQ ID NO 56
```

```
<211> LENGTH: 46
<212> TYPE: DNA
<213> ORGANISM: artificial
<220> FEATURE:
<223> OTHER INFORMATION: exemplary forward primer for Trichomonas

<400> SEQUENCE: 56
agaccttagg caatggatgt cttggcttct tacacgatga agaacg                         46

<210> SEQ ID NO 57
<211> LENGTH: 42
<212> TYPE: DNA
<213> ORGANISM: artificial
<220> FEATURE:
<223> OTHER INFORMATION: exemplary reverse primer for Trichomonas

<400> SEQUENCE: 57
tgcttcagtt cagcgggtct tcctatatga gacagaaccc tt                             42

<210> SEQ ID NO 58
<211> LENGTH: 60
<212> TYPE: DNA
<213> ORGANISM: artificial
<220> FEATURE:
<223> OTHER INFORMATION: exemplary probe for Trichomonas

<400> SEQUENCE: 58
aagcggctgg attagctttc tttgcgacaa gttcgatctt tgaatgcaca ttgcgcgccg          60

<210> SEQ ID NO 59
<211> LENGTH: 62
<212> TYPE: DNA
<213> ORGANISM: artificial
<220> FEATURE:
<223> OTHER INFORMATION: exemplary probe for Trichomonas

<400> SEQUENCE: 59
aagcggctgg attagctttc tttgcgacaa gttcgatctt tgaatgcaca ttgcgcgcgc          60
cg                                                                         62
```

DNA AMPLIFICATION TECHNOLOGY

CROSS REFERENCE TO RELATED APPLICATIONS

The present Application is a national stage entry of International Patent Application No. PCT/US2015/040035, filed on Jul. 10, 2015, which claims priority to U.S. Provisional Application No. 62/075,769, filed on Nov. 5, 2014, U.S. Provisional Application No. 62/023,123, filed on Jul. 10, 2014, and U.S. Provisional Application No. 62/115,559, filed on Feb. 12, 2015, each of which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FLUO-004_03WO_ST25.txt. The text file is about 15 KB, was created on Jul. 9, 2015, and is being submitted electronically via EFS-Web.

FIELD

The present disclosure concerns methods and materials useful for conducting PCR amplifications. In particular, a nucleic acid amplification design strategy and thermal cycling profile to enable efficient amplification of multiple nucleic acid targets along with improved sensitivity is disclosed.

The present disclosure also describes methods and devices for increasing the melting temperature (Tm) of a primer. In particular, a primer with a synthetic tag appended to it is used to decrease the range between the Tm of the amplicon and the Tm of the primer.

BACKGROUND

PCR amplification has traditionally been accomplished via a plurality of amplification cycles, with each cycle comprising the step of initial denaturation, annealing, polymerization, and final extension. These cycles are generally conducted in a reaction chamber, which is provided with necessary PCR reagents, including the biological sample containing the target nucleotide sequence (generally DNA, or RNA) a DNA polymerase (e.g., Taq polymerase), nucleoside triphosphates, an RT enzyme, and a first and second primer (comprising a primer pair) that hybridize to the target DNA and flank the sequence of the amplified DNA product (the "amplicon"). A PCR apparatus will typically include means for cycling the temperature of the reaction chamber as required for each step of the amplification cycle, including, e.g., "melting" of double stranded DNA to produce single stranded DNA; annealing of the primers to single stranded DNA templates; and extension of the amplified DNA via polymerase.

The precise conditions used to amplify a specific target DNA sequence can vary according to a number of factors which are within the knowledge of those of ordinary skill in the art. In some embodiments of traditional DNA amplification, denaturation is conducted at between about 90-95° C. for about 10-30 seconds, annealing is conducted at about 45-65° C. for about 10-30 seconds; extension is conducted at about 70-75° C. for about 10-90 seconds; and a final extension is conducted at 72° C. for about 5 minutes. In some embodiments, the reaction mixture comprises genomic DNA, $MgCl_2$ and other physiological salts (e.g., NaCl), PCR buffer, 0.1-1.0 mM dNTPs, 0.04-1.5 μM of each primer, and 0.5-5.0 units of heat stable polymerase (e.g., Taq. polymerase).

Other amplification methods known in the art may also be utilized, including, for example, self-sustained sequence replication (3SR), strand-displacement amplification (SDA); "branched chain" DNA amplification (Chiron Corp.); ligase chain reaction (LCR), QB replicase amplification (QBR), ligation activated transcription (LAT), nucleic acid sequence-based amplification (NASBA), repair chain reaction (RCR), and cycling probe reaction (CPR) (reviewed, e.g., in The Genesis Report, DX; Vol. 3(4), pp. 2-7 (February 1994)).

Real-time PCR typically relies on the use of fluorescent molecules that allow quantification or detection of a PCR product in real time, while other detection/quantification chemistries such as electrochemistry are also applicable.

Fluorescent molecules can be DNA binding dyes such as SYBR Green or fluorescently labeled primers or probes. There are many fluorescent dyes and probe designs available for different applications. The most commonly used DNA-binding dye for real-time PCR is SYBR® Green I, which binds preferentially to double-stranded DNA (dsDNA) versus single stranded DNA. SYBR Green I fluorescence increases up to 1,000-fold when it binds to dsDNA. Therefore, fluorescence signal is proportional to the amount of dsDNA present.

The major drawback of DNA-binding dyes is their lack of specificity, that is, DNA-binding dyes bind to any dsDNA. As a result, the presence of any nonspecific products in a real-time or endpoint PCR reaction will contribute to the overall fluorescence and affect the accuracy of quantification or detection. Furthermore, DNA-binding dyes cannot be used for quantification or detection in multiplex reactions because fluorescence signals from different products cannot be distinguished without the inclusion of a post PCR melting curve analysis to distinguish the formation of different products.

In contrast, primer-based and probe-based detection chemistries ensure that signal is generated only when the product of interest is amplified. The primer or target-specific oligonucleotide probe is typically labeled with a reporter fluorophore, but in most cases, fluorescence is quenched when the specific target is not yet amplified or when not present in the sample. Usually this is accomplished by attaching a quencher molecule to the primer or probe, and devising some mechanism by which the reporter and quencher are separated when the primer or probe binds to its specific target.

The principal primer/probe detection chemistries in use today are as follows:

Hydrolysis (TaqMan) Probe

Hydrolysis assays include a sequence-specific, fluorescently labeled oligonucleotide probe, in addition to the sequence-specific primers. Hydrolysis assays exploit the 5' exonuclease activity of certain thermostable polymerases, such as Taq or Tth. The hydrolysis probe is labeled with a fluorescent reporter at one end and a quencher at the opposite end, though several variations on this particular design are in common usage. When the probe is intact, fluorscence is quenched due to fluorophore proximity to the quencher. A commonly used fluorescent reporter-quencher pair is fluorescein (FAM), which emits green fluorescence, and Black Hole Quencher 1 dye, although this is just one of many dye/quencher combinations in use.

The amplification reaction includes a combined annealing/extension step during which the probe hybridizes to the target and the dsDNA-specific 5' to 3' exonuclease activity of Taq or Tth cleaves the oligonucleotide, separating fluorophore from quencher, resulting in a fluorescence signal that is proportional to the amount of amplified product in the sample. A properly designed Hydrolysis probe can be used in combination with additional probes of similar design to determine sequence variations within the amplified target, i.e. genotype.

Molecular Beacons

Molecular beacons are dye-labeled oligonucleotides (25-40 nt) that form a hairpin structure. The 5' and 3' ends have complementary sequences of 5-6 nucleotides that form the stem, while the loop is designed to specifically hybridize to a 15-30 nucleotide section of the target sequence. A fluorescent reporter molecule is attached to one end of the molecular beacon, and a quencher is attached to the other end. When the probe is unbound, hairpin formation occurs, bringing the reporter and quencher into proximity and fluorescence is quenched.

If a target sequence is present during the annealing step of an amplification reaction, the loop portion of the molecular beacon binds to its target sequence, causing the stem to denature. The reporter and quencher are thus separated, quenching is diminished, and the reporter fluorescence is detectable. Because fluorescence is emitted from the probe only when it is bound to the target, the amount of fluorescence detected is proportional to the amount of target in the reaction. Again, a properly designed molecular beacon can be used to distinguish underlying sequence variations, i.e. genotypes, within the amplified sequence. Typically, this is accomplished with melting curve analysis following PCR.

Dual Hybridization Probes

These assays use two sequence-specific oligonucleotide probes which bind to adjacent sequences in the target. The probes are labeled with a pair of dyes that can engage in fluorescence resonance energy transfer (FRET). The donor dye is attached to the 3' end of the first probe, while the acceptor dye is attached to the 5' end of the second probe. This order may be reversed, so long as binding of both oligonucleotides to the target brings the fluorophores within FRET range (Forster radius).

During real-time PCR, excitation is performed at a wavelength specific to the donor dye, and the reaction is monitored at the emission wavelength of the acceptor dye. At the annealing step, the probes hybridize to their target sequences in a head-to-tail arrangement. This brings the donor and acceptor dyes into proximity, allowing FRET to occur. The amount of acceptor fluorescence is proportional to the amount of PCR product present. Hybridization probes enable a variety of genetic detection and quantification readouts.

Primer/Probe Combinations

These detectors use a sequence specific oligonucleotide primer and a sequence specific oligonucleotide probe. The primer and the probe are designed to bind to adjacent sequences of the target, usually with the probe complementary to the strand formed by the primer. The probe and the primer are labeled with a pair of dyes that can engage in (FRET). Generally, the donor dye is attached near the 3' end of the primer, while the acceptor dye is attached to the 3' end of the probe, which anneals to the complementary strand synthesized by primer extension.

As with the dual hybridization probes, during DNA amplification, excitation is performed at a wavelength specific to the donor dye, and the reaction is monitored at the emission wavelength of the acceptor dye. At the annealing step, the probe and primer hybridize to their target sequences in a head-to-tail arrangement. This brings the donor and acceptor dyes into proximity, allowing FRET to occur. The increasing amount of acceptor fluorescence is proportional to the amount of PCR product present.

Dynamic Flux Amplification

An amplification method described in the art comprises determining the melting temperature of the target sequence and setting the upper limit of the thermal cycle temperature to maximize the denaturation of the target sequence while minimizing the denaturation of the non-target sequences (dynamic flux amplification or DFA). This approach fosters the creation of a bubble as the reaction is heated to a temperature approaching the denaturation temperature of the target sequence. Assuming the denaturation temperature of the target sequence is less than the adjacent sequences, the adjacent sequences will remain annealed, resulting in a bubble forming in the DNA strand as the target sequence denatures. Of course, it is probable that multiple bubbles form at various points along the DNA sequence that possess a similar denature temperature to the target sequence. Nevertheless, the total amount of un-denatured sequence is still less than would be the case if the upper temperature was raised to 95° C. or more.

One advantage of controlling the denaturation temperature to create a nucleic acid bubble is that it significantly limits the formation of nonspecific product by preventing the binding of the primers to sites other than the target sequence, by making such sites unavailable for hybridization. This results from the target sequence being favored to denature relative to non-target regions of the target genome and thereby significantly reduces the available sequence that can serve as non-specific binding sites during the amplification process.

One disadvantage of the aforementioned conventional probe chemistries is that they are not compatible with Dynamic Flux Amplification ("DFA") technology. This is due in part to the difference in required melting temperatures of the probes used in PCR as compared to DFA. PCR utilizes probes that are generally in the 20-30 base pair range and generally possess a Tm of at least 20° C. less than the Tm of the sequence of interest. In contrast, DFA requires probes that are within 20° C. or less of the Tm of the sequence of interest. Because DFA normally operates outside of annealing temperature ranges used in probe technology for PCR, such probes as currently practiced are generally not compatible with DFA technology.

It would be desirable if existing PCR primers could be modified to take advantage of the narrow temperature range used in DFA or at the very least a thermal cycling range that is narrower than those used in conventional PCR and thus obviate the need to completely redesign primers in order to obtain an increase in speed. The narrow temperature range can be used as a target temperature range in order to identify, design and/or generate specific primers that have sufficiently high Tm values when hybridized with the target nucleic acid.

It would be desirable to have an amplification method that significantly eliminated the formation of undesirable product by inhibiting the extension of the reaction beyond the amplification bubble.

Often the primers with the necessary Tm ranges must be designed de novo. Thus, although users of traditional PCR assays may desire increased speed, the cost of designing, evaluating and optimizing the primers for DFA necessary to obtain the narrower cycling range is frequently prohibitive, locking users into the slower conventional PCR, rather than taking advantage of the increased speed possible from dynamic flux amplification.

Thus, there is a need in the art to develop primers and probes, other reagents, and methodologies, which are compatible with DFA. Specifically, there is an unmet need in the art to develop primers and probes that can be utilized in DFA protocols.

In some aspects, the term "extreme chain reaction" or "XCR" will be utilized in the description. The present inventors utilize the term XCR as a synonym for DFA. Thus, the two terms are used interchangeably.

Multiplex Detection

The need for, at a minimum, the ability to detect two or more distinct amplified targets within a single reaction is a fundamental aspect of modern diagnostic tests. Although some tests can be brought to market with separate reaction vessels containing the necessary test performance controls, it is cost effective in terms of sample throughput, and reagent usage, to incorporate the reaction controls within a single reaction vessel. Effective utilization of DFA ideally would involve a means to detect one or more amplified targets simultaneously.

Another consequence of being able to custom design target denaturation and primer annealing temperatures while simultaneously narrowing the thermal cycling range allows for amplification of different targets to be carried out in a single reaction vessel by thermal cycling the reaction vessel at different temperature ranges in succession.

Probe technology for use with both PCR primers as well as the high Tm and frequently longer primers commonly used in DFA have been disclosed in WO 2015/054516 (incorporated herein in its entirety for all purposes).

SUMMARY OF THE DISCLOSURE

In one aspect of the invention, the disclosure provides oligonucleotide primers with increased melting temperatures for more specific amplification of target nucleic acids.

In one embodiment, an oligonucleotide primer for amplification of a target nucleic acid sequence in a polymerase chain reaction (PCR) comprises: a first region, wherein the first region is complementary to a strand of the target nucleic acid sequence and is located at the 3' end of the primer; and a second region, wherein the second region is located at the 5' end of the primer; and wherein the Tm of the oligonucleotide primer is increased compared to the Tm of an oligonucleotide primer having only the first region.

In another embodiment, the oligonucleotide primer comprises a transition between the first and second regions. In yet another embodiment, the transition comprises a single nucleotide, a chain of carbons, a multifunctional moiety, modified nucleotides, modified backbones or a combination thereof.

In one embodiment, the melting temperature (Tm) of the oligonucleotide primer is within at least 15° C. of the Tm of the target nucleic acid sequence. In another embodiment, the Tm of the oligonucleotide primer is within at least 10° C. of the Tm of the target nucleic acid sequence. In another embodiment, the Tm of the oligonucleotide primer is within at least 5° C. of the Tm of the target nucleic acid sequence. In another embodiment, the Tm of the oligonucleotide primer is within at least 2.5° C. of the Tm of the target nucleic acid sequence. In another embodiment, the Tm of the oligonucleotide primer is equal to the Tm of the target nucleic acid sequence.

In one embodiment, the second region of the oligonucleotide primer comprises nucleotide or backbone modifications to optimize annealing of the oligonucleotide primer to the target nucleic acid region.

In one embodiment, the second region is an arbitrary sequence that is not complementary to either strand of the target nucleic acid sequence.

In one embodiment, the second region is complementary to a strand of the target nucleic acid sequence that is opposite to the strand of the target nucleic acid sequence that the first region is complementary to. In another embodiment, the second region comprises cleavable chemistries to inhibit cleavage by a polymerase.

In one embodiment, the oligonucleotide primer comprises a sequence of cytosine nucleotides adjacent to a first sequence of guanosine nucleotides. In another embodiment, the number of nucleotides between the cytosine and guanosine nucleotides is less than 5. In another embodiment, the number of nucleotides between the cytosine and guanosine nucleotides is less than 4. In another embodiment, the number of nucleotides between the cytosine and guanosine nucleotides is less than 3. In another embodiment, the number of nucleotides between the cytosine and guanosine nucleotides is less than 2. In another embodiment, the number of nucleotides between the cytosine and guanosine nucleotides is 0. In another embodiment, the primer can form a Guanosine quadruplex structure.

In one embodiment, the oligonucleotide primer further comprises a second sequence of guanosine nucleotides adjacent to the first sequence of guanosine nucleotides. In another embodiment, the second sequence of guanosine nucleotides causes the primer to shift and form a Guanosine quadruplex structure.

In another aspect of the invention, the disclosure provides for a method for increasing the melting temperature (Tm) of an oligonucleotide primer for amplification of a target nucleic acid sequence in a polymerase chain reaction (PCR), comprising: identifying a target nucleic acid sequence from one or more segments of DNA; designing an oligonucleotide primer having a first region and a second region, wherein the first region is complementary to a strand of the target nucleic acid sequence and is located at the 3' end of the primer and the second region is located at the 5' end of the primer; and wherein the Tm of the oligonucleotide primer is increased compared to the Tm of an oligonucleotide primer having only the first region.

In another aspect of the invention, the disclosure provides for a method for nucleic acid sequence amplification, comprising: identifying a target nucleic acid sequence from one or more segments of DNA comprising target and non-target nucleic acid sequences; obtaining a first oligonucleotide primer and a second oligonucleotide primer of the invention; and amplifying the target nucleic acid sequence by thermal cycling the target nucleic acid sequence and the first and second oligonucleotide primers, wherein thermal cycling comprises: (i) denaturing the target nucleic acid; (ii) hybridizing the first oligonucleotide primer to a first strand and the second oligonucleotide primer to a second strand of the denatured target nucleic acid; (iii) extending the first and second oligonucleotide primers by polymerization with a polymerase to create two new strands of the target nucleic acid; (iv) denaturing the two new strands from the first and second strands of the target nucleic acid; (v) hybridizing the first oligonucleotide primer to the first strand and to one new strand and the second oligonucleotide primer to the second strand and to the other new strand of the target nucleic acid; (vi) extending the first and second oligonucleotide primers by polymerization with a polymerase to create four additional new strands of the target nucleic acid; repeating steps (i) through (vi) to create multiple strands of the target nucleic acid that have incorporated the second regions of the first and second oligonucleotide primers; and wherein an upper thermal cycle temperature in the thermal cycling is selected to minimize non-target denaturation and maximize target denaturation.

In one embodiment of the method for nucleic acid sequence amplification, the thermal cycling creates a bubble comprised of denatured target nucleic acid sequence and adjacent annealed non-target nucleic acid sequence. In another embodiment, the oligonucleotide primers prevent amplification of the target nucleic acid sequence beyond the bubble.

In another aspect of the invention, the disclosure provides for a method for amplifying and detecting two or more target nucleic acid sequences in a sample, comprising: identifying two or more target nucleic acid sequences from one or more segments of DNA; obtaining a pair of oligonucleotide primers specific for each target nucleic acid sequence, wherein each pair of oligonucleotide primers has an annealing curve ($T_A$) that overlaps with a denaturation curve ($T_D$) of its target nucleic acid sequence, in such a manner as to minimize the temperature range between the higher of the melting temperature of the pair of oligonucleotide primers and the melting temperature of its target nucleic acid sequence; amplifying each target nucleic acid sequence by thermal cycling each pair of oligonucleotide primers and its target nucleic acid sequence within a specific temperature range, wherein the thermal cycling at different temperature ranges in succession leads to amplification of the two or more target nucleic acid sequences; and detecting the two or more amplified target nucleic acid sequences.

In one embodiment of the method for amplifying and detecting two or more target nucleic acid sequences in a sample, each amplified target nucleic acid sequence is about 400 bp or greater. In another embodiment, one or more temperature suitable polymerases are chosen for each temperature range.

In one embodiment, one or more of the target nucleic acid sequences is an internal control. In another embodiment, the pair of oligonucleotide primers specific for the internal control is the same as the pair of oligonucleotide primers specific for a target nucleic acid sequence except for mismatches that allow amplification of the internal control at a different temperature range than that of the target nucleic acid sequence.

In one embodiment, each pair of oligonucleotide primers is used only at its own thermal cycling temperature range. In another embodiment, the thermal cycling at each temperature range comprises as many cycles as necessary for amplification of each target nucleic acid sequence.

In one embodiment, the thermal cycling comprises cycling at temperature ranges in succession, beginning with the lowest temperature range and moving to the highest temperature range. In another embodiment, the thermal cycling comprises cycling at temperature ranges in succession, beginning with the highest temperature range and moving to the lowest temperature range.

In one embodiment, there is overlap between one or more temperature ranges. In another embodiment, the thermal cycling comprises temperature ranges of from about 50° C. to about 65° C., from about 60° C. to about 95° C. and from about 90° C. to about 105° C. In another embodiment, the thermal cycling comprises temperature ranges of from about 45° C. to about 72° C. and from about 72° C. to about 99° C. In another embodiment, the thermal cycling comprises temperature ranges of from about 54° C. to about 63° C., from about 63° C. to about 81° C. and from about 81° C. to about 99° C.

In one embodiment of the method for amplifying and detecting two or more target nucleic acid sequences in a sample, the detecting comprises using fluorescent dyes, electrochemical indicators, target immobilization strategies, or any combination thereof.

In one embodiment, the amplifying step further comprises thermal cycling each pair of oligonucleotide primers, its target nucleic acid sequence and an oligonucleotide probe complementary to the target nucleic acid sequence and having a cleavable sequence. In another embodiment, each oligonucleotide probe comprises a fluorescent dye and quencher located interchangeably on the 5' or 3' end of each probe. In another embodiment, each oligonucleotide probe comprises the same fluorescent dye located interchangeably on the 5' or 3' end of each probe. In another embodiment, the cleavable sequence of each oligonucleotide probe is cleaved by polymerization-independent cleavage or by polymerization-dependent cleavage by a polymerase. In another embodiment, one or more oligonucleotide probes is a hybrid hairpin/cleaved probe.

In one embodiment of the method for amplifying and detecting two or more target nucleic acid sequences in a sample, the detecting step comprises detecting a signal resulting from cleavage of said probe.

In one embodiment of the method for amplifying and detecting two or more target nucleic acid sequences in a sample, the amplifying step further comprising thermal cycling each pair of oligonucleotide primers, its target nucleic acid sequence and an oligonucleotide probe complementary to the target nucleic acid sequence and having a cleavable sequence, the two or more target nucleic acid sequences comprise a *Trichomonas* sequence and a *Xenorhabdus nematophila* sequence. In another embodiment, the *Xenorhabdus nematophila* sequence is a control sequence. In another embodiment, the pair of oligonucleotide primers specific for the *Trichomonas* sequence comprises SEQ ID NO: 56 and SEQ ID NO: 57. In another embodiment, the oligonucleotide probe complementary to the *Trichomonas* sequence comprises SEQ ID NO: 59. In another embodiment, the pair of oligonucleotide primers specific for the *Xenorhabdus nematophila* sequence comprises SEQ ID NO: 51 and SEQ ID NO: 52. In another embodiment, the oligonucleotide probe complementary to the *Xenorhabdus nematophila* sequence comprises SEQ ID NO: 53. In another embodiment, the thermal cycling comprises temperature ranges of from about 89° C. to about 74° C. and from about 63° C. to about 78° C. In another embodiment, the thermal cycling from about 89° C. to about 74° C. amplifies the *Trichomonas* sequence. In another embodiment, the thermal cycling from about 63° C. to about 78° C. amplifies the *Xenorhabdus nematophila* sequence.

In one embodiment, a method of detecting *Trichomonas* in cattle comprises: obtaining a pair of oligonucleotide primers specific for a *Trichomonas* target nucleic acid sequence; obtaining a pair of oligonucleotide primers specific for a *Xenorhabdus nematophila* control nucleic acid sequence; wherein each pair of oligonucleotide primers has an annealing curve ($T_A$) that overlaps with a denaturation curve ($T_D$) of its target nucleic acid sequence, in such a manner as to minimize the temperature range between the higher of the melting temperature of the pair of oligonucleotide primers and the melting temperature of its target nucleic acid sequence; amplifying each nucleic acid sequence by thermal cycling each pair of oligonucleotide primers and its target nucleic acid sequence within a specific temperature range, wherein the thermal cycling at different temperature ranges in succession leads to amplification of the *Trichomonas* and *Xenorhabdus nematophila* sequences; and detecting the amplified target nucleic acid sequences.

In one embodiment of the method for amplifying and detecting two or more target nucleic acid sequences in a sample, one or both of each pair of oligonucleotide primers comprises a triplex forming region (TFR). In another embodiment, the TFR primer creates strands of triplex forming DNA when the target nucleic acid sequence includes a sequence having complementarity with the sequence of the TFR primer. In another embodiment, the target nucleic acid sequence includes a natural triplex forming region.

In one embodiment of the method for amplifying and detecting two or more target nucleic acid sequences in a sample, one or both of each pair of oligonucleotide primers further comprises a label.

In one embodiment, the method further comprises one or more triplex forming oligonucleotide (TFO) probes that hybridizes to one or more TFRs, thus forming a triplex, in a double stranded DNA sequence that was created during an amplification process of a target nucleic acid sequence by one or more TFR primers. In another embodiment, the TFO probe is designed to anneal at approximately the same, or lower, temperature than a Tm of the TFR primer. In another embodiment, the method further comprises one or more non-specific DNA binding dyes that bind with hybridized triplex DNA. In another embodiment, the method further comprises one or more quadruplex binding dyes.

In one embodiment, each TFO probe includes a label moiety selected from the group consisting of: a fluorescent moiety, radioactive moiety, color moiety, fluorescent reporter moiety, fluorescent quenching moiety, one of a pair of fluorescent resonance energy transfer moieties, and combinations thereof. In another embodiment, one or more of the TFO probes is a triplex forming fluorescent probe (TFFP). In another embodiment, one or more of the TFO probes is a triplex forming fluorescent probe (TFFP) and the double stranded DNA has a receptor dye. In another embodiment, the label moiety is the same for each TFO probe. In another embodiment, a cap at the 3' end of the TFO probe inhibits extension from the 3' end of the probe.

In one embodiment, the double stranded DNA has a first label and the TFO probe has a second label, wherein the first label and second label provide a detectable emission upon close association.

In one embodiment, the TFO probe includes a fluorescent dye and quencher. In another embodiment, the TFO probe includes a fluorescent dye and quencher in a hairpin configuration.

Also provided herein are kits comprising any of the aforementioned oligonucleotides, primers, probes, and reaction agents.

These and other features, aspects, and advantages of embodiments of the present disclosure, will become better understood with regard to the following description, claims, and accompanying drawings, explained below.

BRIEF DESCRIPTION OF THE DRAWINGS

FIG. 8A depicts the two extension products from the first cycle of amplification. The point at which the tag (either tag 42 or tag 46) transitions to the primer (either primer 32 or primer 38) is designated by a T, to denote a transition. FIG. 8B depicts the amplification of extension 70 with the annealing of fresh primer 58 comprising tag 66 to the 3' end of extension 50. FIG. 8C depicts the amplification of extension 79 with the annealing of primer 32 comprising tag 42 to the 3' end of extension 54.

DETAILED DESCRIPTION

Figure 1A:
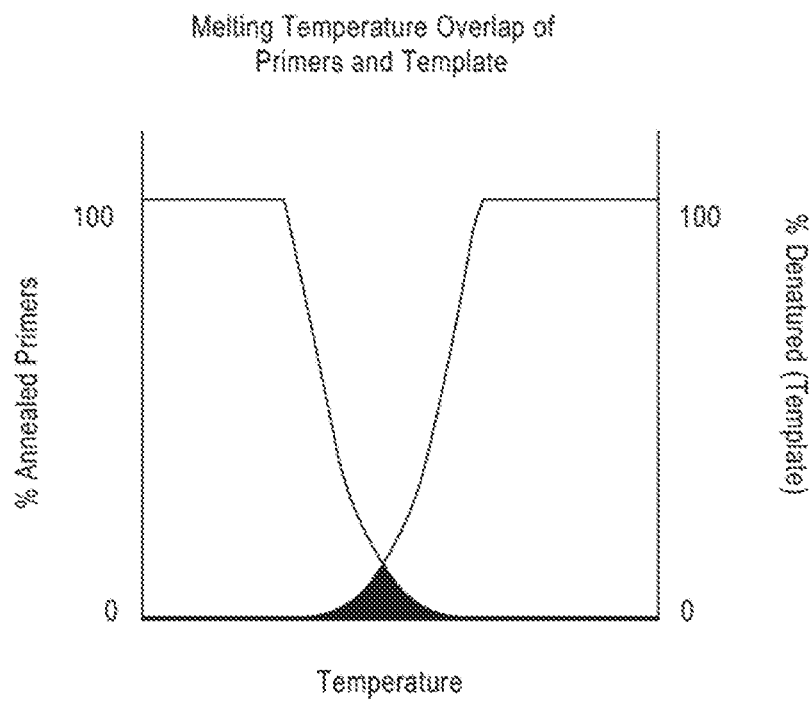
FIG. 1A and FIG. 1B show graphical representations of a design for overlapping primer annealing temperatures and template denaturation temperatures (FIG. 1A) and a design for non-overlapping primer annealing temperatures and template denaturation temperatures (FIG. 1B).

In the description and tables which follow, a number of terms are used, in order to provide a clear and consistent understanding of the specification and claims, including the scope to be given such terms, the following definitions are provided.

Definitions

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The term "a" or "an" refers to one or more of that entity; for example, "a primer" refers to one or more primers or at least one primer. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

The term "adjacent" as used herein refers to the positioning of the primer with respect to the probe on its complementary strand of the template nucleic acid in which the nucleotides may directly abut one another. Alternatively, for use in the polymerization-dependent process, as when the present method is used in the PCR and DFA and detection methods as taught herein, the "adjacency" may be anywhere within the sequence to be amplified, anywhere downstream of the primer such that primer extension will position the polymerase so that cleavage of the probe occurs.

The term "allele" as used herein is any of one or more alternative forms of a gene which relate to one trait or characteristic. In a diploid cell or organism, the two alleles of a given gene occupy corresponding loci on a pair of homologous chromosomes.

The term "amino acid sequence" as used herein includes an oligopeptide, peptide, polypeptide, or protein and fragments thereof that are isolated from, native to, or naturally occurring in a plant, or are synthetically made but comprise the nucleic acid sequence of the endogenous counterpart.

A "biological sample" described herein can include any biological material taken from a subject, including, but not limited to, expectorations (e.g., sputum), blood, blood cells (e.g., lymphocytes), tissue, biopsies, cultured cells, pleural, peritoneal, or cerebrospinal fluid, sweat, feces, and urine. In some embodiments, a biological sample from a subject is treated, e.g., to culture an infectious microorganism and/or amplify its genetic material, before being assayed according to methods provided herein.

The term "bioluminescence" refers to a form of chemiluminescence in which the light-emitting compound is one that is found in living organisms. Examples of bioluminescent compounds include bacterial luciferase and firefly luciferase.

The term "drug" as used herein can refer to any compound, agent, treatment modality, or combination thereof. In some preferred aspects, the drug is an antibiotic compound.

The term "efficiency" as used herein refers to a hallmark of Real-Time PCR assays. An ideal qPCR (quantitative PCR) reaction has an efficiency of 100% with a slope of −3.32, which correlates with a perfect doubling of PCR product during each cycle. However, slopes between −3.1 and −3.6 with efficiencies between 90 and 110% are generally considered acceptable (Commission, C. A. (2009). Definition of Minimum Performance Requirements for Analytical Methods of GMO Testing European Network of GMO Laboratories (ENGL), (October 2008), 1-8). Efficiency is established by replicated standard curves. Amplification efficiency is determined from the slope of the log-linear portion of the standard curve and is calculated as $E=(10(-1/slope)-1)*100$. (Bustin, S. A., et al. (2009). The MIQE Guidelines: Minimum I information for Publication of Quantitative Real-Time PCR Experiments. Clinical Chemistry, 55(4), 1-12. doi:10.1373/clinchem.2008.112797).

The term "fluorophore" refers to a compound which is capable of fluorescing, i.e. absorbing light at one frequency and emitting light at another, generally lower, frequency.

The term "homogeneous", as used herein applied to multi-step processes, refers to methods for carrying out the steps of the process, wherein the need for sample handling and manipulation between steps is minimized or eliminated. For example, a "homogeneous" amplification/detection assay refers to a coupled amplification and detection assay wherein the need for sample handling and manipulation between the amplification and detection is minimized or eliminated.

The term "intercalator" refers to an agent or moiety capable of non-covalent insertion between stacked base pairs in a nucleic acid double helix.

The term "label" as used herein refers to any atom or molecule which can be used to provide a detectable (preferably quantifiable) signal or to interact with a second label to modify the detectable signal provided by the second label. The label can be attached to a nucleic acid or protein. Labels may be light-emitting compounds which generate a detectable signal by fluorescence, chemiluminescence, phosphorescence, or bioluminescence. In the alternative, labels may provide signals detectable by radioactivity, electrochemistry, colorimetry, or by the absorption of light, producing fluorescence, or may be used to immobilize a product to an array.

The term "linearity" as used herein refers to a hallmark of optimized Real-Time PCR assays and is determined by the R2 value obtained by linear regression analysis, which should be ≥0.98 (Bustin et al., 2009).

The term "microorganism" as used herein can refer to bacteria, archaea, fungi, protozoa, parasites and/or viruses.

The terms "nucleic acid" and "oligonucleotide" refer to primers, probes, and oligomer fragments to be detected, and shall be generic to polydeoxyribonucleotides (containing 2-deoxy-D-ribose), to polynucleotides (containing D-ribose), and to any other type of polynucleotide which contains an N glycoside of a purine or pyrimidine base, or modified purine or pyridine base. There is no intended distinction in length between the terms "nucleic acid" and "oligonucleotide", and these terms will be used interchangeably These terms refer only to the primary structure of the molecule. Thus, these terms include double and single stranded DNA, as well as double and single stranded RNA.

The oligonucleotide is not necessarily physically derived from any existing or natural sequence but may be generated in any manner, including chemical synthesis, DNA replication, reverse transcription, or a combination thereof. The terms "oligonucleotide" intend a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present disclosure and include, for example, inosine and 7-deasaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

The terms "target nucleic acid(s)" as used herein refers to nucleic acids derived from an infectious microorganism, human, mammalians, or plants. In some aspects, a target nucleic acid is a nucleic acid of an organism or a microorganism that is assayed according to a method provided herein.

The terms "target region", "target sequence", and "target nucleic acid sequence" refer to a region of a nucleic acid which is to be detected, quantified, or genotyped.

The term "reference nucleic acid" as used herein refers to a nucleic acid corresponding to a target nucleic acid (e.g., representing the same portion of genomic DNA), that differs from the target nucleic acid by one or more sequence variations. For example, in some aspects, a reference nucleic acid has the sequence of a wild-type microorganism (e.g., with respect to responsiveness to a drug of interest). In further aspects, a reference nucleic acid has the sequence of a wild-type human cell, such as a diseased cell, including, e.g., a human cancer cell.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of five different deoxyribonucleoside triphosphates and polymerization-inducing agents such as DNA polymerase or reverse transcriptase, in a suitable temperature. The primer is preferably single stranded for maximum efficiency in amplification.

The term "probe" refers to an oligonucleotide, typically labeled, that forms a duplex structure with a sequence of a target nucleic acid due to complementary base pairing. The probe will comprise a "hybridizing region", preferably consisting of 30 or more nucleotides, and in some instances, consisting of 50 or more nucleotides, corresponding to a region of the target sequence. Ideally, the Tm of the probe will be within 30 degrees or less of the Tm of the sequence of interest. "Corresponding" means identical to or complementary to the designated nucleic acid. The probe, preferably, does not contain a sequence complementary to sequence(s) used to prime the PCR. Generally, the 3' terminus of the probe will be "blocked" to prohibit incorporation of the probe into a primer extension product. "Blocking" can be achieved by using non-complementary bases or by adding a chemical moiety such as biotin, a phosphate group, or a fluorophore to the 3' hydroxyl of the base nucleotide, which may, depending on the selected moiety, serve a dual purpose by also acting as a label for subsequent detection or capture of the nucleic acid attached to the label. Blocking can also be achieved by removing the 3'-OH or by using a nucleotide that lacks a 3'-OH such as dideoxynucleotide.

The term "quenching" refers to a decrease in fluorescence of a first compound caused by a second compound, regardless of the mechanism. Quenching typically requires that the compounds be in close proximity. As used herein, either the compound or the fluorescence of the compound is said to be quenched, and it is understood that both usages refer to the same phenomenon.

The terms "responsiveness" and "drug responsiveness" as used herein can refer to resistance, sensitivity, susceptibility, tolerance and/or other phenotypic characteristics of a microorganism or diseased cell, such as a cancer sell, related to the therapeutic effect of a drug, including non-responsiveness. Drug responsiveness can be assessed directly, according to the effect of the drug on a targeted microorganism or diseased cell, such as a cancer cell (e.g., a bacterial mortality or a cellular mortality), and/or indirectly, according to the effect of the drug on one or more aspects of an infectious disease caused by the microorganism (e.g., prevention, amelioration, alleviation, and/or elimination of the disease or one or more symptoms of the disease). In some preferred aspects, systems and methods are provided herein for detecting resistance to one or more drugs, where resistance refers to inheritable (genetic) resistance.

The terms "sequence-specific oligonucleotide" and "SSO" refer to oligonucleotide probes wherein the hybridizing region is exactly complementary to the sequence to be detected. This is known as "stringent hybridization." The use of stringent hybridization conditions under which the probe will hybridize only to that exactly complementary target sequence allows for detection of the specific target sequence. Stringent hybridization conditions are well known in the art (see, e.g., Sambrook, et al., 1985, molecular cloning—A Laboratory Manual, Cold Springs Harbor, N.Y., incorporated herein by reference). Stringent conditions are sequence dependent and will be different in different circumstances.

The term "sequence variation" as used herein, in relation to nucleic acids, refers to a difference in the sequence of a nucleic acid relative to the sequence of a corresponding nucleic acid (e.g., a sequence representing the same gene or other portion of genomic DNA). In some embodiments, sequence variations detected according to various methods provided herein are "Single Nucleotide Polymorphisms" ("SNPS"), resulting from a difference in the identity of a single nucleotide between a target nucleic acid and a reference nucleic acid. In further embodiments, sequence variations detected according to various methods provided herein include "multiple nucleotide Polymorphisms." In some embodiments, the reference nucleic acid corresponds to a non-drug resistant phenotype and a drug resistant phenotype is detected according to a method provided herein by identifying a sequence variation between the reference nucleic acid and a target nucleic acid of a biological sample from a subject infected with the microorganisms or diseased cell, such as a drug resistance cancer cell.

The "subject" referred to herein can be any organism capable of hosting a microorganism, including but not limited to, experimental animals (e.g., mice, rats, rabbits, and the like) and humans. In various embodiments, the subject is a human patient suffering from an infectious disease. In other embodiments, the subject is the organism itself, such as the human patient.

The term "subsequence" refers herein to a nucleotide sequence contained within another sequence.

The Tm is the temperature (e.g., under defined ionic strength and pH) at which 50% of the oligonucleotides have dissociated. Relaxing the stringency of the hybridizing conditions will allow sequence mismatches to be tolerated; the degree of mismatch tolerated can be controlled by suitable adjustment of the hybridization conditions.

The term "variable sequence element" refers to a region of a nucleic acid (e.g., DNA or RNA) comprised of a string of adjacent nucleotides that includes at least one sequence variation known to be associated with a phenotypic characteristic of interest, such as resistance, sensitivity, and/or other aspects of drug responsiveness or propensity for a particular disease such as cancer or heart disease, or more mundane phenotypic characteristics such as eye color or hair color. For example, a sequence variation associated with drug resistance will often occur in a region of a nucleic acid that encodes a site of the corresponding protein that is a structural and/or functional determinant of drug responsiveness, such as a drug binding site. A variable sequence element including the known variation (and surrounding nucleotides) will likely encode structurally and/or functionally related portions of the protein (e.g., a pocket, fold, or other structure that comprises the drug blinding site), and additional, uncharacterized variations within the variable sequence element will likely be associated with the same phenotype as the known variations.

As defined herein, "5'→3' nuclease activity" or "5' to 3' nuclease activity" refers to that activity of a template specific nucleic acid polymerase including either a 5' to 3' exonuclease activity traditionally associated with some DNA polymerase, whereby nucleotides are removed from the 5' end of an oligonucleotide in a sequential manner, (i.e., *E. coli* DNA polymerase I has this activity, whereas the Klenow fragment does not), or a 5' to 3' endonuclease activity wherein cleavage occurs more than one phosphodiester bond (nucleotide) from the 5' end, or both.

The term "reaction mixture" refers to a solution containing reagents necessary to carry out the reaction. An "amplification reaction mixture", which refers to a solution containing reagents necessary to carry out an amplification reaction, typically contains oligonucleotides primers and a DNA polymerase in a suitable buffer. Reaction mixtures for specific reactions are well-known in the literature.

A "singleplex reaction" means a reaction where only one product is being tested for in a single reaction vessel.

A "duplex reaction" means a reaction where two products are being tested for in a single reaction vessel.

A "multiplex reaction" means a reaction where more than two products are being tested for in a single reaction vessel.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into sub-ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Dynamic Flux Amplification

Generally, the present disclosure relates to nucleic acids as well as the devices, systems, and methods for using the same in conjunction with a method of DNA amplification hereinafter referred to as "Dynamic Flux Amplification" or "DFA." DFA is disclosed in U.S. Pat. No. 7,838,235, which is herein incorporated in its entirety for all purposes. Methods are described for improved amplification of nucleic acid sequences that comprise utilizing oligonucleotide primer designs and target sequence designs in combination to achieve precise temperature ranges for the annealing of primers with the target nucleic acid, amplification of the target nucleic acid, and denaturation of the amplified target nucleic acid product.

Generally, DFA refers to specific techniques of DNA and RNA amplification. DFA takes advantage of the fact that DNA amplification can take place within a fairly narrow temperature range. Once the Tm of the sequence of interest is determined, the DNA sample may be heated to that temperature or 1° C. to 5° C. above that temperature. This defines the upper parameter of the heating and cooling cycle. The Tm of either the primers or the probes, (whichever possesses the lower Tm) defines the lower parameter of the heating and cooling cycle, within 1° C. to 5° C.

In practicing DFA, it is generally preferred to use primers with a Tm as close as possible to the Tm of the sequence of interest so that the temperature may be cycled within a narrow range. The result of this narrow cycling is a dynamic opening and closing of a duplex between complementary nucleic acids comprising the sequence of interest as opposed to the complete, or nearly complete denaturing of the entire DNA strand. The present existing primers (e.g., primers that were tested) target nucleic acid product that contains fewer nonspecific products. Thus, the amplified target nucleic acids products can be overall more specific and sensitive for quantitative PCR and genotyping target detection applications as described herein.

The rational design of oligonucleotide primers can include the selection via calculation, experiment, or computation of primers that have the desired melting temperature (Tm). The rational design can include selection of a specific primer sequence with the appropriate % GC to obtain the desired Tm. Also, the rational design can include modifications to the primers that include internucleotide modifications, base modifications, and nucleotide modifications.

DFA Primer Design Methodology

In some embodiments, methods are provided for selecting primers for PCR that flank a variable sequence element of interest on a target nucleic acid.

In some embodiments, primers are selected to have a Tm with the target nucleic acid (primer:target Tm) that is within a narrow range of the Tm of the target nucleic acid (target: target Tm). The specific, narrow temperature range used for such an amplification of the target nucleic acids is dependent on the melting profile of the target nucleic acid, and thereby the sequence of the target nucleic acid being amplified. As such, the narrow temperature range can be used as a target temperature range in order to identify and/or generate specific primers that have sufficiently high Tm values when hybridized with the target nucleic acid.

DFA Primer Design—Overlapping Annealing/Denaturing Curves

Figure 1B:
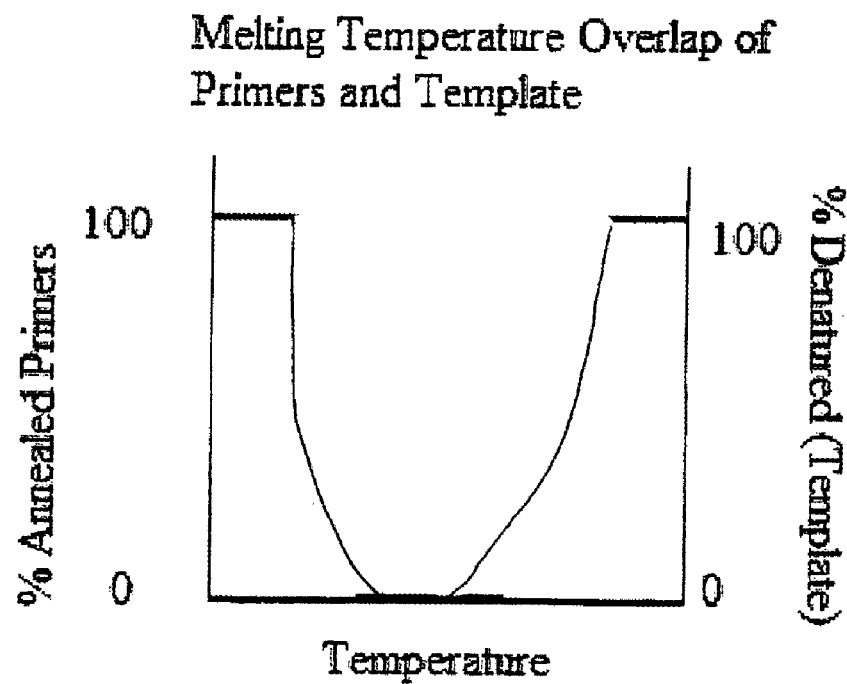
Figure 2:
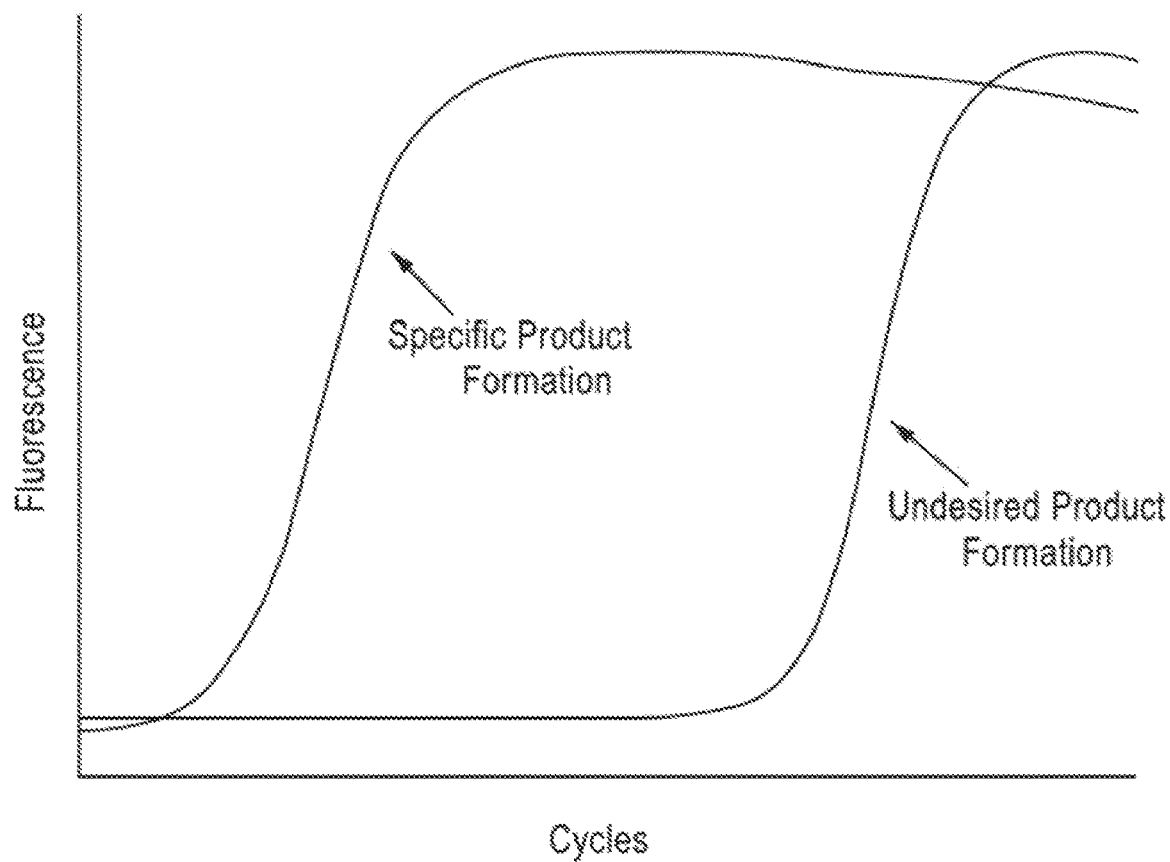
FIG. 2 is an illustration of conventional amplification products by real time PCR.

Accordingly, the Tm values of the primers can be overlapping within the temperature range of annealing and/or denaturing of the target nucleic acid (See, FIG. 1A). FIG. 1A can be contrasted with FIG. 1B to illustrate the design of the primers to have the Tm within a range of the Tm of the target nucleic acid. FIG. 1B shows that conventional amplification with primers and a target nucleic acid are devoid of having a temperature overlap and require extreme temperature variations during amplification, corresponding to denaturation, annealing and extension cycles, to produce an amplified product. Such extreme temperature ranges allow for the formation of undesired products as depicted in FIG. 2.

DFA Primer Design—Iterative Design

In some embodiments, an iterative design process is provided to select and/or optimize primers for specific target nucleic acid sequences to be amplified and/or detected. Advantageously, the iterative method enables the formation of a specific target nucleic acid by using a narrow range of thermal conditions where both the target nucleic acid and the oligonucleotide primers hybridized with the target nucleic acid are in a dynamic flux of annealing and denaturing. Such a dynamic flux of annealing and denaturing can result in a specific amplification of the target nucleic acid with a commensurate decrease in the formation of nonspecific amplification products. The implications of such iterative methods for selecting and/or optimizing primers provides for the use of low cost dyes in lieu of more expensive custom oligonucleotide probes (such as those having fluorescent labels) can allow for quantitative PCR or high resolution denaturation to be used in analyzing the sequence of the target nucleic acid. Also, the iterative method can provide primers that function in the absence of exquisite thermally controlled instruments for the formation of amplification products.

That is, the primers can operate within a narrow temperature range in order to amplify the target nucleic acid, allowing nucleic acid amplification to be used in a much broader range of uses. A number of methods have been described in the art for calculating the theoretical Tm of DNA of known sequence, including, e.g., methods described by Rychlik and Rhoads, Nucleic Acids Res. 17:8543-8551 (1989); Sambrook, J. et al., Molecular Cloning: A Laboratory Manual, Cold Spring Harbor Laboratory Press, Cold Spring Harbor, N.Y. (1989); Breslauer et al., Proc Natl Acad. Sci. 83: 3746-3750 (1986); SantaLucia, J Jr. (1998) "A unified view of polymer, dumbbell, and oligonucleotide DNA nearest-neighbor thermodynamics." Proc. Natl. Acad. Sci. USA 95, 1460-1465 (Abstract). Mismatches: Allawi, H T & SantaLucia, J Jr. (1997) "Thermodynamics and NMR of Internal G•T Mismatches in DNA" Biochemistry 36, 10581-10594.

Such an iterative process can include identifying an initial target nucleic acid sequence as the target amplicon, wherein the target nucleic acid sequence can be associated with a particular biological activity, such as possible drug resistance. The target nucleic acid sequence is then amplified in order to produce an amplified product, and the Tm value of the amplified product (e.g., amplicon) is determined using conventional melting curve analysis. The melting curve analysis is then utilized to determine or compute new primers or primer sets for use in the amplification of the target nucleic acid.

The determined or computed primers are then designed with primer Tm values within the range of the melting peak generated by the melt of the amplified product. The primers are then prepared or synthesized to have the designed primer Tm values.

DFA Primer Design—Oligonucleotide Chemical Modification

In some embodiments, primers can be configured to have a Tm that is within a narrow range of the Tm of the target nucleic acid by chemically modifying the oligonucleotides. Well known oligonucleotide synthesis chemistries may be used to increase the Tm values of the primers so they correspond to the temperature range of the Tm of the target nucleic acid. Such chemistries may use modified bases (e.g., Super G, A, T, C), LNA, or PNA, or other such oligonucleotide stabilizing chemistries. Also, additional oligonucleotide hybridization stabilizing chemistries may be developed that can be used for this application.

For example, primers synthesized with both conventional phosphodiester linkage chemistry, and LNA chemistries have been used to provide primer Tm values close to the Tm values of the target nucleic acid sequence. However, it is possible that certain target nucleic acids may have Tm values lower than that of the primers, and a hybridization destabilizing chemistry may need to be included to decrease the primer Tm values so that the primer Tm value is within a range of the Tm values of the target nucleic acid sequence.

DFA Primer Design—Melting Curve Analysis

In some embodiments, methods are provided for refining the design of the primers to minimize the temperature range for the specific amplification of the target nucleic acid sequence. As such, the target nucleic acid is amplified with standard reaction thermal cycling conditions to ensure the target nucleic acid sequence is amplified. The amplification is monitored using real-time PCR with a double-stranded DNA binding dye, such as SYBR, LCGreen, LCGreen+, Eva dye, or the like.

The amplified target nucleic acid is subjected to a melting curve analysis to determine the actual Tm value of the target nucleic acid sequence. The melting peak, which can be expressed as −dF/dT, is generated from melting the amplified target nucleic acid and can have a range similar to a distribution curve across a defined temperature range. At the low temperature end, the amplified target nucleic acid template is partially denatured. At the uppermost temperature the entire sample of amplified target nucleic acid is denatured. The temperature necessary to denature the target nucleic acid during the amplification procedure is within this temperature distribution.

Initially, the uppermost temperature is recommended to ensure more complete denaturation. Subsequently, the lowermost temperature of the distribution curve can be used as the initial Tm for a set of designed primers for use in amplification before any iterative changes are made to the primers.

Confirmation of the narrow temperature range that the initial primers may be used with can be performed either in serial or in parallel experiments of ever increasing annealing temperatures and ever decreasing denaturation temperatures to identify the set of ideal annealing and denaturation temperatures for any particular nucleic acid target.

Alternatively, the individual primers can be added to the amplified template and an additional melting curve analysis can be performed on the combined primer and template melting curves.

In any event, the Tm of the primers can be configured to overlap with a narrow temperature range that contains the Tm of the target nucleic acid sequence. The highest annealing temperature from these experiments where the target nucleic acid sequence is amplified specifically and efficiently can be considered the temperature which defines the optimal annealing temperature for the existing primers (e.g. primers that were tested). These same primers or slightly modified primers can then be resynthesized with additional hybridization stabilizing chemistries. Modifications to the primers to change the Tm in the desired direction so that the primer Tm overlaps with a narrow temperature range that contains the Tm of the target nucleic acid sequence. This can be accomplished using online design tools, such as the LNA design tool available from Integrated DNA Technologies. Such design tools can be used to estimate the number of necessary LNA modifications required to raise the Tm of the primer to better overlap with the melting curve of the target nucleic acid sequence.

In the instance the primer Tm values are greater than the highest melting temperature of the target nucleic acid sequence, it may be necessary to redesign the primers to have a lower Tm. Alternatively, the quantity of divalent and/or monovalent cation salts or other destabilizing agents (e.g., AgCI, DMSO, etc.) that are used in the amplification protocol (e.g., PCR) may be reduced to destabilize the hybridization of these oligonucleotides to the template. In any event, a reduction in the primer Tm may be needed in some instances.

DFA Primer Design—GC Content Modification

In some embodiments, the primer Tm can be modified by altering the GC content of the primer sequence. By changing the GC content, the primer Tm can be selectively changed. Usually, increasing the GC content can increase the Tm, and decreasing the GC content can decrease the Tm. However, there are instances that a high GC content is desired that will overly increase the Tm. In such instances, destabilizers can be used to enable the inclusion of high GC content primers or for the use of high GC content target nucleic acid sequences. The de-stabilizers can selectively decrease the temperature of the amplification procedure. Examples of destabilizers include DMSO, AgCI, and others.

DFA Thermal Cycling Ranges

In some embodiments, the primers can be prepared so that the target nucleic acid amplification or enrichment protocols can be performed at minimized temperature differences during the thermal cycling. This allows the thermal cycling to be done within a narrow temperature range so as to promote the formation of a specific product.

One range of thermal cycling can be within about 15° C. of the target nucleic acid Tm, or within 10° C. of the target nucleic acid Tm, or within 5° C. of the target nucleic acid Tm, or within 2.5° C. of the target nucleic acid Tm, or within 1° C. of the target nucleic acid Tm or even substantially the same Tm as that of the target nucleic acid Tm.

In some embodiments, the thermal cycling conditions for the amplification of the target nucleic acid spans the range of the Tm peak+/−about 1° C. to 15° C. of the target nucleic acid sequence.

In some embodiments, the thermal cycling conditions for the amplification of the target nucleic acid spans the range of the Tm peak+/−about 1° C. to 10° C. of the target nucleic acid sequence.

Or, in some embodiments, the thermal cycling conditions for the amplification of the target nucleic acid spans the range of the Tm peak+/−about 1° C. to 5° C. of the target nucleic acid sequence.

In some embodiments, the thermal cycling conditions for the amplification of the target nucleic acid spans the range of the Tm peak+/−about 5° C. to 15° C. of the target nucleic acid sequence.

In some embodiments, the thermal cycling conditions for the amplification of the target nucleic acid spans the range of the Tm peak+/−about 5° C. to 10° C. of the target nucleic acid sequence.

In some embodiments, the thermal cycling conditions for the amplification of the target nucleic acid spans the range of the Tm peak+/−about 5° C. of the target nucleic acid sequence.

In some embodiments, the thermal cycling conditions for the amplification of the target nucleic acid spans the range of the Tm peak+/−about 2.5° C. of the target nucleic acid sequence.

Such narrow temperature ranges make it possible to amplify specific target nucleic acids without thermal cycling between temperatures corresponding to the normal stages of PCR amplification (denaturation, annealing, and extension).

Also, it makes it possible to perform amplifications and enrichments in commercial temperature-controlled instruments that can be set at selected temperatures or be varied within narrow temperature ranges, such as an oven, heating block, or the like.

Figure 3:
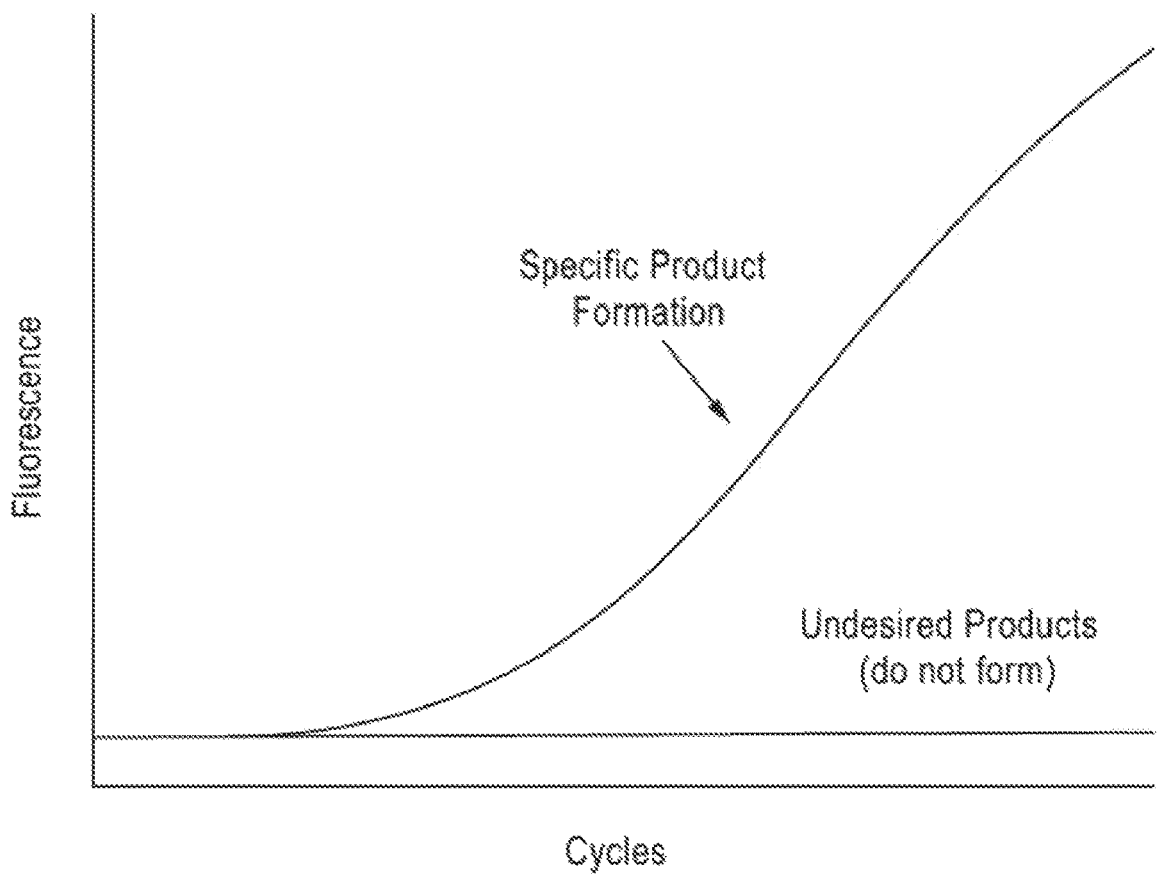
FIG. 3 is a graph showing high temperature PCR amplification of the same template used in FIG. 2.

FIG. 3 illustrates the graph of a narrow temperature range PCR amplification with the same target nucleic acid sequence as shown in FIG. 2, but FIG. 3 shows more specific product formation and less undesired products are formed.

In some embodiments, the temperatures of the thermal cycling can be selected in a narrow temperature range to substantially limit amplification to amplifying the target nucleic acid sequence. As such, the thermal cycling conditions can be modified to amplify the target nucleic acid sequence by modifying the annealing temperature to be substantially the same as the lower temperature base of the melting peak for the amplicon. Also, the thermal cycling conditions can be modified to amplify the target nucleic acid sequence by modifying the annealing temperature to be substantially the same as the higher temperature base for the melting peak of the amplicon.

In some embodiments, the primer Tm can be selected so that the amplification of the target nucleic acid can be performed at a temperature that ranges between about 75° C. to about 90° C. Such a temperature range, or narrowed 5° C. to 10° C. range therein, can be used for the amplification of DNA and/or RNA target nucleic acid sequences to reduce the formation of non-specific products during the amplification (e.g., PCR) process.

In some embodiments, the primer Tm can be selected so that the amplification is performed at isothermal amplification conditions in the Tm range of the target nucleic acid sequence to ensure appropriate product formation.

In some embodiments, the present disclosure includes a method of designing a primer set having a Tm with a target nucleic acid that is within a narrow range from the Tm of the target nucleic acid sequence. As such, the primer set can be designed so that the primer Tm overlaps the distribution curve of the Tm of the target nucleic acid sequence. For example, the primer set can be used in real-time PCR assays so that the primer Tm overlaps the distribution curve of the Tm for the target nucleic acid sequence so that a narrow temperature range can be used to amplify the target nucleic acid sequence.

DFA pH Modification

In some embodiments, the conditions of the protocol for amplifying the target nucleic acid sequence can be modified to an appropriate pH to increase the specificity of selectively amplifying the target nucleic acid over other nucleic acids. As such, the use of an appropriate pH can increase the ability to selectively amplify the target nucleic acid sequence. This can include the use of an amplification buffer that can enable the activation of chemically inactivated thermal stable DNA polymerases. Also, adjusting the pH with selected amplification buffers can allow for the amplification protocol to be performed at reduced temperatures, such as those temperatures ranges that have been recited herein.

In some embodiments, the pH of the amplification buffer can be adjusted so as to allow for the conversion of a chemically inactivated enzyme to the activated state. As such, an enzyme may be activated in a slightly acidic condition; however, basic pH values may be used for some enzymes. For acid-activated enzymes, standard Tris-based PCR buffers can have significant temperature dependence (e.g., reducing by 0.028 pH units per degree C.). Complete activation of the enzyme (e.g., chemically inactivated thermal stable DNA polymerase) from the inactivated state can require the pH to be less than about 7, more preferably less than about 6.75, and most preferably less than 6.5.

In some embodiments, the amplification protocol includes the use of lower pH buffers so that the amplification can be performed at lower activation temperatures. For example, for every 10° C. below 95° C., the enzyme activation temperature can be lowered by 0.3 pH units. However, limits to this approach are entirely a function of the dye chemistry used for the real-time detection of the amplified template (e.g., Fluorescein-based detection has significantly reduced fluorescence below pH 7.3).

DFA Modulation of Amplicon Size

In some embodiments, the design of the primers and/or amplification conditions can be modulated so as to modulate the size of the target nucleic acid sequence being amplified. This can include modulating the design of the primers and/or amplification conditions so that the size of the amplicon is significantly larger than that of the combined primers only. This can include the amplicon being 1-3 nucleotides longer than the primers, or 2 times larger than the primers, or 5 times larger than the primers, and more preferably 10 times larger than the primers.

DFA Arrays

In some embodiments, the primers designed as described herein can be employed in an array of amplification procedures with different concentrations of starting material. That is, the starting material can be partitioned into an array at varying concentrations, and the primers can be used therewith for the narrow temperature amplification protocol as described herein.

The use of the primers and narrow temperature amplification protocol with an array of varying concentrations of starting material can be used for quantification of the amount of target nucleic acid in the starting material.

Figure 4:
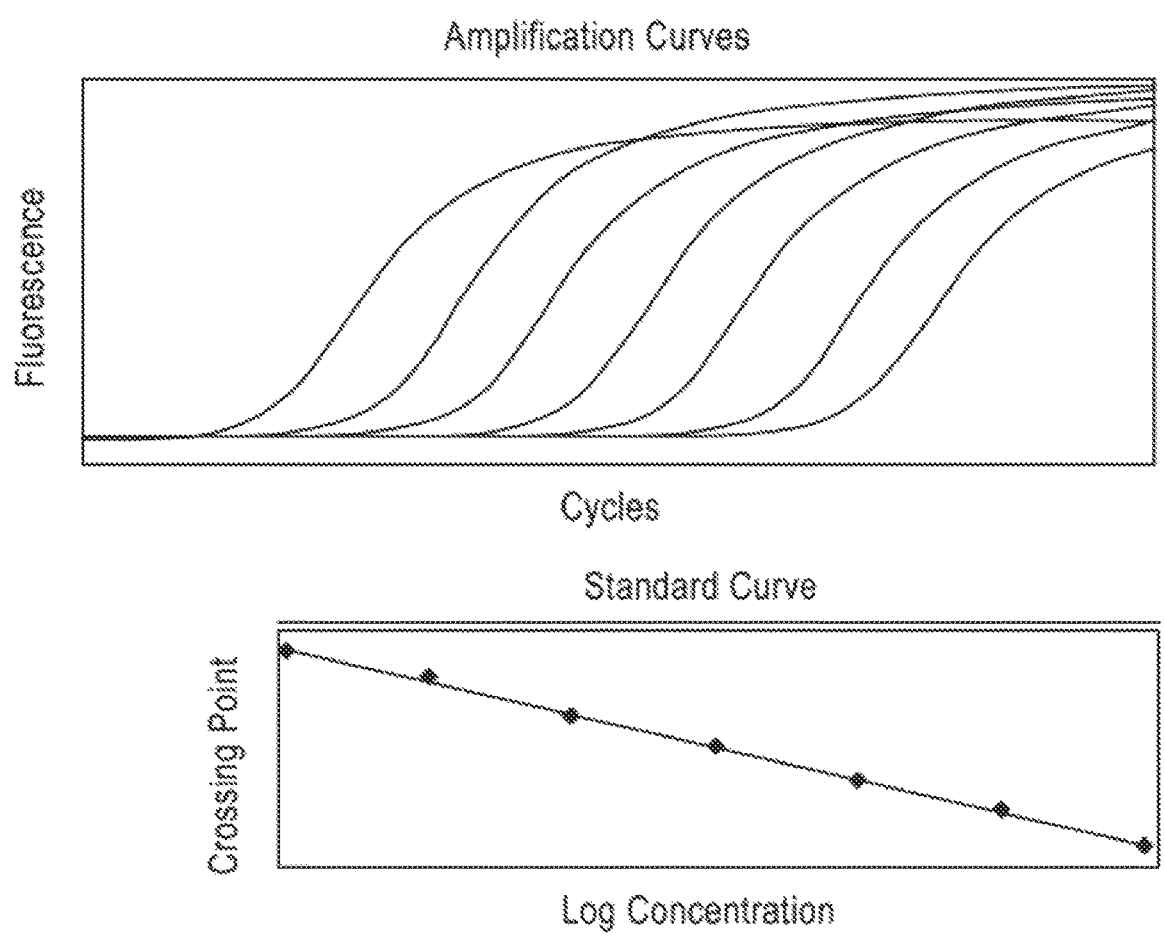
FIG. 4 is a graph showing the HTPCR amplification of the same template material using different starting material concentrations.

FIG. 4 is a graph that shows the use of the primers and protocol with an array of varying concentrations of starting material so that the amount of target material can be quantified.

Target Nucleic Acid Amplification Enrichment

In some embodiments, methods provided herein include a step of amplifying or enriching the target nucleic acid. Such a method can include a procedure substantially similar to well known methods of whole genome amplification and whole transcriptome amplification.

This can include amplifying a genome with a genome library generation step, which can be followed by a library amplification step. Also, the library generating step can utilize the specific primers or mixtures of the specific primers described herein with a DNA polymerase or Reverse Transcriptase. The specific primer mixtures can be designed with the primers so as to eliminate ability to self-hybridize and/or hybridize to other primers within a mixture, but allow the primers to efficiently and frequently prime the target nucleic acid sequence, wherein the primers can be designed as described herein.

In some embodiments, methods are provided for simultaneously determining a genetic expression profile for an individual member of a species relative to an entire standard genome for the species. The methods can comprise distributing a liquid sample of genomic material into an array of reaction chambers of a substrate. The array can comprise a primer set and a probe for each target nucleic acid sequence along the entire standard genome. The liquid sample can comprise substantially all genetic material of the member. Each of the reaction chambers can comprise the primer set and the probe for at least one of the target nucleic acid sequences and a polymerase. The methods can further comprise amplifying the liquid sample in the array, detecting a signal emitted by at least one of the probes, and identifying the genetic expression profile in response to the signal.

Using this directly lysed DNA sample and combining it with reaction ingredients similar to those used in whole genome amplification procedures enables the dynamic opening and closing of a nucleotide that has been referred to as "breathing" or "flux," of complementary nucleic acids. This flux enables access by and binding by, specific primers and probes only, as only those regions in flux can be interrogated by the primers or probes. This, in turn, makes it so the amplification is wholly specific and subsequently the formation of non-specific products (NSP) is substantially eliminated.

The DFA technique has been validated against a variety of DNA templates, and it has been determined that DFA works over a broad range of G+C content templates from 30-66%, where the DFA technique performed comparably in sensitivity to PCR and without the formation of non-specific products (NSPs). DFA has been adapted to the following detection techniques: real-time PCR (dsDNA binding dye), gel-electrophoresis, chemiluminescence, colorimetric, and ELISA.

Primer and Tag for Specific Amplification of a Target Nucleic Acid

Figure 5:
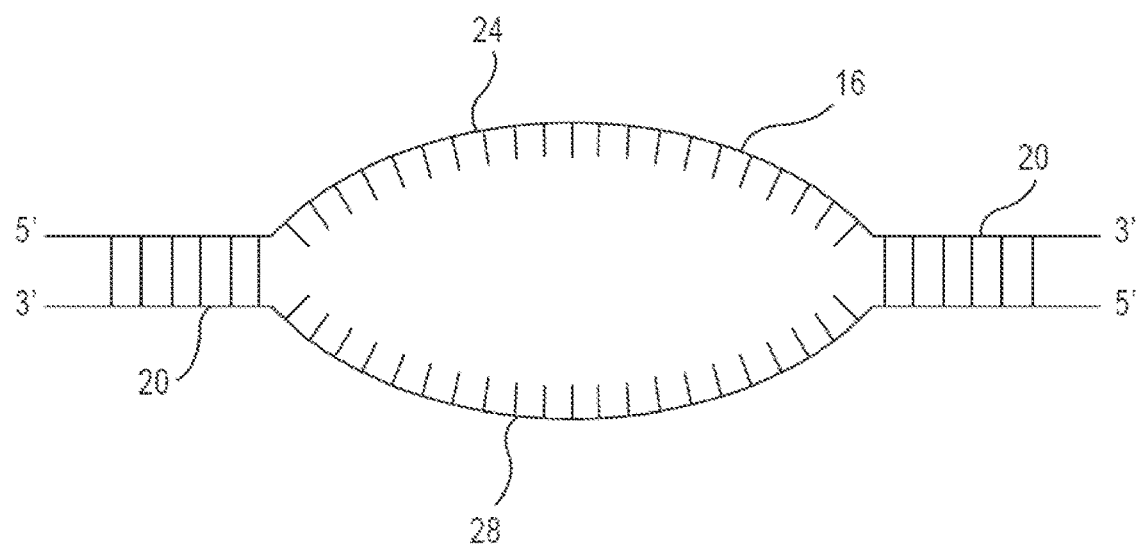
FIG. 5 depicts the creation of a "bubble" 16 as the reaction is heated to a temperature approaching the denaturation temperature of the target sequence.

The following relates to a method for the rapid amplification of a nucleic acid sequence that significantly inhibits the extension of the reaction beyond the target sequence, as well as allows for existing amplification primers to be modified in order to narrow the thermal cycling temperature range required to generate a specific target amplicon or amplicons. As depicted in FIG. 5, the method implements the creation of a "bubble" 16 as the reaction is heated to a temperature approaching the denaturation temperature of the target sequence. Assuming that the denaturation temperature, or the initiation of target sequence denaturation at or near the Tm, of the target sequence is less than the denaturation temperature of the sequences 20, that are adjacent to or near the end of the target sequence, the adjacent sequences 20 will remain double stranded, resulting in a "bubble 16" forming in the DNA strand as the target sequence denatures. This bubble will include the target sequence and possible sequences beyond the target sequence, depending on the denaturation temperatures of the sequences proximate to the target sequence. In the bubble 16, a length of one half strand of DNA 24 has separated from a length of its complementary strand of DNA 28 while the adjacent sequences 20 remain annealed or substantially more hybridized than the target sequence.

Figure 6:
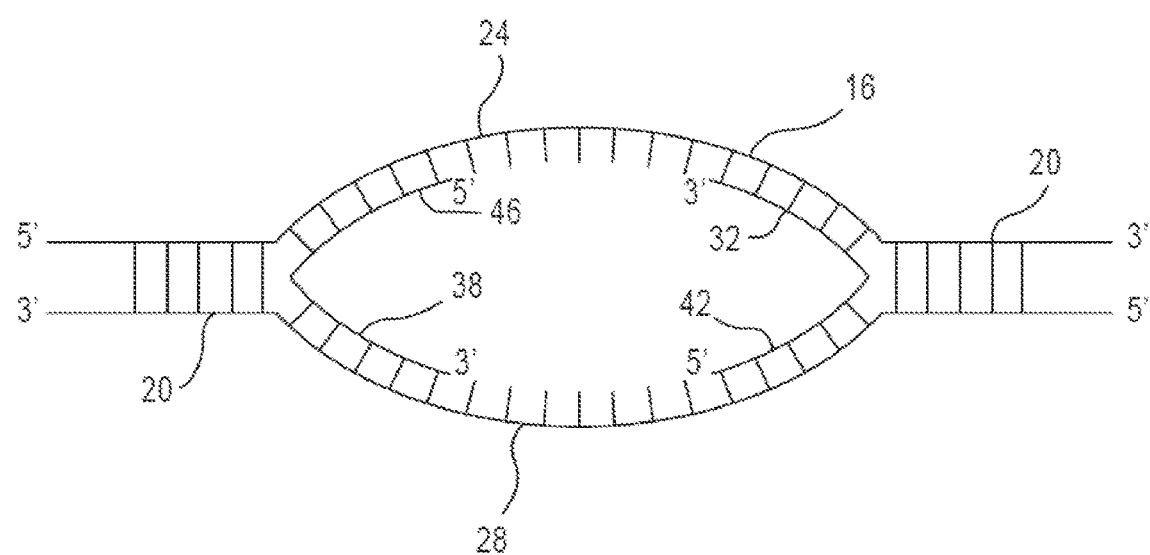
FIG. 6 depicts the bubble 16 having a first primer 32 annealed to DNA strand 24 at one end of the bubble. Primer 32 has a first blocking tag 42 that anneals to the complementary DNA strand 28. A second primer 38 is annealed to DNA strand 28 at the other end of the bubble. Primer 38 has a second blocking tag 46 that anneals to the complementary DNA strand 24.

FIG. 6 depicts the bubble 16 having a first primer 32 annealed to the first strand of DNA 24. A second primer 38 is annealed to the second strand of DNA 28. A first blocking tag 42 has been added to the first primer 32. The first blocking tag 42 comprises an oligonucleotide sequence that is complementary or substantially similar, as the design of this tag 42 will contain variable lengths and potentially nucleotide or backbone modifications to optimize the annealing of the tag 42 to the opposite strand 28 target region terminus, to the portion of the second DNA strand 28 that is complementary to the portion of the first DNA strand 24 that is annealed to the first primer 32. This arrangement causes blocking tag 42 to anneal to the portion of the second DNA strand 28 that is complementary to the first DNA strand 24 that is annealed to the first primer 32. A second blocking tag 46 has been added to the second primer 38. The second blocking tag 46 comprises an oligonucleotide sequence that is complementary to the portion of the first DNA strand 24 that is complementary to the portion of the second DNA strand 28 that is annealed to the second primer 38. This arrangement causes the second blocking tag 46 to anneal to the portion of the first DNA strand 24 that is complementary to the second DNA strand 28 that is annealed to the second primer 38. The use of blocking tags in this manner inhibits the extension of the reaction beyond the bubble 16 by essentially sealing off the bubble 16 from the adjacent sequences 20.

Figure 7:
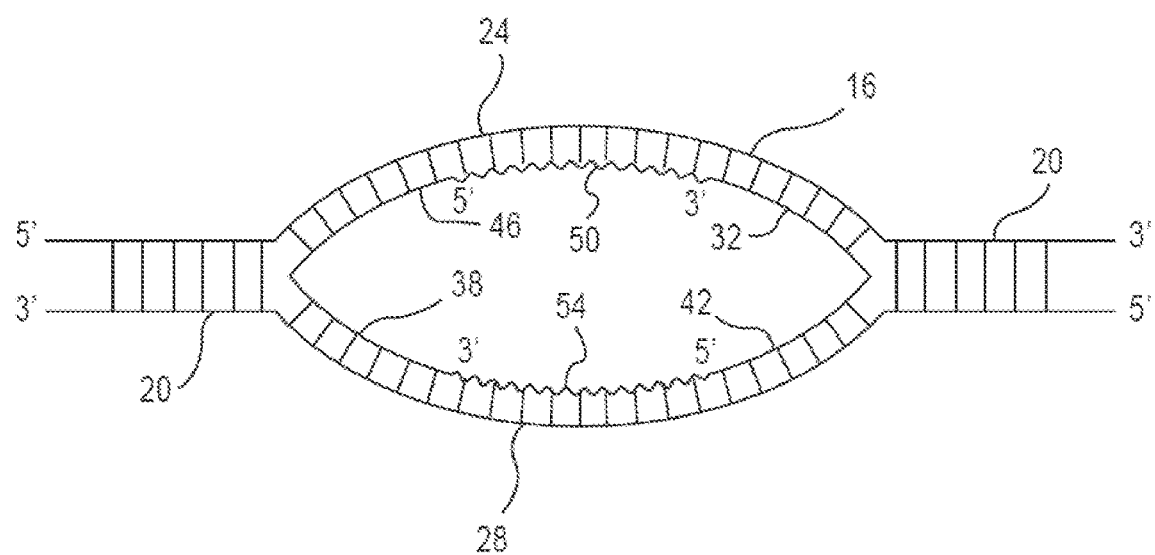
FIG. 7 depicts the extension phase of the amplification using the primer with blocking tag. The first primer 32 has been extended in the direction of the second blocking tag 46, resulting in an extension 50 which cannot readily extend beyond the second blocking tag 46. Similarly, the second primer 38 has been extended in the direction of the first blocking tag 42, resulting in an extension 54 which cannot readily extend beyond the first blocking tag 42.

FIG. 7 depicts the extension phase of the reaction. The first primer 32 has been extended in the direction of the second blocking tag 46. The first primer 32 which forms the extending sequence in the direction of the 5' end of the tag 46 from the opposite strand primer 32 cannot readily extend beyond the second blocking tag 46. This results in a shorter extension 50 than would otherwise exist in the absence of the blocking tag 46. Similarly, the second primer 38 cannot readily extend beyond the first blocking tag 42, again resulting in a shorter extension 54 than would otherwise exist. The blocking tags 42 and 46 may comprise cleavable chemistries in order to inhibit the tags 42 and 46 from being cleaved by the polymerase as it extends.

Figure 8A:
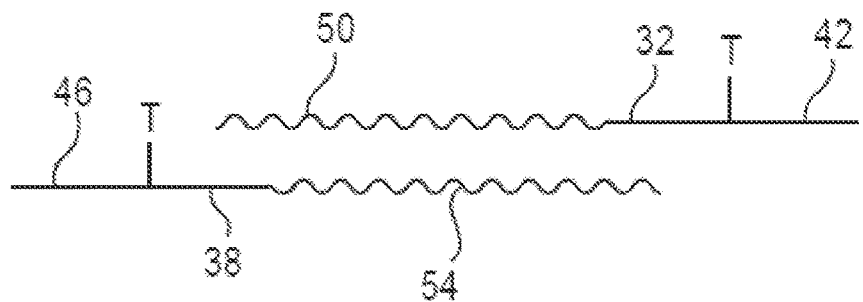
FIG. 8A-8C depicts the second cycle of amplification using the primers with blocking tags.

FIG. 8A depicts the two extension products from the first cycle of amplification. The point at which the tag (either tag 42 or tag 46) transitions to the primer (either primer 32 or primer 38) is designated by a T, to denote a transition. The transition is the transition between the primer and the tag. The transition can be a single nucleotide, a chain of carbons, a multifunctional moiety (such as Epochs tri-functional linker), or modified nucleotides or backbones. The transition can also be a fluorophore, an MGB or any chemical or combination of chemicals known to those skilled in the art. The transition can be positioned at a point that holds the hydrogen bond together at the end of the bubble. The tag blocked nascent formed products from the first cycles of the thermal cycling reaction will have only partial complementarity with any fresh primers that anneal in the subsequent cycle until the complete product with primer and tag is completely synthesized.

Figure 8B:
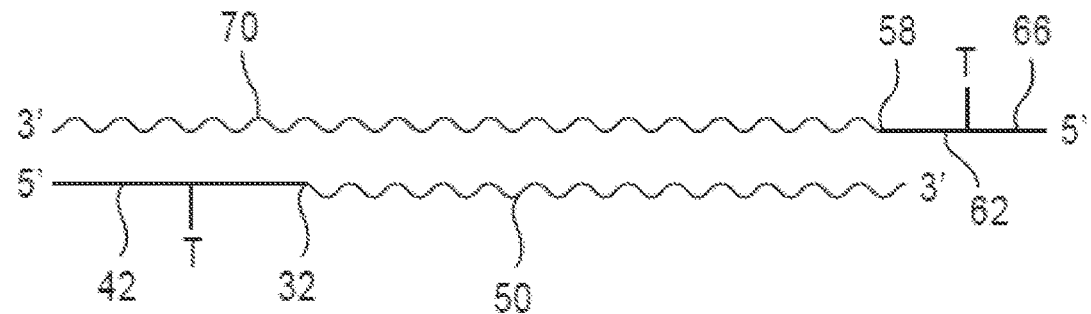
Figure 8C:
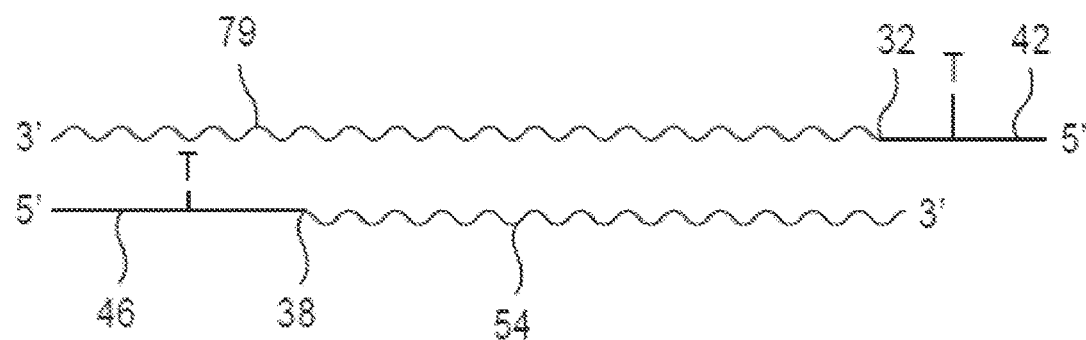

FIG. 8B depicts a fresh primer 58 that has annealed to the end of the first extension 50. Because the first extension 50 did not extend all the way to the end of the bubble, it did not replicate the complete complement to the fresh primer 58. As a consequence, only part of the fresh primer 58 anneals to the first extension 50, resulting in an "overhang 62" of unannealed primer. The fresh primer 58 comprises a tag 66 (note that fresh primer 58 and tag 66 is equivalent to primer 38 and tag 46 in sequence). The fresh primer 58 extends the length of the first primer 32 and its tag 42 to form a third extension 70 that forms a complete complimentary copy of the first tag 42, the first primer 32 and the first extension 50. Because this second extension 70 appends from the fresh primer 58 and its tag 66, it forms a complete copy of the target sequence plus the two tags appended to the ends of the primers. Likewise, the opposite strand with extension 54 will hybridize to a fresh primer (32-T-42), and the extension of primer 32 and tag 42 creates the extension 79 of that strand (FIG. 8C).

Figure 9:
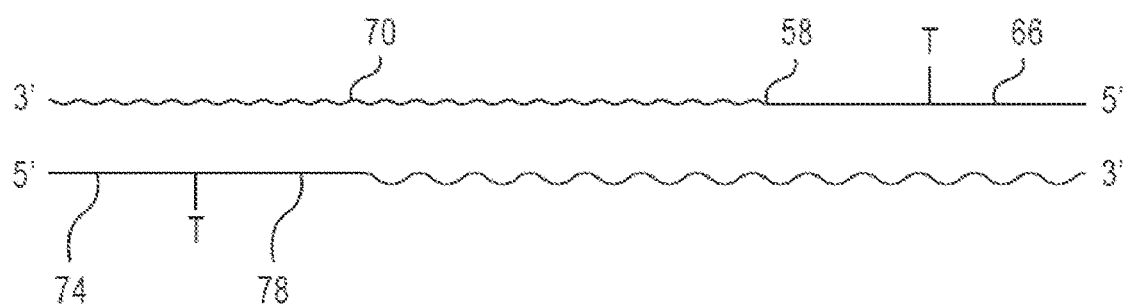
FIG. 9 depicts the third cycle of amplification using the primers with blocking tags. With the extension 70 product as template, primer 78 comprising tag 74 anneals to the 3' end of extension 70 and amplification results in another complete copy of the target sequence plus the tags 74 and 66 on both ends of the target sequence.

FIG. 9 depicts a tag 74 and primer 78 complementary to the sequence of the third extension 70. Because the tag 74 and primer 78 have a complete complement in the third extension 70, the entire tag and primer 78 anneals to the third extension 70 (note that primer 78 and tag 74 is equivalent to primer 32 and tag 42 in sequence). The primer 78 then extends to the end of the tag 66 completing another complete copy of the target sequence plus the tags.

Because the primers do not achieve full extension on cycle 1, the primers do not have a complete binding site on cycle 2. This results in the annealing temperature for the cycle 2 potentially being different and most likely lower. With nucleotide modifications the Tm of the first primer 32 may be adjusted to ensure sufficient annealing of its 3' most portion to the nascent formed partial product which is truncated in length as a function of the 'blocking' of the sequence by the presence of the opposite strand tag and, subsequently, will vary in temperature from the complete first primer (32). The low temperature or high temperature and the ramp rate between temperatures may be adjusted to be completely different to accomplish design objectives of the designed test temperature for cycle 2 than the annealing temperature for cycle 1. Once complete extension of the primer, tag and target sequence is achieved in cycle 2, the annealing temperatures of the subsequent cycles may be higher or lower, or the rate of annealing could be modified than the annealing temperature would be if the primers were used without the tags, though again with nucleotide modifications, the Tm of the fully annealed oligonucleotides may be adjusted to limit the effect of the longer annealed sequence. Thus, to accommodate these features of the products of the method, it is sufficient to change the annealing temperature to allow the formation of amplification product and the matching portion of the primer sufficient thermal stability to anneal and initiate the polymerization reaction at the first few cycles of the reaction. At a minimum, a single cycle of lowered annealing temperature is necessary. In this way, the Tm of the primer can be adjusted in relationship to the Tm of the target nucleic acid sequence. The theoretical Tm of the primer can be determined beforehand using online design tools, such as the LNA design tool available from Integrated DNA Technologies. Such design tools can be used to estimate the number of necessary LNA modifications required to raise the Tm of the primer to better overlap with the melting curve of the target nucleic acid sequence. In the instance the primer Tm values are greater than the highest melting temperature of the target nucleic acid sequence, it may be necessary to redesign the primers to have a lower Tm. In some embodiments, the primer Tm can be modified by altering or selecting particular % GC regions of a target template to be a primer sequence. By changing the % GC, the primer Tm can be selectively changed to fit better within the thermal cycling range for optimal DFA performance. Usually, increasing the % GC can increase the Tm, and decreasing the % GC can decrease the Tm. However, there are instances that a high % GC is desired that will overly increase the Tm. In such instances, destabilizers can be used to enable the inclusion of high % GC content primers or for the use of high % GC target nucleic acid sequences. The de-stabilizers can selectively decrease the temperature of the amplification procedure. Examples of destabilizers include DMSO, AgCI, and others.

Attention to the design of the additional tag appended to the template may raise the temperature of the nascent target sequence, the denature temperature of the template, though it could be designed to lower the temperature of the nascent target sequence, the denature temperature of the template. Overall, the reaction should conform to the following relationship between the Tm of the template and the Tm of the primer: The difference between the Tm of the template with the tag appended and the Tm of the template without the tag is less than the difference between the Tm of the primer with the tag appended and the Tm of the primer without the tag. This means that, while the Tm of the template will tend to increase by some amount as a result of the addition of the tag, the Tm to the primer will tend to increase by a larger amount as a result of the addition of the tag. This results in a net narrowing of the thermal cycling conditions for the reaction. An example of one thermal profile is as follows:

1 or more cycles of 88° C.–75° C. (Δ13° C.)
1 or more cycles of 88° C.–70° C. (Δ18° C.)
1 or more cycles 89° C.–78° C. (Δ11° C.)

Hence, a hypothetical cycling temperature would look something like the following:

| | Denaturation Temperature | Annealing Temperature |
| --- | --- | --- |
| Cycle 1 | 88° C. | 75° C. |
| Cycle 2 | 88° C. | 70° C. |
| Cycle 3 | 89° C. | 78° C. |

By cycle 3, the denaturation temperature of the template has increased 1° C. and the annealing temperature of the primer with tag has increased 3° C. over the initial annealing temperature.

See Example 1 for exemplary primers and tags for amplification of a target sequence.

Figure 10:
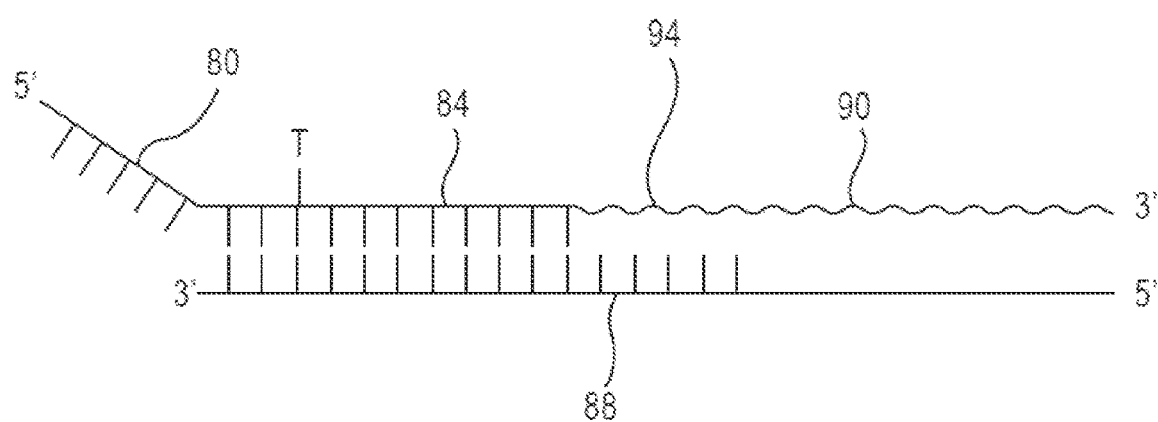
FIG. 10 depicts the first cycle in an amplification using a primer comprising a tag with an arbitrary sequence. A tag 80 is appended to a primer 84. The tag 80 does not correspond to any DNA strand adjacent to the target sequence 88 sequence, but rather, represents a more or less arbitrary oligonucleotide sequence. In the first cycle, the primer 84 binds to the target sequence 88 and extends fully across the target sequence 88, creating an oligonucleotide 94 comprising the primer 84, the extension 90 and the tag 80. In the first cycle, the tag 80 does not bind to the target sequence 88.
Figure 11:
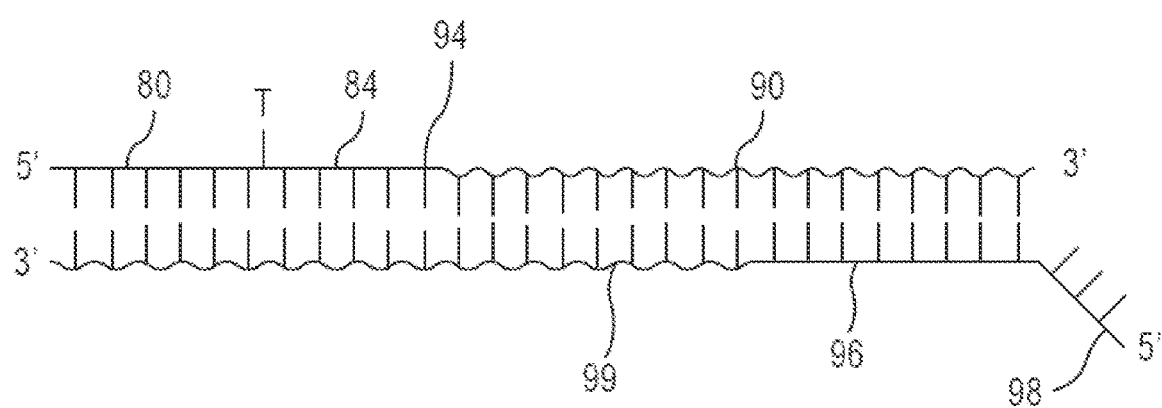
FIG. 11 depicts the second cycle in an amplification using a primer comprising a tag with an arbitrary sequence. In the second cycle, the oligonucleotide 94 binds to a fresh primer 96 and tag 98. The fresh tag 98 has no complementary sequence on the oligonucleotide 94 to bind to. The primer 96 extends all the way to the end of the oligonucleotide 94, creating a duplicate oligonucleotide 99 comprising a reproduction of the tag 80, primer 84, and the extension 90 of the oligonucleotide 94. This duplicate oligonucleotide comprises a duplicate of the tag 80 on one end and its own tag 98 on the opposite end.

In another embodiment, depicted in FIG. 10, a tag 80 is appended to a primer 84. In this embodiment, the tag 80 does not correspond to any DNA strand adjacent to the target sequence 88 sequence, but rather, represents a more or less arbitrary oligonucleotide sequence. The arbitrary oligonucleotide sequence is designed such that it will not react with any other oligonucleotide sequence in the reaction. In the first cycle, the primer 84 binds to the target sequence 88 and extends fully across the target sequence 88, creating an oligonucleotide 94 comprising the primer 84, the extension 90 and the tag 80. In the first cycle, the tag 80 does not bind to the target sequence 88. In the second cycle, depicted in FIG. 11, the oligonucleotide 94 binds to a fresh primer 96 and tag 98. The fresh tag 98 has no complementary sequence on the oligonucleotide 94 to bind to. The primer 96 extends all the way to the end of the oligonucleotide 94, creating a duplicate oligonucleotide 99 comprising a reproduction of the tag 80, primer 84, and the extension 90 of the oligonucleotide 94. This duplicate oligonucleotide comprises a duplicate of the tag 80 on one end and its own tag 98 on the opposite end.

Figure 12:
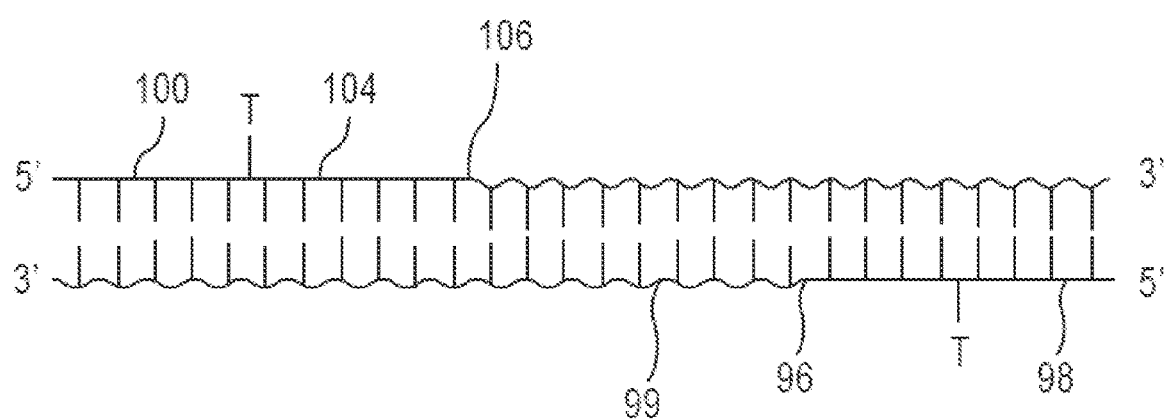
FIG. 12 depicts the third cycle in an amplification using a primer comprising a tag with an arbitrary sequence. In the third cycle, a fresh tag 100 and primer 104 binds to the duplicate oligonucleotide 99 (note that fresh primer 104 and tag 100 is equivalent to primer 84 and tag 80 in sequence). The primer extension 106 extends all the way to the end of the tag 98, creating a complete duplicate.

FIG. 12 depicts the third cycle of this method. In the third cycle, a fresh tag 100 and primer 104 binds to the duplicate oligonucleotide 99 (note that fresh primer 104 and tag 100 is equivalent to primer 84 and tag 80 in sequence). The primer extension 106 extends all the way to the end of the tag 98, creating a complete duplicate.

In another embodiment, the addition of a tag to a primer to promote the formation of a bubble structure and simultaneously serve the role of blocking the extension of the nascent amplified strand beyond the bubble is accomplished by the incorporation of naturally occurring stretches of 3 or more Cystosine residues adjacent, or may have 0 or a few bases between, to Guanosine residues.

These stretches can be used to form Guanosine quadruplex structures that will hold the DFA bubble together and prevent the elongation of the nascent amplified strand beyond the bubble.

Figure 13:
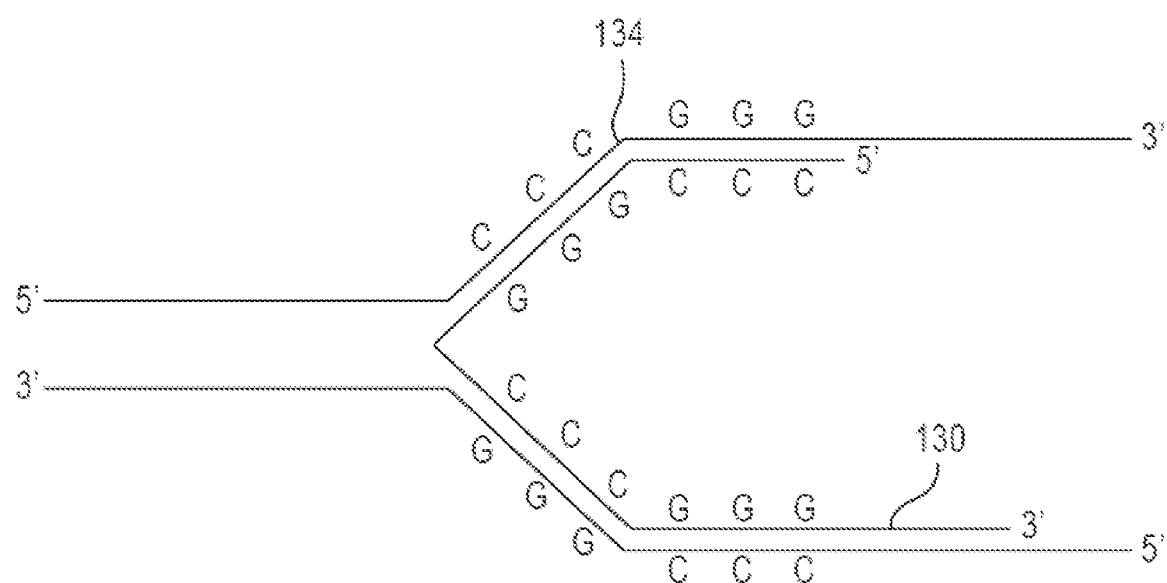
FIG. 13 depicts the initial stage of one mechanism for the formation of a G-quadruplex. In this mechanism, a primer 130 is designed to interface with one end of the target bubble 134, wherein the bubble comprises principally GC sequences. The primer 130 is designed with GC sequences to complement the target's GC sequences.
Figure 14:
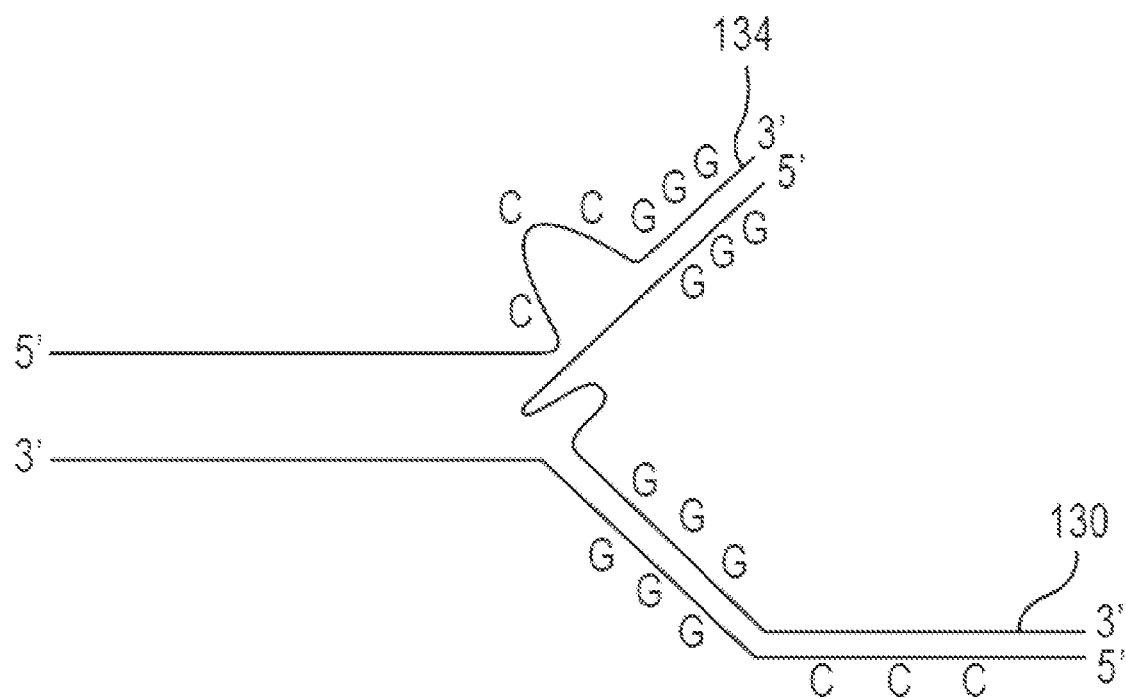
FIG. 14 depicts unconventional hybridization of Gs to Gs to form Hoogsteen pairs in areas comprising high GC content such that G quadruplexes are formed through a process of folding the strands to line the Gs up with Gs.
Figure 15:
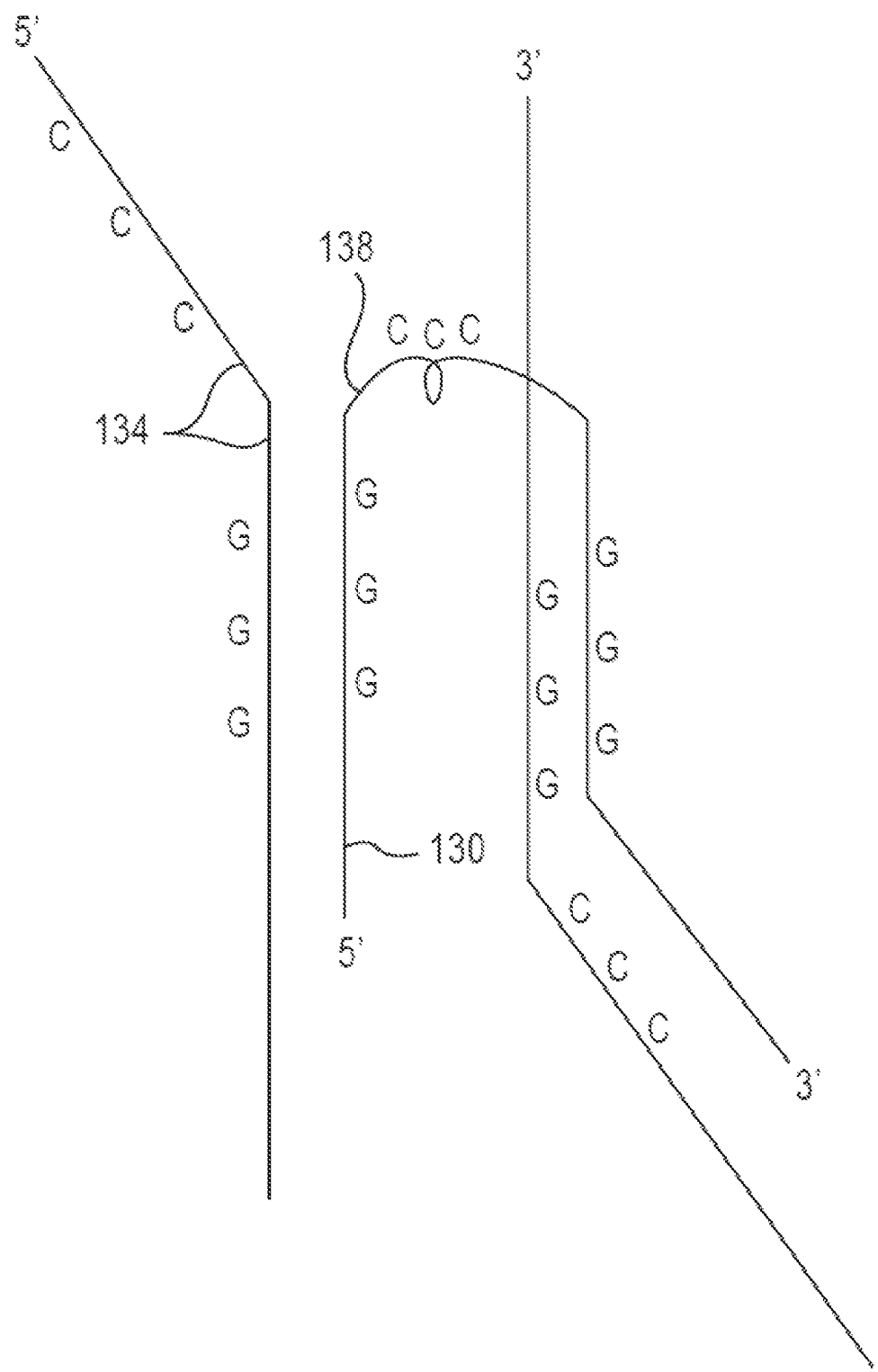
FIG. 15 depicts G quadruplex formation. The displaced C sequence 138 is not bound to any complementary sequence in the target and so twists into a folded shape that serves as a solid blocker to any extension of the primer past the bubble.

G-quadruplexes can form a number of ways, as either separate parallel strands of G stretches, as intermolecular dimers, or as intramolecular folds. FIG. 13 depicts the initial stage of one mechanism for the formation of a G-quadruplex. In this mechanism, a primer 130 is designed to interface with one end of the target bubble 134, wherein the bubble comprises principally GC sequences. The primer 130 is designed with GC sequences to complement the target's GC sequences. However, because of the unconventional hybridization of Gs to Gs to form Hoogsteen pairs in areas comprising high GC content, areas with high GC content tend to form G quadruplexes through a process of folding the strands to line the Gs up with Gs as depicted in FIG. 14. This results in the G quadruplex formation depicted in FIG. 15. The displaced C sequence 138 is not bound to any complementary sequence in the target and so twists into a folded shape that serves as a solid blocker to any extension of the primer past the bubble.

Figure 16:
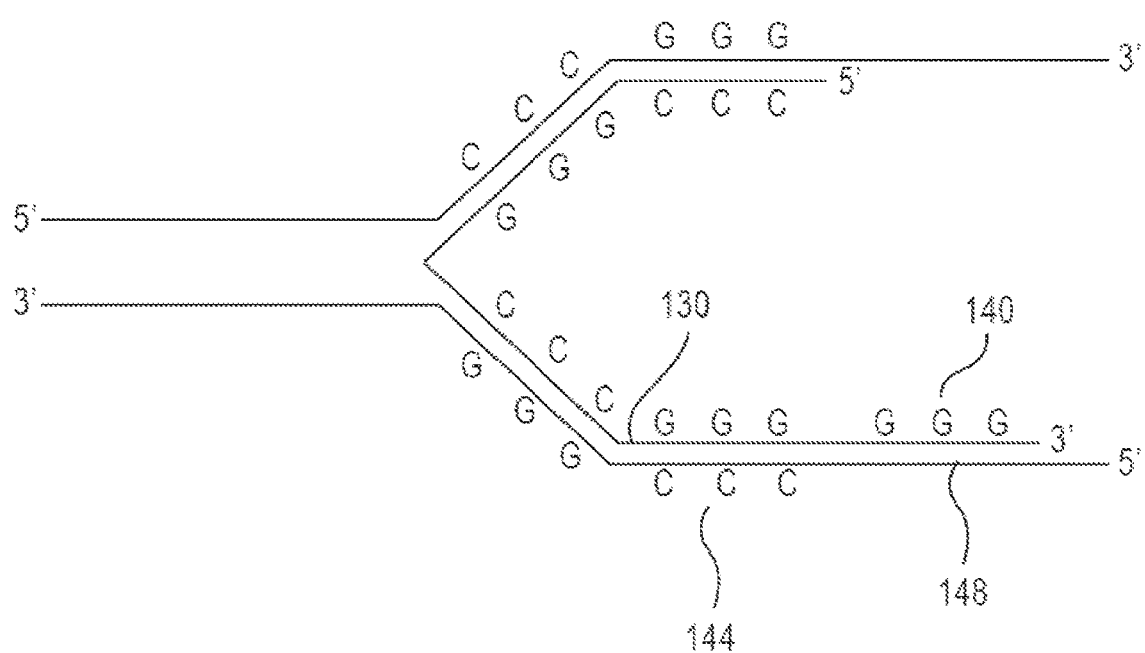
FIG. 16 depicts a sequence of G's 140 that is added internal to the primer, proximal to the 3' end and adjacent to the quadruplex forming region of the primer 130. This sequence of G's 140 is attracted to the sequence of C's 144 adjacent to it on the first strand of the target 148. This attraction gives added impetus to the primer to shift and thus form a G quadruplex.
Figure 17:
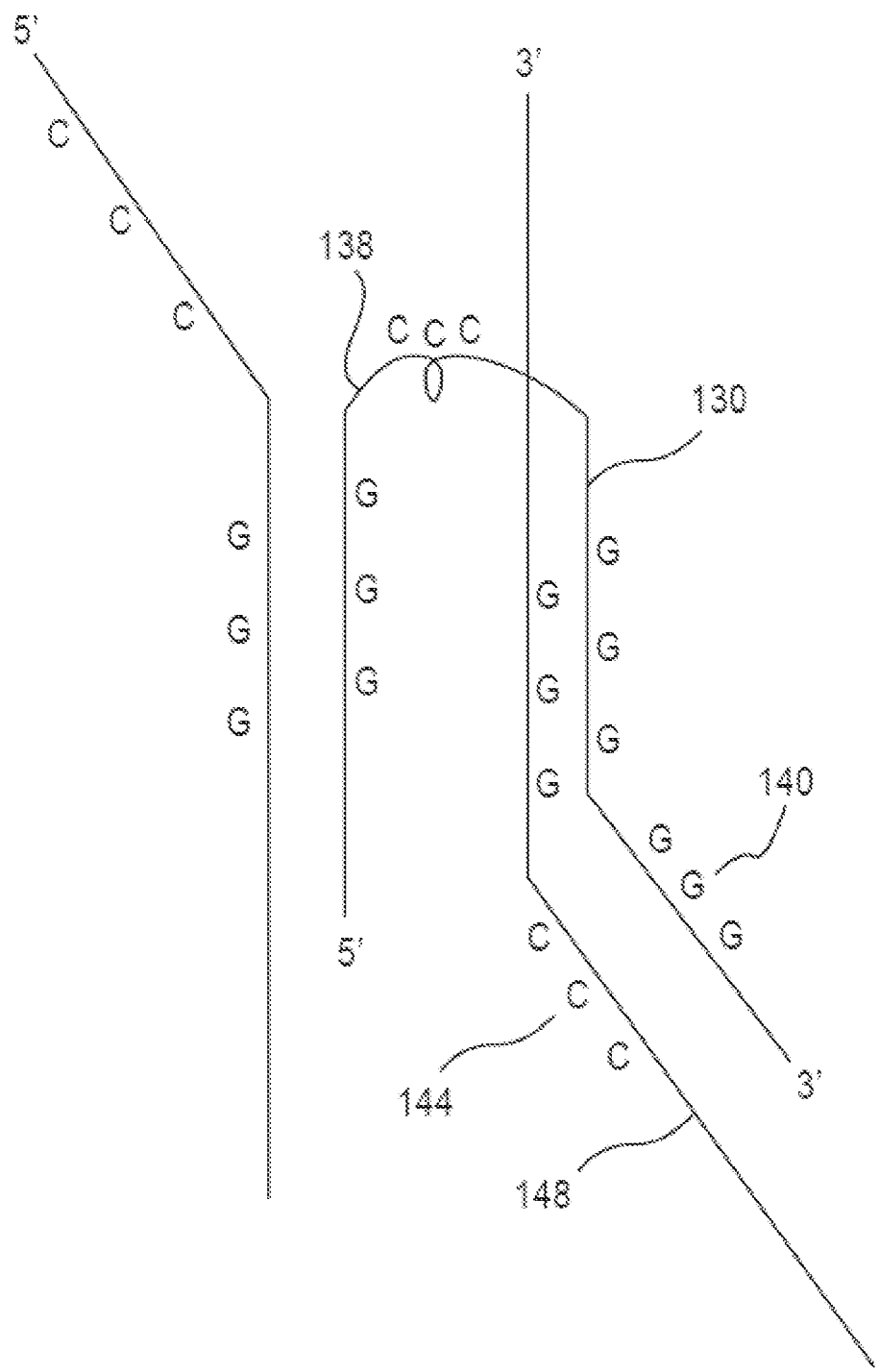
FIG. 17 depicts G quadruplex formation. The sequence of G's 140 has shifted to pair with the sequence of C's 144 on the first strand of the target 148. The displaced C sequence 138 is not bound to any complementary sequence in the target and so twists into a folded shape that serves as a solid blocker to any extension of the primer past the bubble.

In another embodiment, depicted in FIG. 16, a sequence of G's 140 is added internal to the primer, proximal to the 3' end and adjacent to the quadruplex forming region of the primer 130. This sequence of G's 140 is attracted to the sequence of C's 144 adjacent to it on the first strand of the target 148. This attraction gives added impetus to the primer to shift and thus form the G quadruplex as depicted in FIG. 17.

A method of modifying existing PCR oligonucleotide primers based on those embodiments in FIGS. 6-17 could be readily achieved by one skilled in the art of polymerase assay design.

Multiplex Amplification

PCR has traditionally been carried out in a single fairly wide thermal cycling range. Generally, the range is approximately between 60° C. and 90° C.-95° C. As a result of this practice, primer design in traditional PCR has only been concerned with designing a set of primers that correspond to the target sequence, without concern for the melting or annealing temperatures of the specific target, or amplicon. However, it has been observed that primers that correspond to different targets may possess different denaturation and annealing profiles depending on the relative GC and AT concentrations in the sequence in question. This observation, in turn, has led to the ability to design primers to thermal cycle within a specific temperature range, which, in turn, allows for thermal cycling within ranges that are narrower than the traditional 60° C. and 90° C.-95° C.

However, another consequence of being able to custom design target denaturation and primer annealing temperatures while simultaneously narrowing the thermal cycling range allows for amplification of different targets to be carried out in a single reaction vessel by thermal cycling the reaction vessel at different temperature ranges in succession. This ability has many potential applications, several of which are set forth below.

Next Generation Sequencing

Next Generation Sequencing is the term given to a process that sequences entire strands of DNA. Next Generation Sequencing utilizes PCR in its initial phase to amplify enough sample DNA to subsequently sequence. The PCR method used to amplify the sample DNA generally thermal cycles in a temperature range of between 95° C. and 60° C. In order for Next Generation Sequencing to perform optimally, the initial PCR amplification process should ideally amplify the entire genomic nucleic acid equally. However, conventional PCR cannot accomplish this. The PCR method used to amplify the sample DNA generally thermal cycles in a temperature range of between 95° C. and 60° C. Thus, for example, high % AT (low % GC) regions generally amplify most efficiently with annealing temperatures that are substantially less than 60° C. Because PCR generally is not conducted below 60° C. high % AT (low % GC) regions experience low amplification efficiencies with conventional PCR. Further confounding the target enrichment, high % AT (low % GC) regions also suffer from low recovery rate from the gel electrophoretic sizing processes. High % GC regions, on the other hand, experience low amplification efficiencies with conventional PCR due to their propensity to denature optimally best at temperatures above 95° C. Conventional PCR generally is not performed at temperatures above 95° C. The uneven amplification of various regions is known as enrichment bias. The enrichment bias problem cannot be readily solved by simply increasing the thermal cycling range to include temperatures above 95° C. and below 60° C. Such extreme ranges would tend to produce unacceptably high levels of non-specific product and require substantially greater genome coverage and data analysis to assemble the sequence information therein.

The problem of enrichment bias has, with PCR enrichment, therefore generally been dealt with by the use of molecular crowding agents that work to produce an average of the amplification efficiency for all template regions. Enrichment bias can also be ameliorated by using greater concentrations of high % AT (low % GC) and High % GC templates. Frequently, stabilizers such as TMAC are used to stabilize the high % AT (low % GC) regions. Destabilizers such as Betaine are used to destabilize the high % GC regions. Additionally, polymerases with a higher reaction efficiency such as Kapa Biosystems HiFi™ polymerase may also be employed to help smooth out amplification efficiency differences. These compensation methods are all somewhat effective in helping to alleviate enrichment bias. However, they all suffer from the drawback of unwanted side effects, including adding complexity and expense to the reaction. Template enrichment is best suited for PCR of approximately 200 base pair products or less. Short amplicons such as those ideally suited for enrichment with PCR require a greater number of reads to accurately cover an entire sequencing target region, be it a gene or an entire genome, and with such short read lengths the high number of data streams means the analysis of these sequencing results require long data processing times.

Thus, it would be useful to have a method for compensating for or eliminating enrichment bias that did not rely on adding additional chemistry to the amplification reaction.

It would also be useful to have a method for compensating for or eliminating enrichment bias that also produced greater amplicon length. For example, a process that creates amplicons of 400 base pairs in length would require half as many reads than a process that creates amplicons of 200 base pairs in length.

The following describes a method for amplifying a genomic sequence that reduces or eliminates compensation bias without the need to add additional chemistry to the reaction. The method is suitable for generation of amplicons of 400 base pairs or greater, reducing the number of reads required and shorter time to process and compile the sequencing data.

The method breaks the amplification process into two or more parts, each of which employs distinct thermal profiles. The disclosed method allows for thermal cycling in the specific temperature ranges that are most efficient for amplifying the target sequence(s) or representative % GC content region with the portion of the thermal profile designated for such target sequence or representative % GC content region. Other portions of the thermal profile may be designated for the amplification of other target sequence(s) or other % GC content region.

Figure 19:
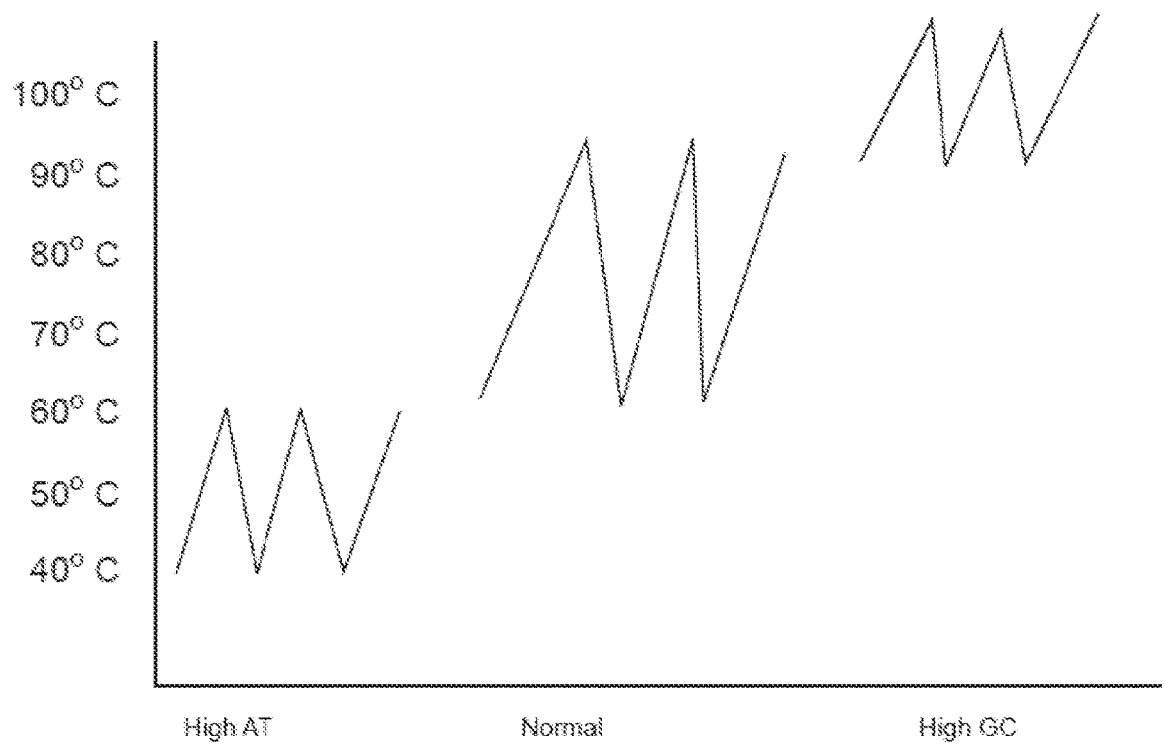
FIG. 19 depicts thermal profiles for amplification of high AT nucleic acid regions first, then normal nucleic acid regions (regions amplified by traditional PCR temperature ranges) second, and then high GC nucleic acid regions third.

In one embodiment, depicted in FIG. 19, primers that correspond to areas with high % AT (low % GC) content are designed to thermal cycle at temperatures at or below 60° C. Primers that correspond to areas with high % GC content are designed to thermal cycle at temperatures at or above 95° C. Finally, primers that are designed to thermal cycle within traditional PCR ranges are used to amplify the remaining areas.

The DNA would then be thermal cycled within each range in series. One exemplary thermal cycling profile for this assay would be: between 45° C. and 60° C. for as many cycles as necessary to generate a result; between 60° C. and 95° C. for as many cycles as necessary to generate a result; and between 95° C. and 99° C. for as many cycles as necessary to generate a result. This profile could vary by temperature and number of cycles, depending on the primer designs and the DNA being examined. For example, in one embodiment, the number of cycles varies from one temperature range to another. It also may be that specific temperature suitable polymerases are chosen for each temperature range of thermal cycling. The specific order of the thermal cycling profiles, from low to high, or high to low, can vary depending on the objectives and the target regions being enriched, amplified and ultimately sequenced. In addition, the method may also comprise a certain degree of overlap between the thermal cycling ranges. For example, a set of thermal cycling parameters might comprise 50° C.-65° C., 60° C.-95° C., and 90° C.-105° C.

Figure 20:
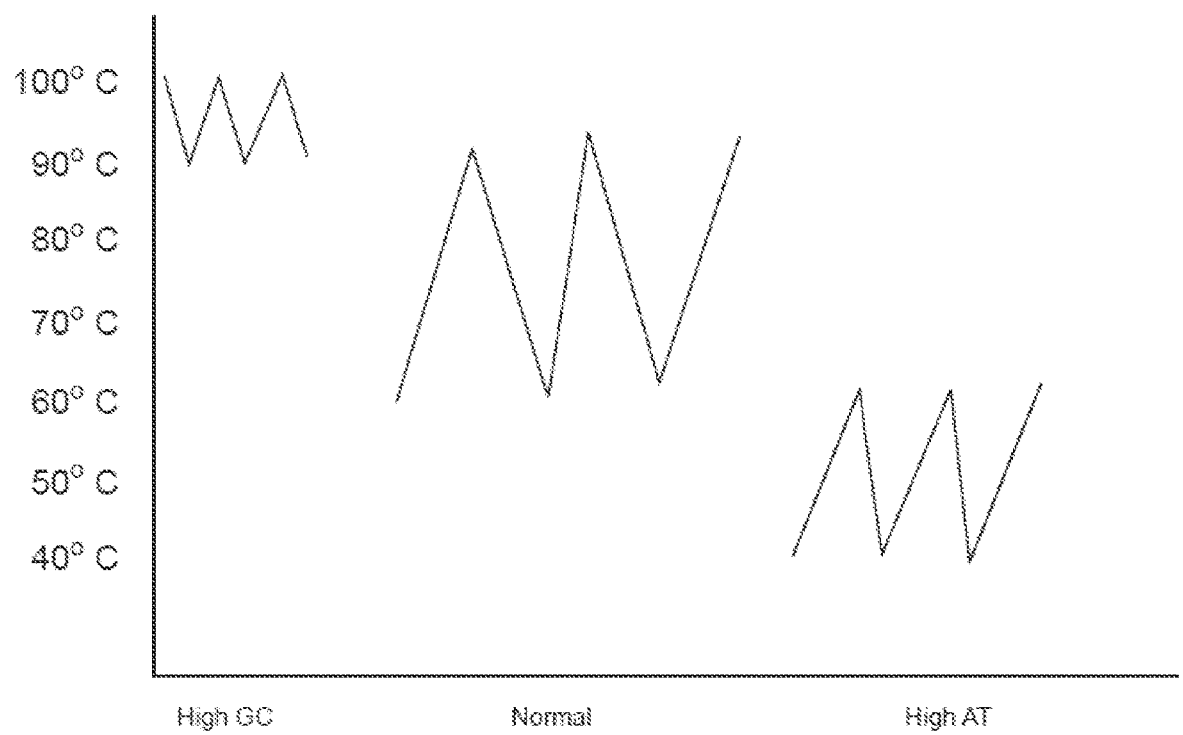
FIG. 20 depicts thermal profiles for amplification of high GC nucleic acid regions first, then normal nucleic acid regions (regions amplified by traditional PCR temperature ranges) second, and then high AT nucleic acid regions third.

An alternative thermal cycling profile for this assay depicted in FIG. 20 would be: between 95° C. and 99° C. for as many cycles as necessary to generate a result; between 60° C. and 95° C. for as many cycles as necessary to generate a result; and between 45° C. and 60° C. for as many cycles as necessary to generate a result. This profile could vary by temperature and number of cycles, depending on the primer designs and the DNA being examined. For example, in one embodiment, the number of cycles varies from one temperature range to another. It also may be that specific temperature suitable polymerases are chosen for each temperature range of thermal cycling. The specific order of the thermal cycling profiles, from low to high, or high to low, can vary depending on the objectives and the target regions being enriched, amplified and ultimately sequenced. In addition, the method may also comprise a certain degree of overlap between the thermal cycling ranges. For example, a set of thermal cycling parameters might comprise 50° C.-65° C., 60° C.-95° C., and 90° C.-105° C.

Figure 21:
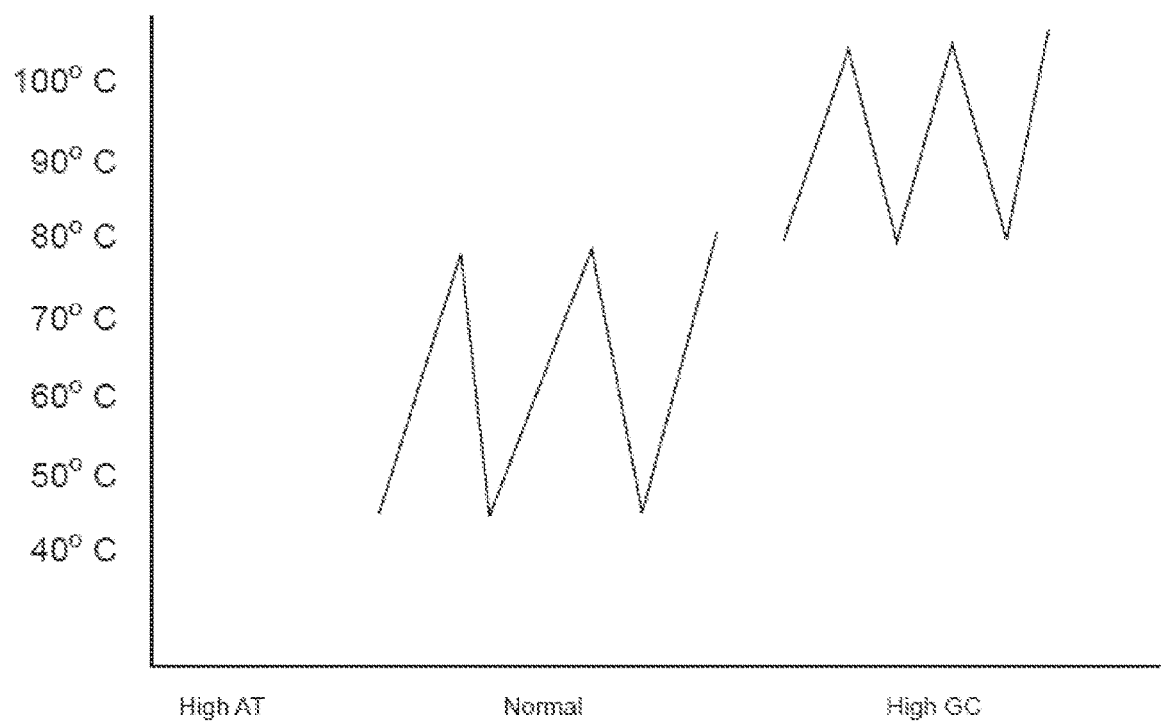
FIG. 21 depicts thermal profiles for amplification of nucleic acid regions between about 45° C. and about 72° C., and then for amplification of nucleic acid regions between about 72° C. and about 99° C.

In an alternative embodiment, depicted in FIG. 21, one set of primers is designed to thermal cycle between about 45° C. and about 72° C. and another set of primers is designed to thermal cycle between about 72° C. and about 99° C. The target nucleic acid would then be thermal cycled within about 45° C. and about 72° C. for 40 cycles, or as many cycles as necessary, and then thermal cycled between about 72° C. and about 99° C. for 40 cycles, or as many cycles as necessary to generate a result.

Figure 22:
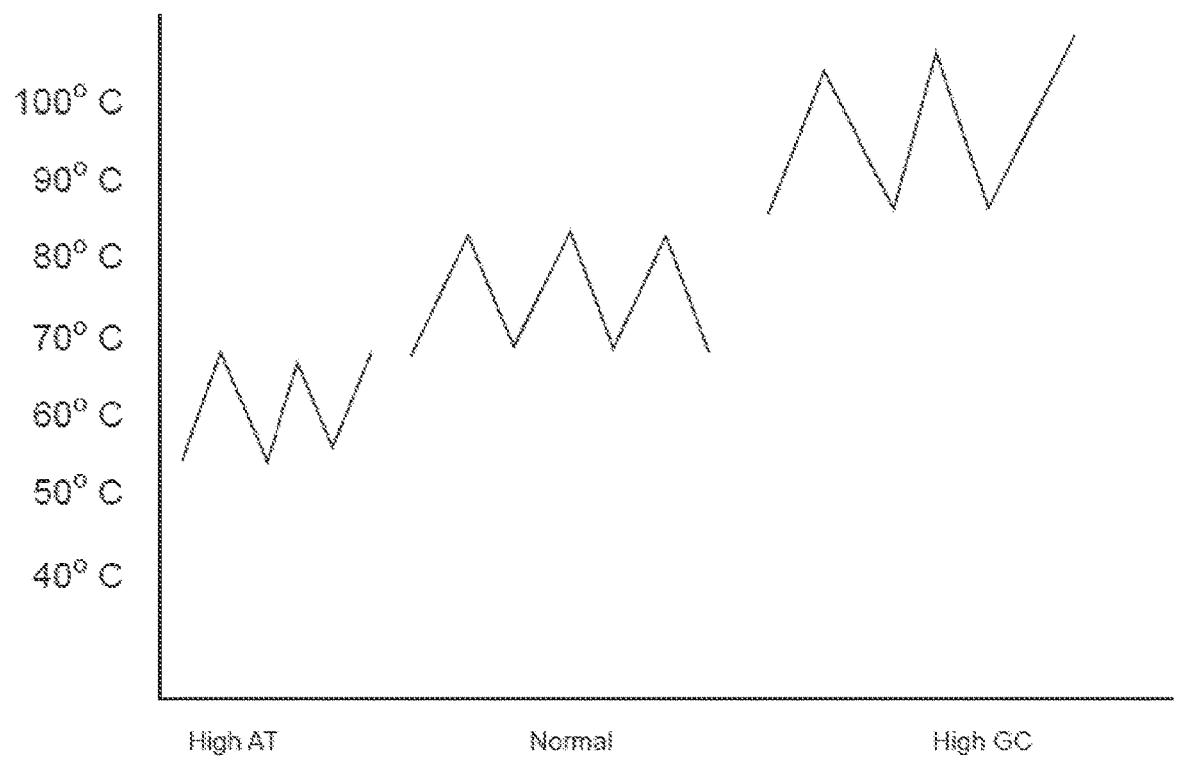
FIG. 22 depicts thermal profiles for amplification of nucleic acid regions between about 54° C. and about 63° C.; for amplification of nucleic acid regions between about 63° C. and about 81° C.; and for amplification of nucleic acid regions between about 81° C. and about 99° C.

In yet another embodiment, depicted in FIG. 22, the primers are designed to thermal cycle between about 54° C. and about 63° C.; between about 63° C. and about 81° C.; and between about 81° C. and about 99° C.

Temperature Dependent Multiplexing

Figure 23:
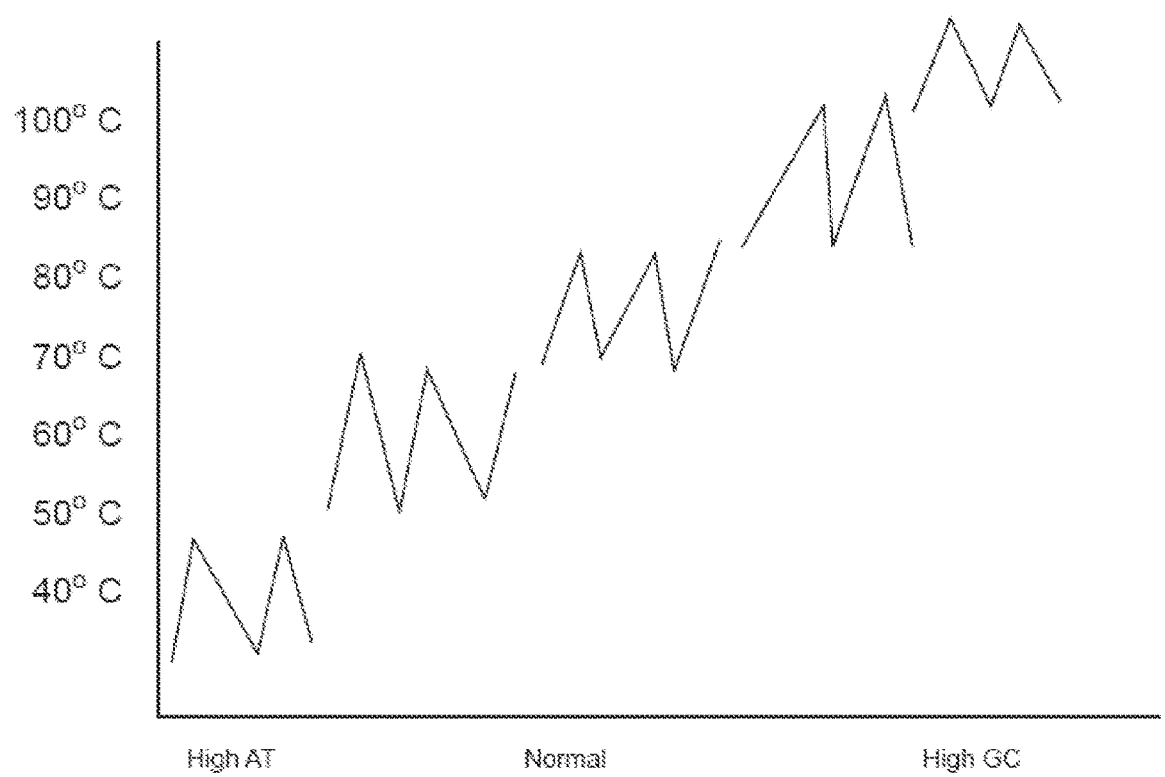
FIG. 23 depicts thermal profiles for amplification of five different nucleic acid targets from five different organisms. There are five distinct temperature ranges, one temperature range for each of the five targets, starting from low to high.
Figure 24:
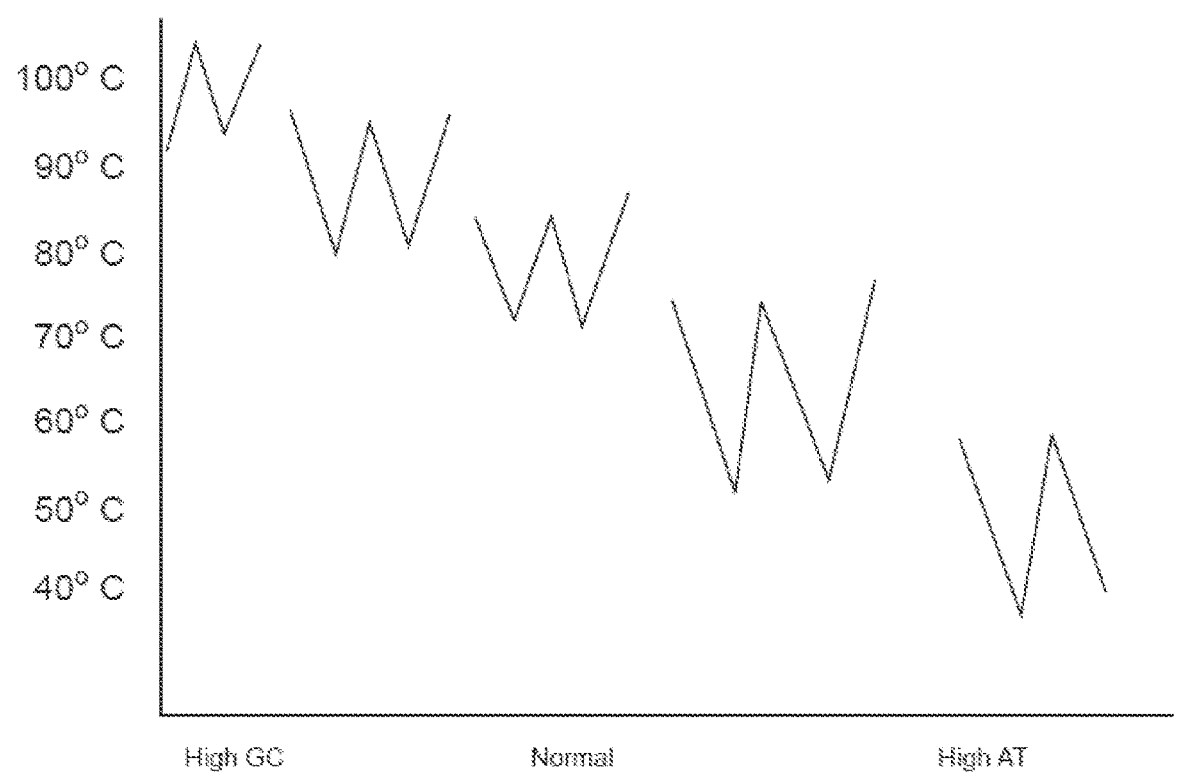
FIG. 24 depicts thermal profiles for amplification of five different nucleic acid targets from five different organisms. There are five distinct temperature ranges, one temperature range for each of the five targets, starting from high to low.

The method of using multiple temperature ranges for specific target primers as part of the amplification process can also be used to create a partially temperature dependent method of target detection and analysis. In one embodiment, depicted in FIG. 23, primers that correspond to five different organisms are designed to thermal cycle at five distinct temperature ranges, one temperature range for each of the five targets. A fluorescent dye, electrochemical indicator, or any other detection chemistry or method (could be a combination of multiple detection methods) can be used for each of the five targets. The mixture is then thermal cycled within each temperature range in succession. The cycling sequence could go from low to high (FIG. 23) or high to low (FIG. 24) or any other order. Readings may be taken during the amplification at each temperature range. The temperature ranges at which a positive result is achieved reveals which targets are being amplified. Of course, a variety of detection chemistries can be combined, either multiple fluorescent dyes, electrochemical indicators, target immobilization strategies, or any combination thereof are possible. Embodiments of detection chemistries that can be used with temperature dependent multiplexing are described below.

This method allows for simpler multiplexing in terms of designing the primers and probes, as well as simplifying the thermal cycler's method for reading the result. It also provides an advantage over conventional multiplexing because in conventional multiplexing, all the different targets are sought to be amplified at the same time. This means that all the primers are active at the same time and can potentially interact with each other. This phenomenon often causes design difficulties. With multiple temperature thermal cycling, each primer set is utilized only at its own thermal cycling range, and it is not competing with or binding to other primers. One thermal cycling sequence that can be used to accomplish multiple temperature thermal cycling comprises thermal cycling each temperature range in sequence, beginning with the lowest and moving successively to the highest. This pattern of thermal cycling ensures that at lower temperatures a heat labile nucleic acid polymerase or reverse transcriptase is not destroyed by high heat prior to its being needed for a subsequent amplification protocol. Thermal cycling protocols starting with higher temperature targets and working toward lower temperature targets and thermal profiles can also be quite suitable for producing amplification of an internal reaction control following the completion of a target of interest detection protocol.

In diagnostic testing, it is desirable and often required to include a control amplification that verifies correct processing of a sample and/or lack of inhibition of DNA or RNA amplification. As an internal control, this amplification can either use a different pair of primers and template, or can use the same primers as used for amplification of the target sequence with a distinct internal sequence. When the control amplification occurs within the same reaction vessel as the target amplification (an internal control), competition between amplicons can occur, resulting in decreased sensitivity. Multi-temperature thermal cycling addresses this problem by first amplifying the target species within a thermal cycling temperature range, then after completion, altering the thermal cycling temperature range to enable amplification of the internal control. Such sequential thermal cycling is made possible by the properties of XCR in which discrete thermal cycling parameters are optimized for each amplicon. Similarly, in multiplex amplification of distinct target species, sensitivity can be maintained using multiple thermal cycling profiles, such that amplicons do not compete with each other.

By using primers which have a higher Tm after the initial extension, narrow thermal cycling parameters can be maintained after the initial round of extension, permitting higher specificity and greater speed of amplification. A further benefit of this approach is that high concentration numbers of control template or organism can be present in the amplification without loss of sensitivity, increasing reproducibility and decreasing the time required for the second (control) thermal cycling period. Finally, an unanticipated effect of GC-rich primer tails has been noted (see Example 4): increased amplification efficiency even when the anneal/extend temperature remains much higher than the predicted Tm. This observation suggests the utility of GC-rich primer tails added to the target amplicon as well as control amplicon: after initial round(s) of amplification, the anneal/extend temperature can be raised to shorten cycling time, speed up time to Ct and decrease turnaround for a given test that uses multi-temperature thermal cycling.

Probes and Primers for DFA and Temperature Dependent Multiplexing

A distinct feature of DFA probes and primers is possession of melting temperatures (Tm) that are close to the Tm of the target sequence. To satisfy this operating parameter, the primers and probes generally must possess higher Tm than those used in PCR amplification. As a consequence, common probe designs used for PCR generally cannot work with DFA, particularly if a real time readout is desired. Hence, the following describes primer and probe designs, as well as probe and primer combinations that can be used with DFA and temperature dependent multiplexing.

In one or more embodiments, the technology described involves modifications of existing probe and primer technology to function with DFA and temperature dependent multiplexing.

In other embodiments, the technology described minimizes the number of probes and primers required for DFA and temperature dependent multiplexing operations. The oligonucleotides can be configured and used to limit the number of different oligonucleotides present during the reactions.

Many specific probe designs and probe label combinations are discussed in the literature and known to those of average skill in the art. These include, but are not limited to, the technologies set forth in the following: U.S. Pat. Nos. 5,491,063; 5,538,848; 5,571,673; 5,573,906, and 5,804,375, which are each incorporated by specific reference in their entirety.

i. DFA Cleaved Probe Technology—Considerations

Figure 32:
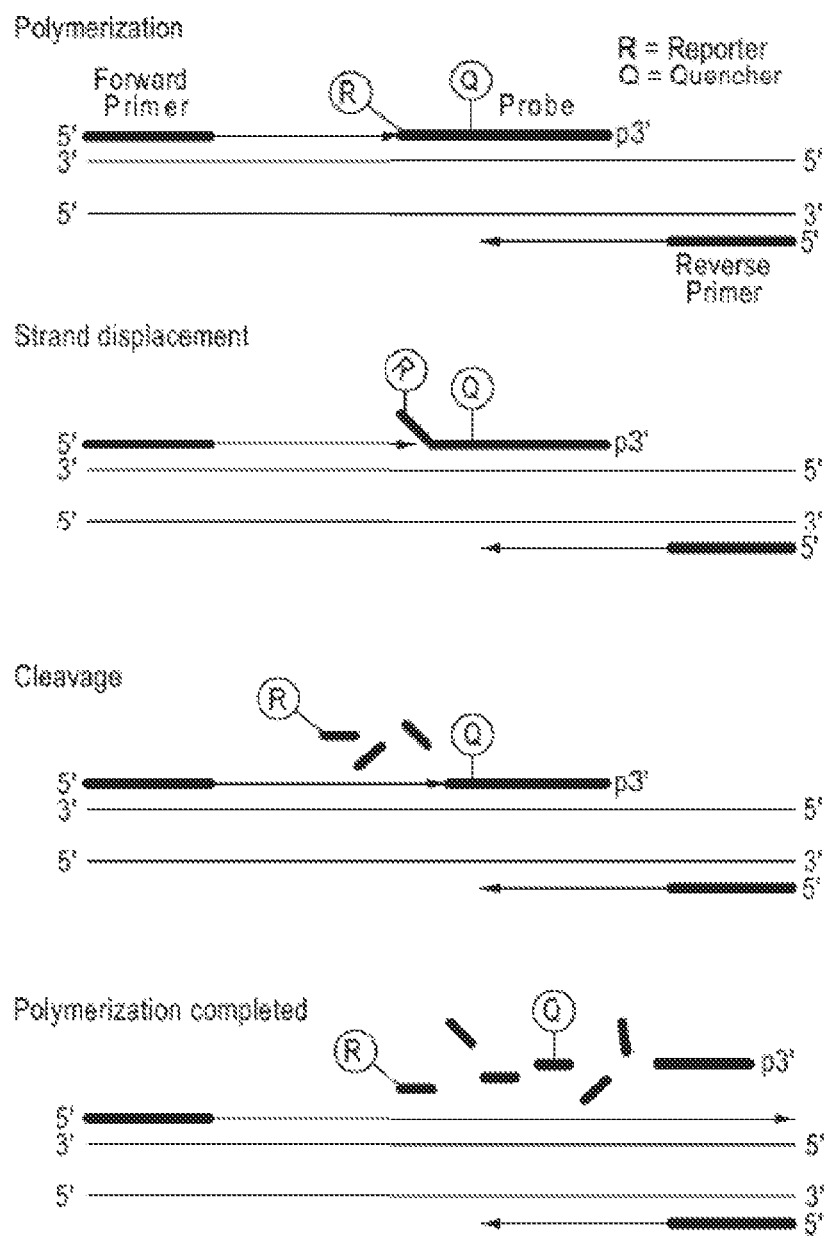
FIG. 32 is a general embodiment of cleaved probe technology according to the disclosure.

For exemplary reasons, one embodiment of the disclosure is based on cleaved probe technology, illustrated generally in FIG. 32 and set forth as follows. Cleaved probe technology refers to any of several strategies that may be employed to distinguish the uncleaved labeled oligonucleotide from the cleaved fragments thereof. In this manner, cleaved probe technology permits identification of those nucleic acid samples which contain sequences complementary to the upstream and downstream oligonucleotides.

The present DFA cleaved probe technology embodiment is a modification of existing cleaved probe technology. For background purposes, cleaved probe technology is described as follows. Cleaved probe technology is based on a 5' to 3' nuclease activity whereby the nucleic acid polymerase can cleave a mononucleotide or small oligonucleotides from an oligonucleotide (e.g., downstream oligonucleotide) annealed to its target oligonucleotide. In order for cleavage to occur efficiently, an upstream oligonucleotide must also be annealed to the same target oligonucleotide.

The 3' end of this upstream oligonucleotide provides the initial binding site for the nucleic acid polymerase. As soon as the bound polymerase encounters the 5' end of the downstream oligonucleotide, the polymerase can cleave mononucleotides or small oligonucleotides therefrom.

The two oligonucleotides can be designed such that they anneal in close proximity on the complementary target nucleic acid such that binding of the nucleic acid polymerase to the 3' end of the upstream oligonucleotide automatically puts it in contact with the 5' end of the downstream oligonucleotide in a process known as "polymerization-independent cleavage."

Alternatively, if the two oligonucleotides anneal to more distantly spaced regions of the template nucleic acid target, polymerization must occur before the nucleic acid polymerase encounters the 5' end of the downstream oligonucleotide. As the polymerization continues, the polymerase progressively cleaves mononucleotides or small oligonucleotides from the 5' end of the downstream oligonucleotide. This cleaving continues until the remainder of the downstream oligonucleotide has been destabilized to the extent that it dissociates from the template molecule in a process that is called "polymerization-dependent cleavage."

In practice, the upstream oligonucleotide comprises the primer and the downstream oligonucleotide comprises the probe.

The probe contains at least one label which is cleaved by the nuclease activity. In some embodiments, the probe comprises an upstream label and a downstream label. The upstream label comprises a fluorescent dye or quencher, and the downstream label comprises a fluorescent dye or quencher, such that when the probe is in solution, the signal from the fluorescent dye is suppressed by the quencher. Thus, when the upstream label comprises a fluorescent dye, the downstream label comprises a quencher, and vice versa.

When binding of the probe and primer to the target oligonucleotide occurs, the polymerase cleaves either the fluorescent label or the quencher, or both releasing them into the solution such that the dye is no longer subject to the quencher and can fluoresce.

In designing the primer and probe combination to utilize probe technology polymerase in the case of DFA, the following factors must be taken into consideration.

First, because one of the central features of DFA is the close proximity between the Tm of the primers and the Tm of the sequence of interest, the primers must frequently be longer than the primers used in PCR. In embodiments, the primers are frequently 50 base pairs, more or less.

Second, because the probes must also anneal at approximately the same or slightly higher temperatures than the primers, they are frequently longer than the probes used in PCR. In embodiments, the probes must also be 50 base pairs or greater.

Third, in order to accommodate probes and primers of this length, the target sequence must be longer than that of PCR. These lengths may vary somewhat depending on the GC content of the respective probes and primers.

The longer probe length creates a problem in using existing cleaved probe chemistry with DFA for the following reason. Quenching generally follows the following formula: F=1/r3.

Thus, in the case of existing cleaved probe chemistries, the quencher is generally sufficiently close radially to the fluorophore that, when the probes are in solution, quenching effectively takes place. In the case of DFA probes, the quencher is generally not sufficiently close radially to the fluorophore to quench when the probes are in solution.

Thus, in the case of traditional cleaved probe chemistries, it is impossible to distinguish between cleaved probes and probes still in solution.

A solution to this problem is herein referred to as "hybrid hairpin/cleaved probes" or simply "hybrid probes."

ii. DFA Cleaved Probe Technology—Hybrid Hairpin/Cleaved Probes

Specifically, these hybrid hairpin/cleaved probes are similar to traditional hairpin probes in that the oligonucleotide strand comprising the probe contains at least one pair of complementary sequences. When the probe is in solution, the complementary sequences intramolecularly hybridize to each other, causing the probe to take on a hairpin like shape and thereby bringing the quencher into sufficient radial proximity to the fluorophore to quench the signal from the fluorophore.

The following comprise exemplary sequences for a DFA oligonucleotide probe that will form a hairpin:

```
Structure 1 Folding bases 1 to 72 of mfoldExample1
                                                 (SEQ ID NO: 1)
dG = -2.98 dH = -84.20 dS = -261.87 T_m = 48.4° C.
            10         20
 .-ACCTCCAATGCC|        ACTCC
                  AAACATT     T
                  TTTGTAA     T
 \ ------------^        CTCAG
                         30

40         50
  CCTGT    CGATGCGCT
      GCCA          T
      CGGT          A
  C----    ACCCAGATT
      70         60

Structure 1 Folding bases 1 to 67 of mfoldExample2
                                                 (SEQ ID NO: 2)
dG = -5.79 dH = -129.70 dS = -399.52 T_m = 51.5° C.
               10
 .-A      --|  TT
   GCACT  CAG   \
   CGTGG  GTC   A
 \ -      TC^  TT
         20

30
 .-ACTT  CA
      GC  \
      CG  G
 \ ----  TT 40         50
  ATG G      ATAC
    G CCTCAT    A
    C GGGGTA    A
  T-- G       GGAC
            60

Structure 1 Folding bases 1 to 83 of mfoldExample3
                                                 (SEQ ID NO: 3)
dG = -3.35 dH = -101.40 dS = -316.14 T_m = 47.6° C.
            10         20
 .-ATGGACGTGGCTT|     T
                 AGCGTA A
                 TCGTAT T
 \ -------------^     T 30        40        50
 .-GATGGAAAAATGGTAA       GCT
                    ACGAA  \
                    TGCTT   T
```

```
                                      -continued
    \ ----------------    GAT
                      60

70
    CAAGG    GG
         CTT    \
         GAA   C
    TCGTT   AT
      80

Structure 2 Folding bases 1 to 83 of mfoldExample3
                                                    (SEQ ID NO: 4)
dG = -2.92 dH = -94.60 dS = -295.60 T_m = 46.9° C.
          10         20
.-ATGGACGTGGCTT       T
              AGCGTA A
              TCGTAT T
\ -------------       T 30       40        50        60
   GATGGAAAAATGGTAAACGAAG|      TCGTCA
                         CTTTAGT      \
                         GAAATCG     A
    TCGTT----------------^       GTTCGG
       80                      70

Structure 1 Folding bases 1 to 67 of mfoldExample4
                                                    (SEQ ID NO: 5)
dG = -13.55 dH = -129.20 dS = -372.88 T_m = 73.3° C.
                 10
.-A      --|  TT
   GCACT  CAG  \
   CGTGG  GTC   A
\ -    TC^  TT
       20

30
   .-ACT   CA
       TGC  \
       ACG  G
  \ ---   TT 40       50
  TG G     ATAC
    G CCTCAT   A
    C GGGGTA   A
   T- G    GGAC
         60

Structure 1 Folding bases 1 to 38 of LTSOW_SNP2CT_xm1
                                                    (SEQ ID NO: 6)
dG = -2.40 dH = -75.20 dS = -234.73 T_m = 47.2° C.
         10
TG--|   TCC     TTTC
    GCAA   CAGGT    T
    CGTT   GTCCA    T
AACT^   T--     TCTT
       30      20

Structure 7 Folding bases 1 to 36 of LTSOW_TERT_XM1 75-90
                                                    (SEQ ID NO: 7)
dG = -0.79 dH = -30.80 dS = -96.76 T_m = 45.2° C.
             10
C---------| A   ATCCCC
         AG CCC       \
         TC GGG      C
TCCTCCGGTA^ A   AGTGGA
     30       20

Structure 1 Folding bases 1 to 30 of LTSOW_RNAseP_XM1
                                                    (SEQ ID NO: 8)
dG = -2.25 dH = -22.40 dS = -64.97 T_m = 71.6° C.
        10         20
TCAATGGCTGAGGTGAGGTAC|   G
                     CCC  \
                     GGG  C
--------------------^    A
                    30
```

-continued

```
Structure 1 Folding bases 1 to 42 of LTSOW_CC3_XM1
                                                  (SEQ ID NO: 9)
dG =  0.02  dH =  40.30  dS = -130.00  T_m = 36.8° C.
         10          20
TTTGCT|      AGTTCCCCTGT
      CTGAG            C
      GACTC            C
------^      CCTTCCACCTCC
         40          30

Structure 1 Folding bases 1 to 45 of LTSOW_CYPD2D_XM1
                                                  (SEQ ID NO: 10)
dG = -3.06  dH = -31.50  dS =  -91.70  T_m = 70.4° C.
         10          20
TGCAAGAGTCACCAAAATT|  G
                   GCC A
                   CGG G
ACCCTACGATTGACCC---^  A
         40          30 mfold version 3.5
M. Zuker, Rensselaer Polytechnic Institute
```

However, the hybrid probes differ from traditional hairpin probes in the following manner. Unlike traditional hairpin probes, the hybrid comprises sequences on their ends that are complementary to the opposite sequences on the DNA strand to which the probe anneals. This causes the probe to anneal completely to the target sequence in the same or similar manner of a cleaved probe. Thus, like a cleaved probe, the hybrid probe is cleaved as the polymerase extends the sequence. This differs from traditional hairpin probes in that the ends of traditional hairpin probes, are deliberately designed to not complement their opposite target sequence. This is done to allow the polymerase to move under the probe.

In another embodiment, the melting temperature of the primers and probes may be increased without significantly increasing oligonucleotide length by covalently coupling agents which bind to single- or double-stranded DNA, thereby increasing the Tm. A class of agents known as minor groove binders bind and stabilize helical DNA, and have been exploited as probes within the limited temperature range. By increasing the Tm, shorter primers and probes can function within DFA temperature range. For PCR temperature ranges, an example of this approach is the use of minor groove binding agents. Many other classes of agents, including those which bind to both single stranded and double stranded DNA, are contemplated as in the example below.

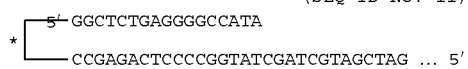

(SEQ ID NO: 11)

As shown above, the primer or probe has a covalently linked moiety (labeled as "*") that binds to adjacent DNA and increases the primer/probe Tm. The stabilizing moiety can bind to either ds or ssDNA.

In a further embodiment, oligonucleotide backbone or base modifications that increase Tm can also be utilized to move primer/probe Tms into the DFA range without increasing oligonucleotide length.

Such modifications include but are not limited to LNA, PNA, dithiophospate linkages, 2' sugar modification such as 2'-O-Methyl, 2'-fluoro, base modifications such as 5-halopyridines, 5-methyl pyrimidines, bases which make additional hydrogen bonds, other purine base modifications such as super G, 2-amino purine, and the like.

iii. DFA Probe Technology—FRET Probes

Figure 33:
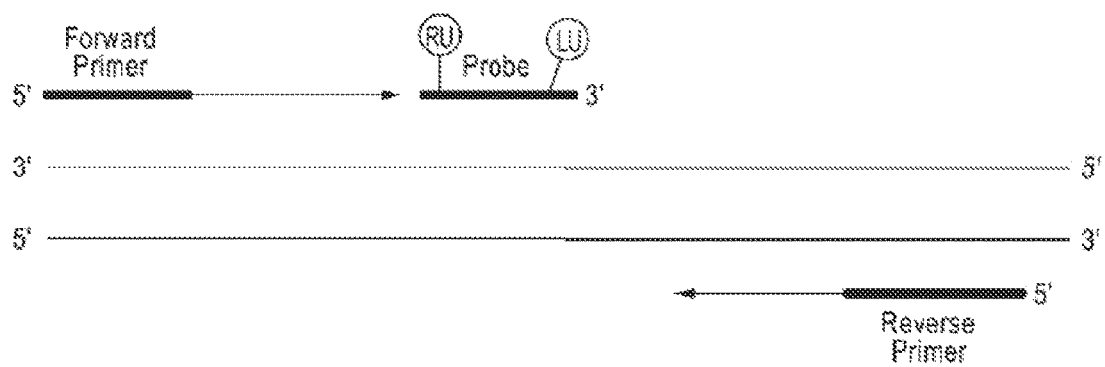
FIG. 33 depicts cleaved probe technology in an embodiment where bathophenanthroline-RU II complexes are used as label molecules.

In another embodiment of cleaved probe technology, depicted in FIG. 33, bathophenanthroline-RU II complexes are used as label molecules. These complexes can be part of an interactive pair of label molecules allowing energy transfers from suitable energy donor molecules to the Ru complex. Because the efficiency of the energy transfer is highly dependent on the distance between the donor and acceptor molecules, such energy transfer systems are useful in studying molecule interactions.

A suitable class of acceptor molecules for use as the Ru complexes is the lumazine chromophore group of molecules. Using such a combination, energy transfers may be detected between the Ru bathophenanthroline complex and the lumazine chromophores where the Ru complex is located at a suitable distance from the lumazine chromophore. When used in conjunction with polymerase cleaving technology, wherein one of the two labels is cleaved from the probe, a change in luminescence may be detected which is useful in determining whether amplification of the target sequence has been achieved.

Figure 34:
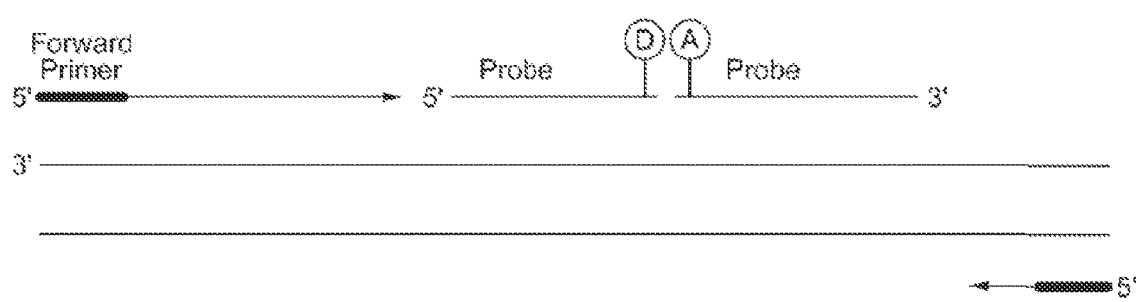
FIG. 34 depicts a Dual Hybridization Probe and Primer combination.

FIG. 34 depicts a Dual Hybridization Probe and Primer combination. This embodiment comprises two sequence-specific oligonucleotide probes in addition to two sequence specific primers. The probes comprise pairs of dyes that can engage in fluorescence resonance energy transfer. (FRET), with a donor dye attached to one probe and an acceptor dye attached to the other probe, with both the donor dye and the acceptor dye located such that when the probes are attached to the target sequence, they are sufficiently proximate to each other to engage in FRET. Both the probes and the primers meet the temperature requirements for XCR.

Figure 35:
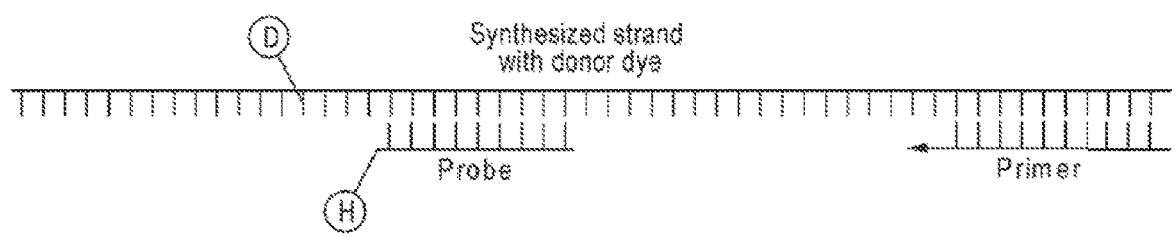
FIG. 35 depicts a primer/probe combination capable of engaging in FRET.

FIG. 35 depicts a primer/probe combination capable of engaging in FRET. A sequence-specific oligonucleotide primer and a sequence-specific oligonucleotide probe are designed to bind to adjacent sequences of the target, usually with the probe complementary to the strand formed by the primer, such that the probe anneals to the complementary strand synthesized from the extended labeled primer.

Designing assays containing probes and primers of these lengths yielded unexpected results in that it was generally thought that probes and primers of these lengths could not be designed to possess Tm's within the narrow ranges of the Tm of the target sequence required for DFA. However, it has been found that probes and primers with adequate Tm ranges for DFA can be readily designed.

Primer/Primer XCR Detection Chemistry

Observation from extant probe detection chemistry, such as HybBeacon and HyGlow probes, show that the native folding of probes into tight secondary structures and the accompanying relative hydrophobicity of fluorescent dyes allows these fluorescent moieties to come into close proximity if not actual contact with one another. This is believed to occur from a general entropically favored configuration for the folded oligonucleotides and their attached dyes.

XCR has demonstrated its ability to amplify DNA or RNA templates at nearly 10× the speed of traditional PCR technologies. One substantial limitation to performing amplifications at those speeds is the need to incorporate a probe based detection during the amplification protocol. The primary source of the additional time required is the need for the hybridization of the probe, and in the case of 5' nuclease XCR probes, the additional time required for the probe to be cleaved to release quenching of the dye from its quencher.

The following describes a method of detecting fluorescence in real time amplification that takes advantage of the HybBeacon and HyGlow technologies, where fluorescence quenching is released by the binding of the oligonucleotide to its complement template.

According to this design, in lieu of the fluorescent oligonucleotide being a probe, the fluorescent molecules are the primers used to produce the amplification.

Figure 36:
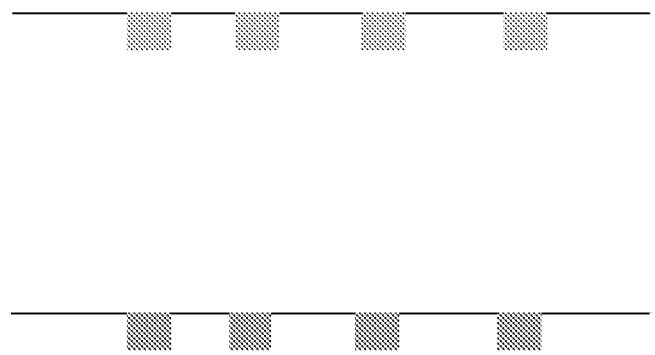
FIG. 36 illustrates forward (top) and reverse (bottom) primers with dye (squares) spaced approximately 6-9 nucleotides apart along the length of the primers, but with sufficient nucleotides left without dye on the 3' end. When the primers bind to their complement, fluorescence quenching is released and thus a detectable signal is created.

The primary advantage being that additional time to allow the fluorescent probe to bind is not required, as the primers are inherently annealed and 'stretched' out on the template thus releasing the fluorescence quenching upon initiation of the priming complex. See FIG. 36, illustrating forward and reverse primers with dye spaced approximately 6-9 nucleotides apart along the length of the primers, but with sufficient nucleotides left without dye on the 3' end. When the primers bind to their complement, fluorescence quenching is released and thus a detectable signal is created.

The fluorescent primers serve several purposes in this design. First, two fluorescent signals are generated, one for the forward primer binding to the appropriate template and one for the reverse primer binding to the opposite strand template.

Should a primer form an extension product, primer-dimer, with another like primer then dyes on the primer should be in close enough proximity to prevent the release of quenching and thus remain quenched and produce no fluorescent signal from such primer-dimer complexes.

Figure 37:
FIG. 37 illustrates quenched forward primer-dimer complex (top), quenched reverse primer-dimer complex (middle), and primer-dimer complex formed from the binding together of the forward and reverse primers (bottom), which is detectable via FRET signal. Squares represent dyes.
Figure 37:
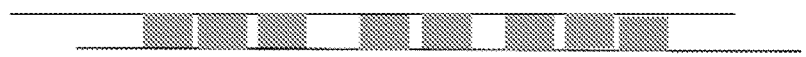
Figure 37:

Should the two differently labeled primers form a primer-dimer complex, their quenching will not be relaxed, but rather a FRET complex will be formed, and the signal indicating the formation of the primer-dimer complex will be monitorable by excitation at the higher energy wavelength with emission at the lower energy wavelength (a standard FRET signal). See FIG. 37, illustrating quenched forward primer-dimer complex, quenched reverse primer-dimer complex, and primer-dimer complex formed from the binding together of the forward and reverse primers, which is detectable via FRET signal.

Figure 38:
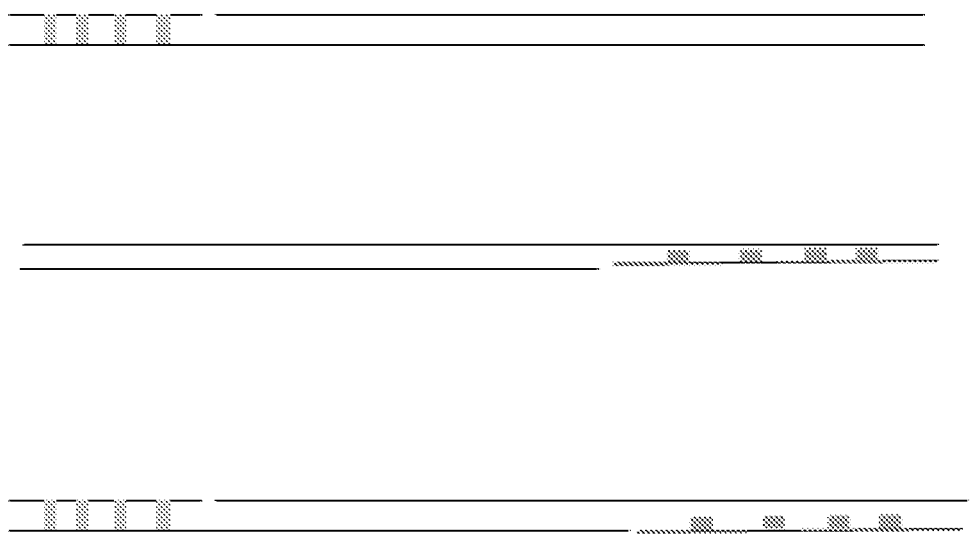
FIG. 38 illustrates forward primer template formation signal (top), and reverse primer template formation signal (middle), and signal generated when both the forward and reverse primers produce the targeted template (bottom). Squares represent dye.

Under certain circumstances, where template dependent non-specific product is made, it may be possible for a single primer to initiate the priming of a template. These products will produce single fluorescent dye signals. See FIG. 38, illustrating forward primer template formation signal, and reverse primer template formation signal, and signal generated when both the forward and reverse primers produce the targeted template.

Figure 39:
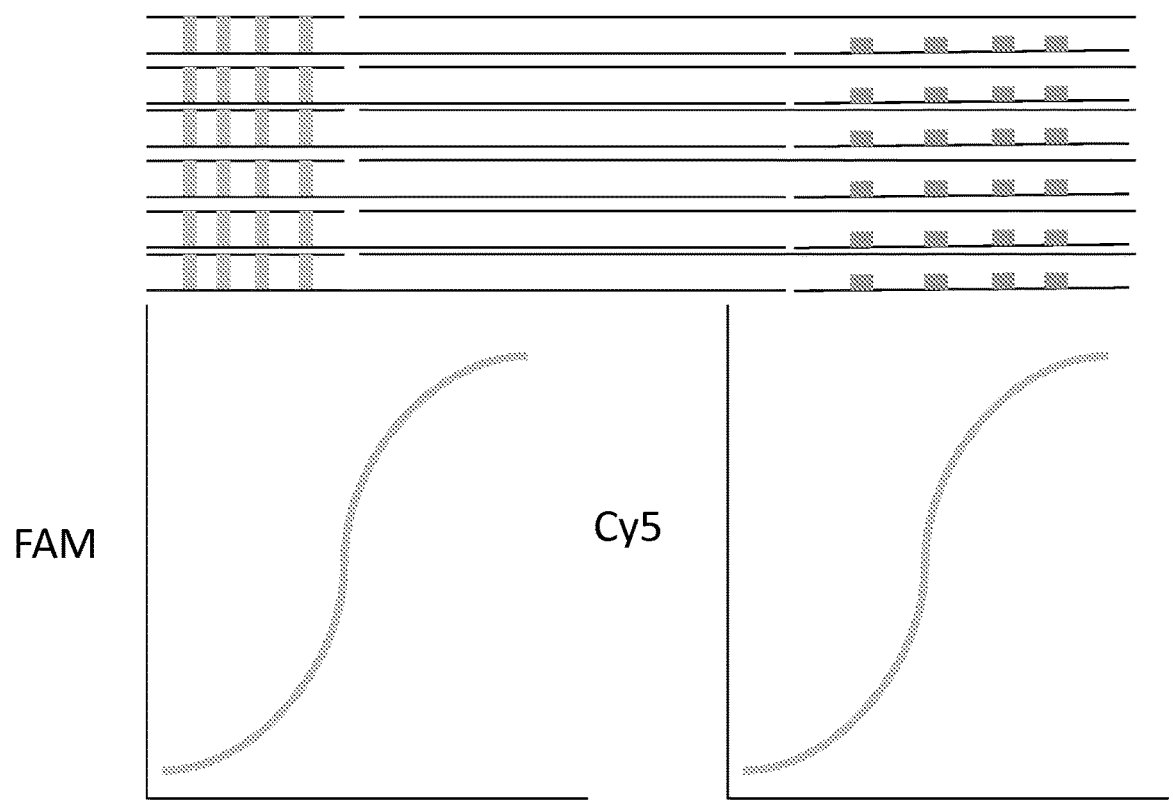
FIG. 39 illustrates that correct products with both dye labeled primers will show the formation of fluorescent signal from both distinct dyes with equal reaction formation efficiency, as they will be linked directly to one another in the formation of amplification product and could be monitored in two fluorescent channels simultaneously. Forward primer signal on left and reverse primer signal on the right.

Whereas, correct products with both dye labeled primers will show the formation of fluorescent signal from both distinct dyes with equal reaction formation efficiency as they will be linked directly to one another in the formation of amplification product and could be monitored in two fluorescent channels simultaneously. See FIG. 39.

Figure 40:
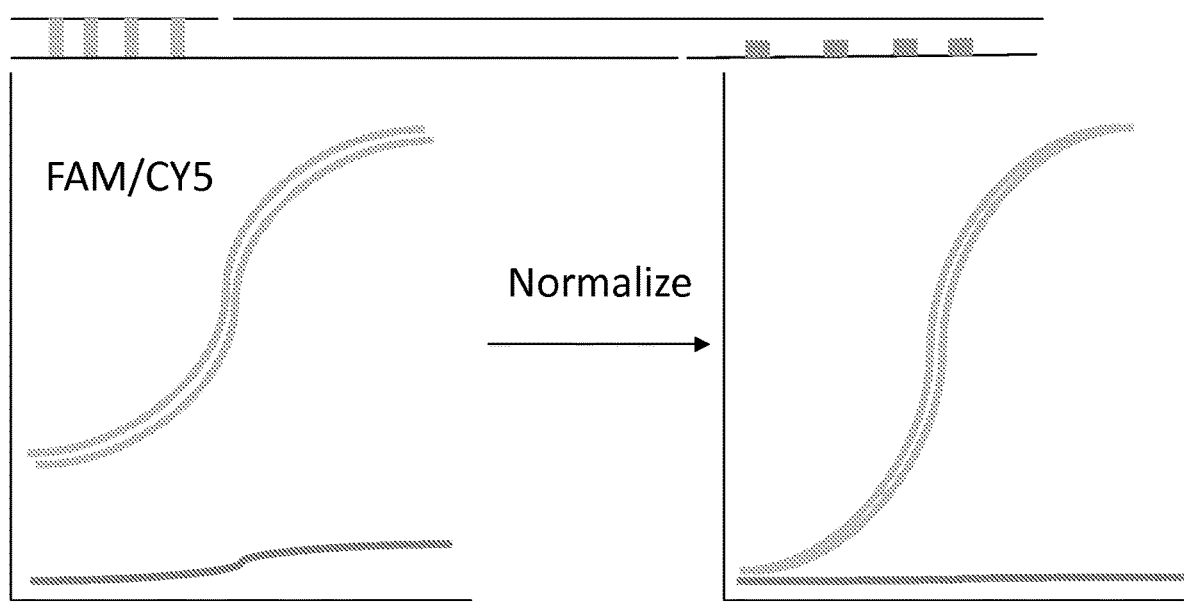
FIG. 40 illustrates a data evaluation advantage of the present disclosure design strategy where amplified product is formed and both fluorescent signals are generated by the amplifying product. Any primer-dimer signals that result in FRET, as the like primers will be quenched, can be subtracted from the formed signals to enable a baseline normalization of the amplification signals. Forward and reverse primer signals forming sigmoidal curve. Primer-dimer signal to be subtracted is illustrated via line at the bottom of the graph.

Another data evaluation advantage of this design strategy is where amplified product is formed and both fluorescent signals are generated by the amplifying product. Any primer-dimer signals that result in FRET, as the like primers will be quenched, can be subtracted from the formed signals to enable a baseline normalization of the amplification signals. See FIG. 40.

Overall, the advantage of this technique is that it will not limit XCR speed during the amplification by no longer needing to wait for the probe to hybridize or for the probe to be cleaved.

In addition to XCR, this design is suitable for PCR assays as well; however, the reason that such a chemistry has not been implemented and it has been non-obvious is that PCR suffers from substantial non-specific product formation and the use of primers only, as in the case of double stranded DNA binding dyes like SYBR Green 1, have been largely ignored as suitable for diagnostic testing methodology.

Triplex Forming Region Probe Design

In another embodiment, the present disclosure provides a multiplex probe technology that is suited for use with DFA or temperature dependent multiplexing.

This embodiment minimizes the required number of oligos (e.g., primers and probes) by eliminating the need for the probes to participate in the amplification portion of the reaction.

Most current probe technology utilizes individual or multiple oligonucleotides to probe for the amplified sequence. The oligonucleotide probes bind to the sequence of interest in the course of the DNA amplification.

In contrast, amplification may be detected using triplex forming regions (TFR) appended to sequence specific primers. This disclosure then uses a triplex forming oligonucleotide probe designed to interact with each specific product at the TFR to produce a unique color of fluorescence based on the particular product formed. This reduces the number of oligonucleotides present in the reaction.

The triplex forming probe does not participate in the amplification reaction and hence does not slow the reaction down in the way existing probe technology has a tendency to do.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

The practice of the present disclosure will employ, unless otherwise indicated, conventional techniques of molecular biology, microbiology, and recombinant DNA techniques as explained fully in the literature, as well as the methods disclosed in U.S. Pat. No. 7,838,235, incorporated herein by reference in its entirety.

In one embodiment, a triplex forming oligonucleotide probe based detection chemistry for nucleic acid amplification products is utilized. According to this method, a triplex forming primer is synthesized according to the following method.

An artificial sequence triplex forming region (TFR) is added to the designed oligonucleotide to create the triplex forming primer.

As used herein, a triplex forming region, or TFR, refers to particular DNA sequences that lend themselves to Hoogsteen, or triplex base pairing, in that a third strand of DNA binds to the double stranded TFR to form a triple stranded length of DNA, known as a triplex.

The following are illustrative examples of sequences that form triplex forming regions:

```
                                          (SEQ ID NO: 32)
5' - GTGTGGGAAGAGGGGGAXGAGGGGGAGGAGC - 3'

(SEQ ID NO: 33)
3' - CACACCCCTTCTCCCTXCTCCCCTCCGTCG - 5'

(SEQ ID NO: 34)
5' - GTGTGGGAAGAGGGGGAXGAGGGGGAGGAGC - 3'

(SEQ ID NO: 35)
3' - CACACCCCTTCTCCCTXCTCCCCTCCGTCG - 5'
```

In one embodiment, the TFR is located on the 5' end of the designed primer.

In an alternative embodiment, the TFR is located proximate to the 5' end of the designed primer.

In another embodiment, the TFR is located at any location internal to the designed primer.

In another embodiment, the TFR is located on the 3' end of the designed primer.

In another embodiment, the TFR is located proximate to the 3' end of the designed primer.

The triplex forming primer can be a segment of DNA or RNA that is complementary to a given DNA sequence and that is needed to initiate replication by DNA polymerase.

The triplex forming oligonucleotide may comprise a Triplex Forming Oligonucleotide probe (TFO probe). The TFO probe can be complexed to an appropriate sequence triplex forming region of double stranded nucleic-acid sequence and thus, when the TFO probe is labeled in some manner, as with a fluorophore, the TFO probe can be used to identify any nucleic-acid sequence.

In one embodiment, the primer comprising a Triplex Forming Region (TFR primer) may also possess a fluorescent dye.

Figure 41:
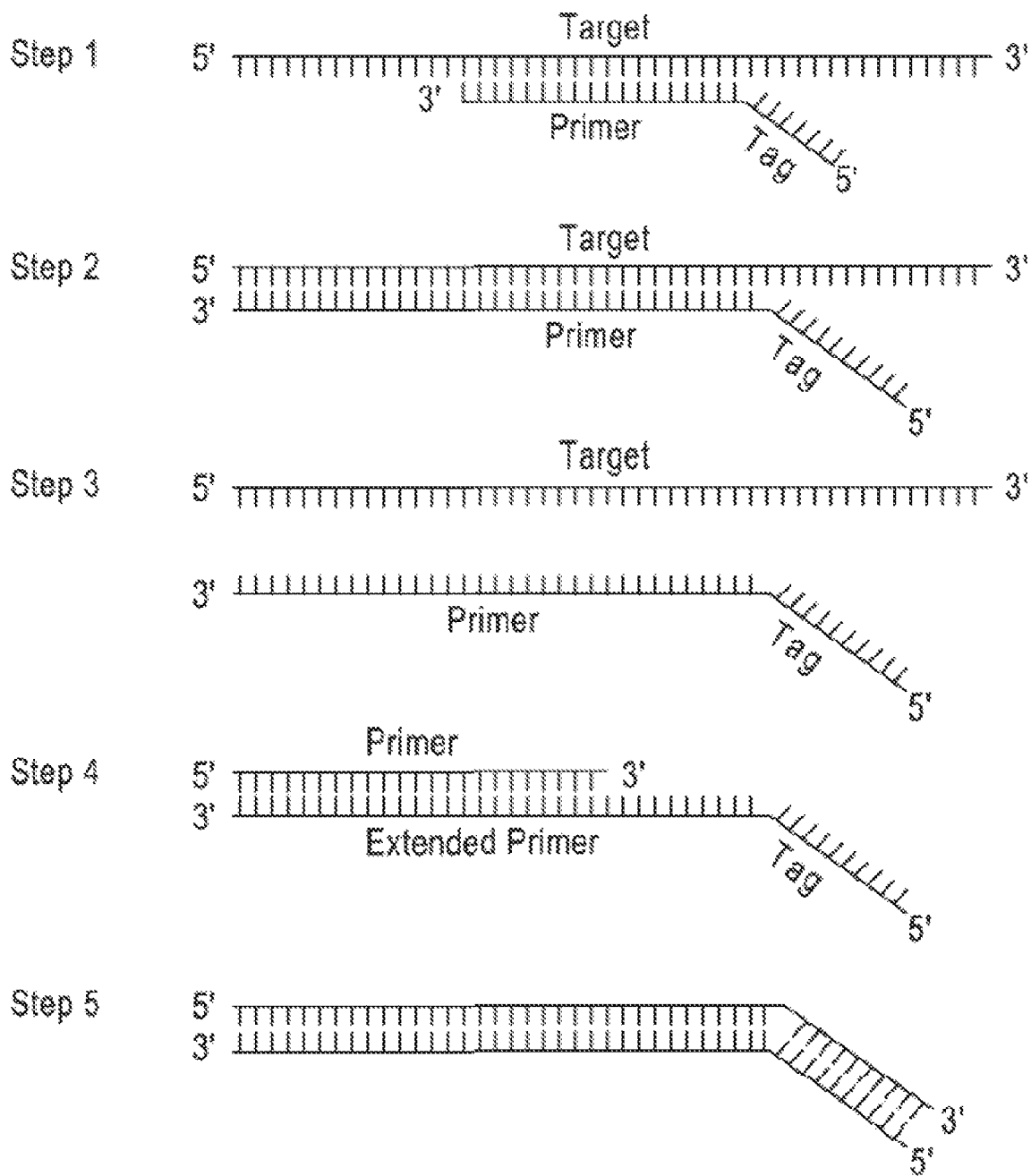
FIG. 41 illustrates that the triplex forming region (TFR) primer participates in the amplification of the target sequence, creating strands of triplex forming DNA along the length of and appended to the target sequence.

As depicted in FIG. 41, the TFR primer participates in the amplification of the target sequence, creating strands of triplex forming DNA along the length of and appended to the target sequence.

Step 1 depicts the single strands of the denatured DNA of the target sequence, bonded to the oligonucleotide primer. The oligonucleotide primer comprises a tag end sequence that does not match the target sequence. The tag end sequence comprises one or more triplex forming sequences.

Step 2 depicts the extension phase of the amplification process. During this phase, the primer is extended towards its 3' end to create a target for the next cycle.

Step 3 depicts the extended primer denatured from the target.

Step 4 depicts a primer with no tag annealed to the extended TFR primer.

Step 5 depicts the extension phase of the primer with no tag to create double stranded DNA sequence with a Triplex Forming Region.

The following detection method may then be employed to determine whether the TFO probe has bonded with the double stranded Triplex Forming Region of the amplified DNA, indicating that the DNA possesses the sequence of interest.

Figure 42:
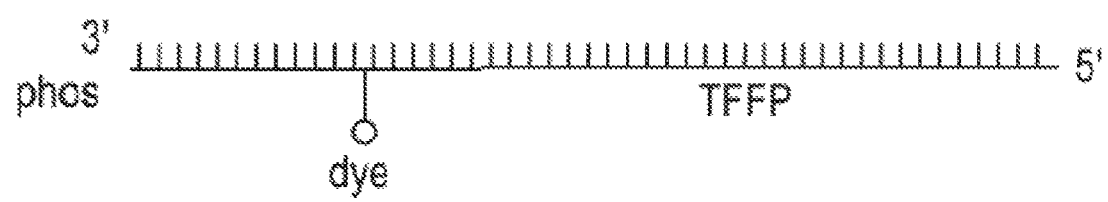
FIG. 42 illustrates a triplex forming oligonucleotide probe with the 3' end of the triplex forming oligonucleotide (TFO) probe being capped.

As depicted in FIG. 42, a triplex forming oligonucleotide probe is created in the following manner. A single stranded TFO is designed to bind to the Triplex Forming Region in the target sequence that was created during the amplification process. A dye capable of engaging in fluorescence energy transfer (FRET) is attached to the triplex TFO probe. In this instance, the dye is the donor dye. The following are two examples of a single stranded DNA that forms a triplex with a double stranded DNA with a TFR:

```
                                          (SEQ ID NO: 36)
5' - GGAGGGGGAGAAGGGAGAAGGG - 3'

(SEQ ID NO: 37)
3' - CCTCCCCCTCTTCCCTCTTCCC - 5'

(SEQ ID NO: 38)
5' - GGTGGGGGTGTTGGGTGTTGGG - 3' TFO (SEQ ID NO: 39)
3'- GGGTTGTGGGTTGTGGGGGTGG - 5' TFO (SEQ ID NO: 40)
5' - GTGTGGGAAGAGGGGGAXGAGGGGGAGGAGC - 3'

(SEQ ID NO: 41)
3' - CACACCCCTTCTCCCTXCTCCCCTCCGTCG - 5'
```

As depicted in FIG. 42, the 3' end of the TFO probe is capped with a phosphate to prevent the TFO probe from participating in the amplification process. The TFO probe may also be capped by a fluorescent dye, a non-extendable linker, or any other suitable atom or molecule known to those of ordinary skill in the art to prevent oligonucleotide extension during amplification reactions. The donor dye may be attached at or proximate to the 3' end of the probe. The donor dye may also be attached at or proximate to the 5' end of the TFO probe. The donor dye may also be attached anywhere between the 5' end and the 3' end of the TFO probe. When a dye is attached to the TFO probe, it comprises a triplex forming fluorescent probe (TFFP).

Figure 43:
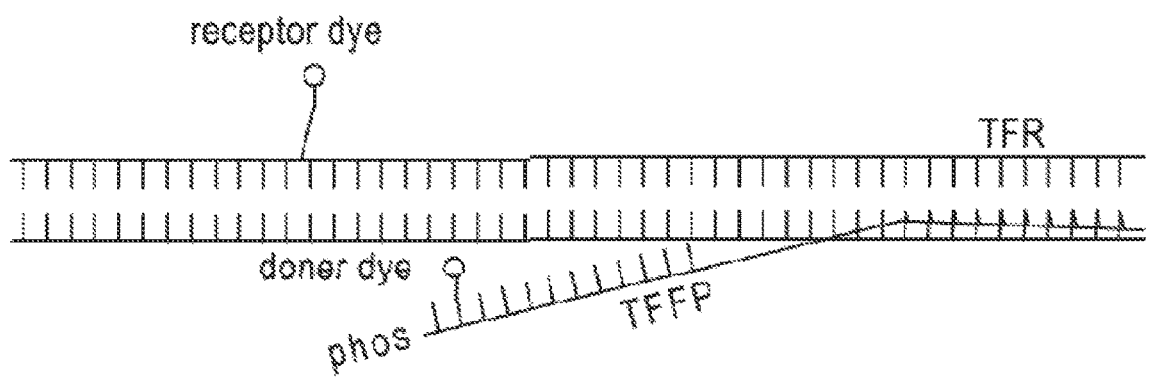
FIG. 43 depicts a double stranded DNA sequence comprising a Triplex Forming Region. The double stranded DNA sequence possesses a receptor dye. The TFR of the TFFP attaches to the Triplex Forming Region of the double stranded DNA.

FIG. 43 depicts a double stranded DNA sequence comprising a Triplex Forming Region. The double stranded DNA sequence possesses a receptor dye. The TFR of the TFFP attaches to the Triplex Forming Region of the double stranded DNA.

In one embodiment, the TFFP anneals to the amplified DNA only when the temperature of the reaction is at or below the annealing temperature of the primers. Thus, the triplex forming fluorescent probe does not participate in the reaction. When the TFFP bonds to the amplified sequence, and a light is shone on the product, the donor dye on the TFFP resonates. As the donor dye resonates, it transfers energy to a receptor dye located on the double stranded DNA, causing the receptor dye to fluoresce at a particular wavelength, emitting light of a color that corresponds to that wavelength. This indicates that the sequence of interest was present in the test sample and has been amplified.

In an alternative embodiment, the receptor dye is attached to the TFFP and the donor dye is attached to the amplified double stranded DNA product. In this embodiment, the acceptor dye fluoresces when the sequence of interest has been amplified.

In another embodiment, a plurality of primers may be used, with each primer designed to bind to and specifically amplify a different sequence of interest. Each primer has a different acceptor dye attached to it such that each acceptor dye fluoresces at a different wavelength. The triplex forming fluorescent probe will bind to the Triplex Forming Region of the amplified product. A donor dye attached to the triplex forming probe will cause the acceptor dye on the amplified product to fluoresce a certain color, depending on which product has been amplified. In this manner, a plurality of different sequences may be tested for at once. This embodiment would allow a plurality of different potential sequences of interest to be tested for in one reaction vessel. Testing for a plurality of different potential sequences of interest in one reaction vessel is known as multiplexing.

In an alternative embodiment of a multiplex probe combination, the acceptor dye may be attached to the TFFP and the donor dye can be attached to the amplified double stranded DNA product. In this embodiment, each primer would have a different colored donor dye, such that the acceptor dye, attached to the TFO probe, will fluoresce at a different color, depending on which primer has amplified the sequence of interest.

In another embodiment, the TFO probe is designed to anneal at approximately the same temperature, or at a slightly higher or lower temperature than the Tm of the primers. This embodiment allows for the reading of amplification results in real time.

Triplex Forming Region Probe Design with Naturally Occurring TFRs

Another embodiment takes advantage of naturally occurring triplex forming regions (TFR) that are located within or adjacent to the sequence of interest itself. The following are examples of naturally occurring TFR sequences in double stranded DNA.

```
5' TTTTTTCCCGTCC 3'                    (SEQ ID NO: 42)

3' AAAAAGGGCAGG 5'                     (SEQ ID NO: 43)

5' GGCGAGGGGGAGCGGG 3'                 (SEQ ID NO: 44)

3' CCGCTCCCCCCTCGCCC 5'                (SEQ ID NO: 45)

5' GGAGGTGGGGGAG 3'                    (SEQ ID NO: 46)

3' CCTCCACCCCCTC 5'                    (SEQ ID NO: 47)

5' GGAGGTGGGGGAG 3'                    (SEQ ID NO: 48)

3' CCTCCACCCCCCTC 5'                   (SEQ ID NO: 49)

5' GGAGAAGGTGAGGAAGAAGAAGAGGAAGAA 3'   (SEQ ID NO: 50)
```

In this embodiment, the primers are designed to bond with the naturally occurring triplex forming regions as well as with the sequence of interest.

In this way, the triplex forming region of the DNA is amplified to detectable levels as the sequence of interest is amplified. The primer has a receptor dye attached to it. The triplex forming probe is created having a sequence complementary to the naturally occurring sequence of interest.

In another embodiment of a method of multiplexing, each set of primers designed to test for a particular sequence of interest comprises its own unique TFR base pair sequence in addition to its own unique color dye. In one embodiment, the dye would be a donor dye. A plurality of TFO probes is then designed, each set of which comprises a TFR to match a particular TFR of one of the amplified products. Each set of probes also comprises its own unique acceptor dye color. Which product is amplified determines which probe will bond with it. Which probe attaches to the amplified product, and hence, which sequence of interest exists in the sample, is determined by the color of the probe's fluorescence when it undergoes FRET with the dye of the TFO probe.

In another embodiment, the detection method may comprise the use of specialty DNA binding dyes that bind preferentially to triplex DNA structures. In one embodiment, the dye comprises Thiazole Orange. In another embodiment, the dye comprises Cyanine 40 dye. In addition to the dyes set forth herein, any other dyes that bind preferentially to triplex DNA structures, known by those of ordinary skill in the art, may be used. These triplex binding dyes may be used in combination with dye labeled TFRs, either on the primers or internal to the product itself, to produce a FRET based signal that could also indicate the presence of specifically formed target sequence(s).

Figure 44:
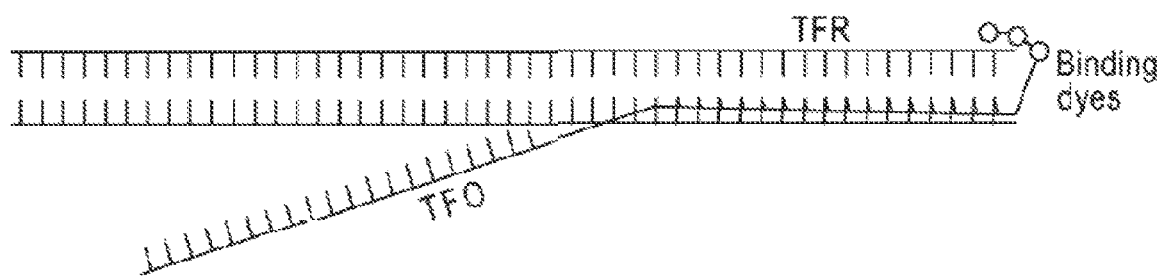
FIG. 44 illustrates that the binding dyes, constrained by covalent attachment to a particular location on the TFO probe, in this instance, the end of the TFO probe, can only bind to hybridized DNA structures when the TFO probe is bound and thus, puts the TFO probe in proximity to the dye attached to the amplified sequence of interest. Thus, a fluorescent signal indicates that amplification has occurred.

An alternative method involves TFO probe coupling to DNA binding dyes. These would include, without limitation: Sybr Green 1; Sybr Gold; Eva Green; LightCycler Green I; LightCycler Green II; Toto/Yoyo/Toyo; and other DNA binding dyes that bind to hybridized DNA structures known to those of ordinary skill in the art. As depicted in FIG. 44, the binding dyes, constrained by covalent attachment to a particular location on the TFO probe, in this instance, the end of the TFO probe, can only bind to hybridized DNA structures when the TFO probe is bound and thus, puts the TFO probe in proximity to the dye attached to the amplified sequence of interest. Thus, a fluorescent signal indicates that amplification has occurred.

In yet another embodiment, Cy2 or other quadruplex binding dyes known to those of ordinary skill in the art may be used.

Figure 45:
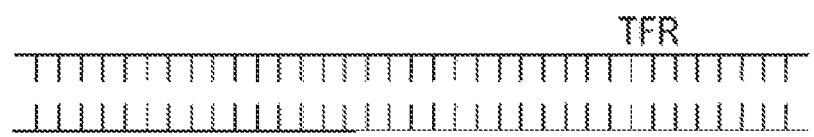
FIG. 45 depicts that in this embodiment the TFO probe utilizes a hairpin dye and quencher configuration.
Figure 45:
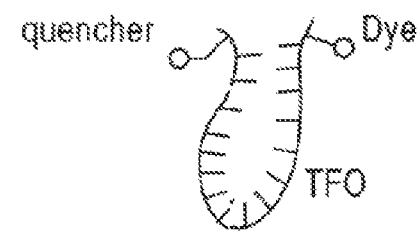
Figure 45:
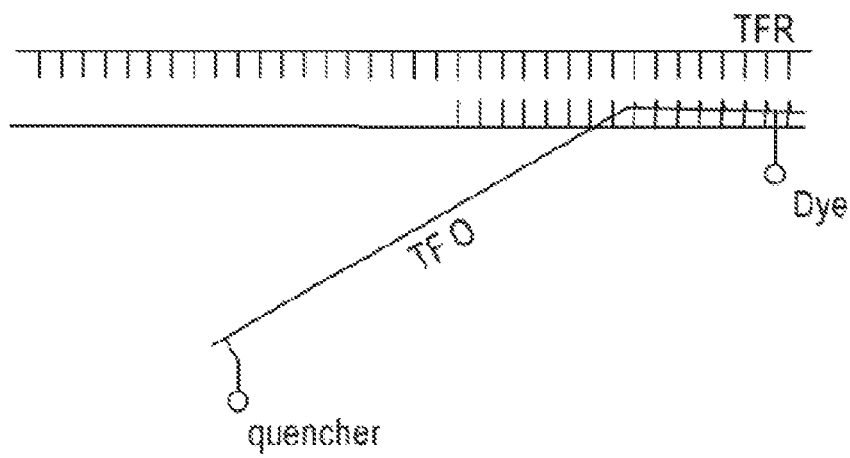

In another embodiment, the TFO probe may be synthesized with a fluorescent dye and quencher located anywhere along its length. As depicted in FIG. 45, this embodiment utilizes a hairpin dye and quencher configuration. Upon the binding of the TFO probe to the sequence of interest, the hairpin structure of the probe is eliminated, with the result that the quencher becomes sufficiently distal from the dye that it is no longer able to suppress the dye's fluorescence. This results in a fluorescence of a certain color being emitted if the sequence of interest has been amplified. The specific fluorescent signal change is irrelevant so long as it is distinguishable from that of any other product in the reaction mix. The total number of reactions that can be detected can be distinguished only depends on the instrument platform that the reactions are being performed on.

Figure 46:
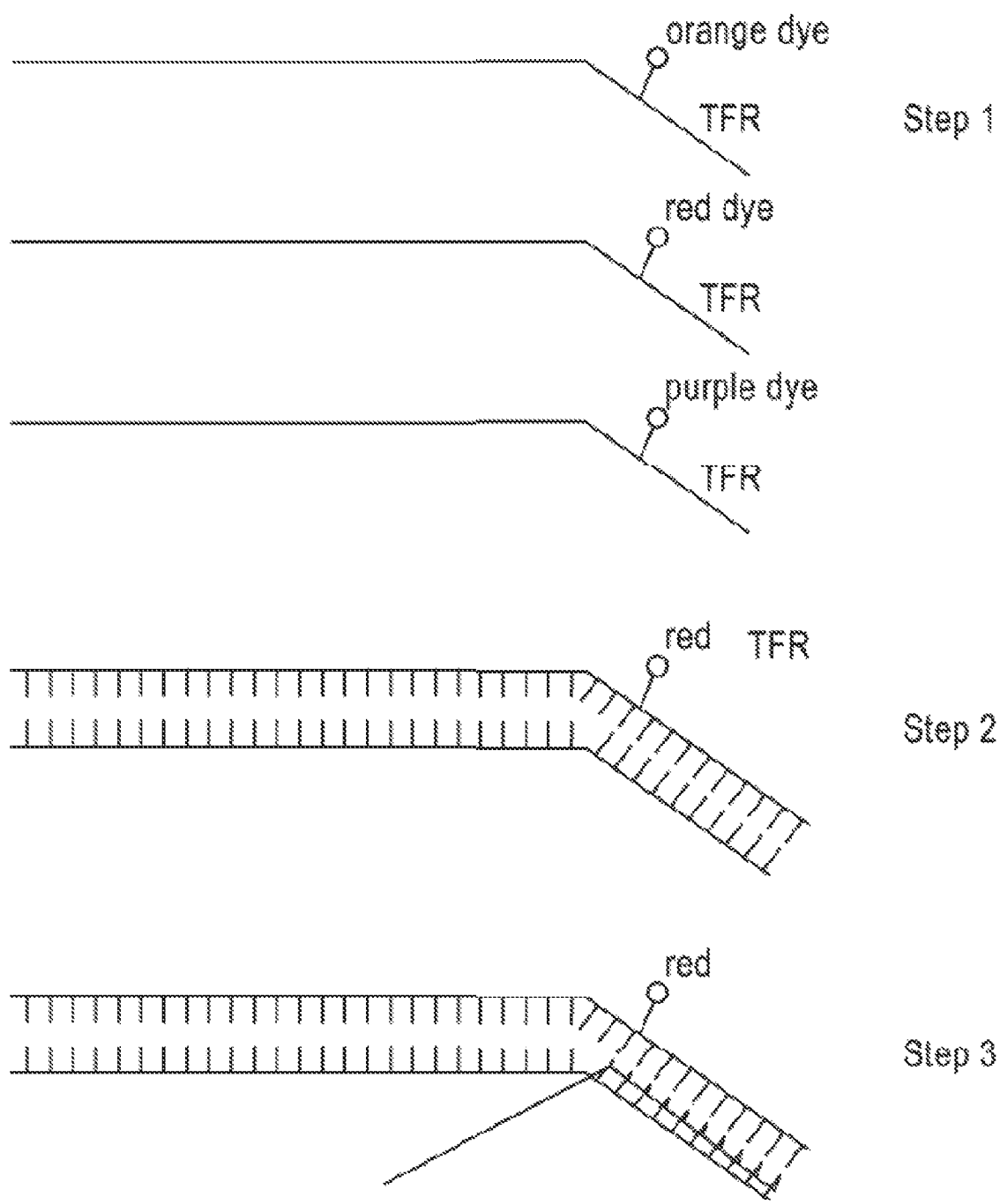
FIG. 46 illustrates that two or more primers with the same TFR sequence may be used along with TFR primers that comprise a sequence complementary to the TFR sequence.

In another embodiment, depicted in FIG. 46, two or more primers with the same TFR sequence may be used along with TFR primers that comprise a sequence complementary to the TFR sequence. FIG. 46 depicts three TFR primers, each with a different color dye. In step 2, the primer comprising the red dye has bound to the sequence of interest and been amplified. In step 3, the TFR probe has bound to the TFR in the presence of a binding dye that binds preferentially to a triplex. Such a binding dye may comprise Thiazole Orange, Cyan 40, or any other triplex binding dye known to those of ordinary skill in the art. The binding dye engages in FRET with the attached fluorophore, indicating that the sequence complementary to the primer comprising the red dye has been amplified.

Figure 47:
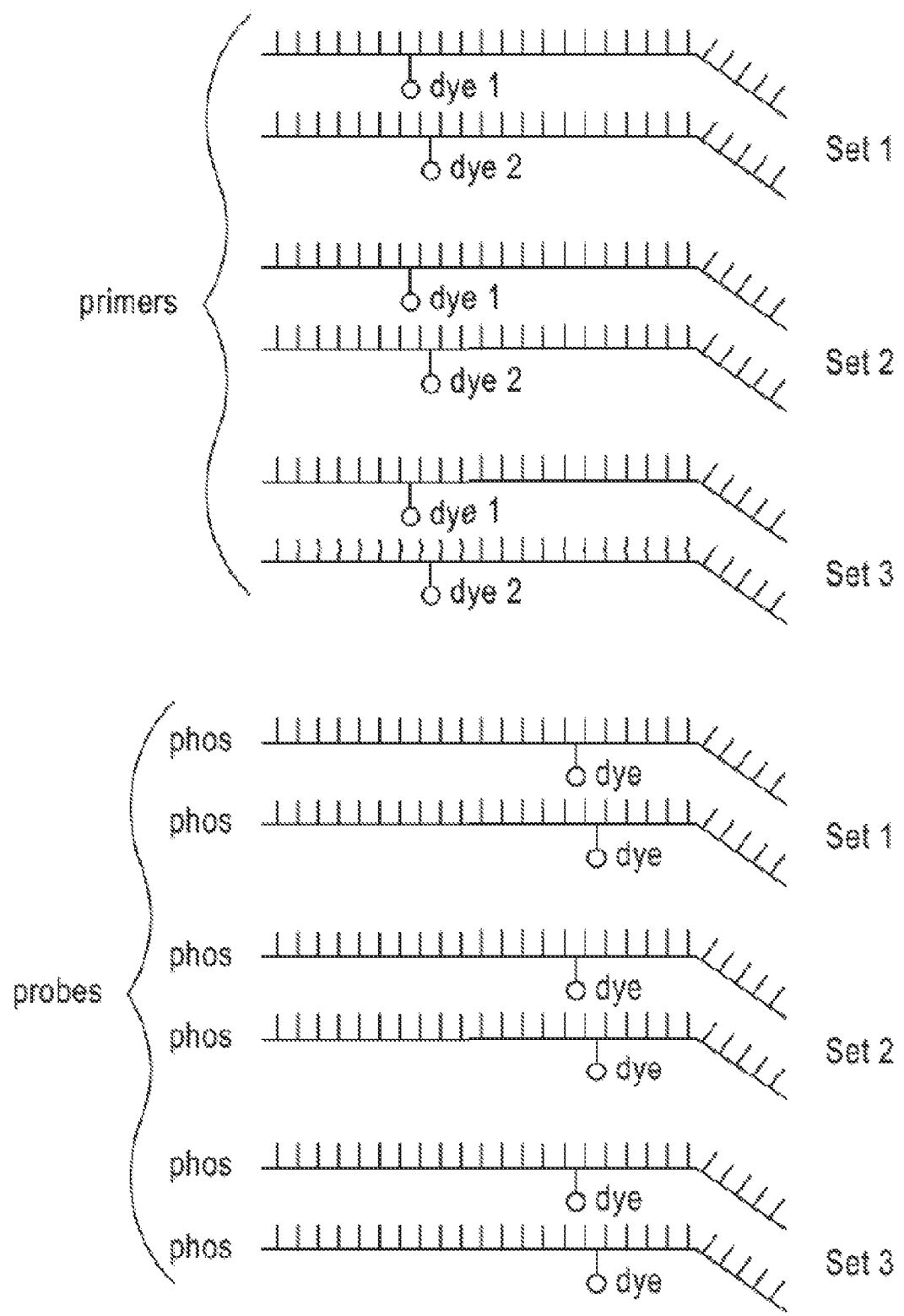
FIG. 47 depicts an embodiment wherein six primers are divided into three sets of two each.

In an alternative embodiment, the products may be distinguished by color, melting temperature, or a combination of both color and melting temperature of the triplex products. FIG. 47 depicts an embodiment wherein six primers are divided into three sets of two each. Each set of two primers comprises the same TFR sequence and the three sets each comprise three different TFR sequences such that each of the three sets of primers are distinguishable from the other two by virtue of having a different melting temperature. The two TFR sharing primers within each set each has a different color dye. The method also comprises using three sets of probes comprising a sequence that binds the TFR of one of the pairs of primers. The products would then be distinguishable based its unique combinations of melting temperature and color. These various methods of distinguishing product would enable the use of Triplex DNA formation in the detection of amplified product as quantitative, genotyping, or simply target detection.

Figure 48:
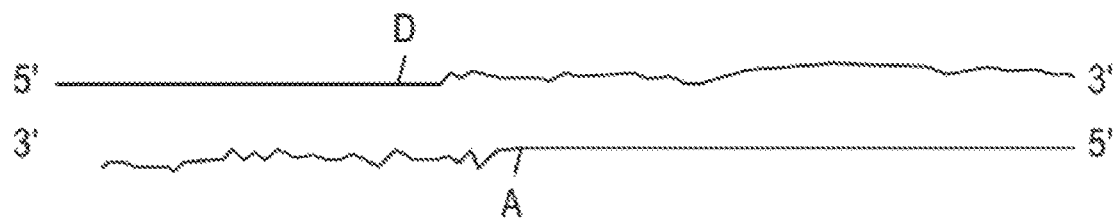
FIG. 48 depicts that the donor dye is attached near the 3' end of the first primer, while the acceptor dye is attached near the 3' end of the second primer. At the annealing step, the primers hybridize to their target sequences in a near tail-to-tail arrangement, which brings the dyes into sufficient proximity for FRET to occur.

The following is an alternative embodiment of primer and probe technology designed to take advantage of the unique characteristics of DFA. In this embodiment, each primer of a pair of primers is labeled with a dye that can engage in fluorescence resonance energy transfer (FRET). As depicted in FIG. 48, the donor dye is attached near the 3' end of the first primer, while the acceptor dye is attached near the 3' end of the second primer. At the annealing step, the primers hybridize to their target sequences in a near tail-to-tail arrangement, which brings the dyes into sufficient proximity for FRET to occur. The amount of acceptor fluorescence is proportional to the amount of DFA product present.

The assay kits of the present disclosure for amplifying and/or detecting a target sequence of a DNA sample can include: i) the primers and probes described herein, and ii) buffer, dNTPs, and enzymes. Such reactants are present in sufficient quantities to conduct a plurality of assays.

Further Triplex Forming Region Probe Designs

Triplex forming oligonucleotides provide a unique method for the detection of amplification products from either PCR, XCR, RAMP, HDA, NEAR, temperature dependent multiplexing or any other amplification technology that results in large quantities of amplified double stranded DNA.

We have described the introduction of artificial TFRs either attached somewhere along the length of a primer. More interesting though, is the natural occurrence of triplex forming regions (TFRs), which is surprisingly abundant. For example, *Streptococcus agalactiae* with a 2 million base pair genome, has as many as 29 TFRs of 16 base pairs or longer. Such relatively high abundance of such TFRs makes it plausible to utilize such TFRs (either homopurine or homopyrimidine stretches) as potential diagnostic markers for the amplification of the desired nucleic acid.

The TFO would bind to the amplified double stranded DNA at any point during the reaction where the complete double stranded extension has occurred through the TFR portion of the product.

Advantageously, such binding events can be monitored at many different stages of the amplification and thus will not, like other hybridization chemistries, obligate the real-time readout to occur at the lowest temperature of the reaction where the unextended single stranded DNA is exposed for probe binding.

One distinct advantage of being able to use higher temperatures for the fluorescent reads is that reactions can be sped up to maximal velocity with the commensurate advantage of not encouraging non-specific product formation by holding for extended times at relatively low reaction temperatures.

Cycling Probe Technology

An alternative method to detect amplification products utilizes Cycling Probe Technology to take advantage of the speed of DFA by providing end point analysis. Cycling Probe Technology, as described in U.S. Pat. No. 5,660,988 (herein incorporated in its entirety for all purposes) is a technology used in the so-called signal amplification method. As described in U.S. Pat. No. 5,660,988, a cycling probe binds to a target and is subsequently cleaved by an enzyme. Once the cycling probe is cleaved, another cycling probe binds to the target and is in turn cleaved. This process can be repeated until all the probes have been used. In the method described herein, the cycling probe is designed to have a Tm lower than the lowest Tm of the thermal cycling profile for the reaction being run. Once the reaction has been run, the temperature of the reaction is lowered to a point that is equal to or lower than the Tm of the cycling probe. In the case of a positive result, the cycling probes then bind and are cleaved in series until a signal is generated. Alternatively, a probe containing a ribonucleotide can function during initial thermal cycling, being cleaved either by an RNAse or by the exonuclease activity of a polymerase.

EXAMPLES

Example 1: Amplification of a Target Sequence Using Primers with Tags

The following primers were created to be used in conjunction with DFA to amplify a target sequence.

```
Salmonella FORw/otag (SEQ ID NO: 12):
CGACGACCCTTCTTTTTCCTCAATACTGAGCGGCTG, Tm 75.8° C.

@ 4 mM Mg and 0.5 µM primer

Salmonella REVw/otag (SEQ ID NO: 13):
CGCTGCCGGTATTTGTTATTTTATCGGTGGTTTTAAGCGTACTCTTCTAT

TTTAAATTCC,

Tm 75.2° C. @ 4 mM Mg and 0.5 µM primer

Salmonella FORw/tag (SEQ ID NO: 14):
CGTCGCGACGACCCTTCTTTTTCCTCAATACTGAGCGGCTG, tag is underlined Salmonella REVw/tag (SEQ ID NO: 15):
CAGCGCGCTGCCGGTATTTGTTATTTTATCGGTGGTTTTAAGCGTACTCT TCTATTTTAAATTCC, tag is underlined Target for first primer binding (SEQ ID NO: 16):
CGACGACCCTTCTTTTTCCTCAATACTGAGCGGCTGCTCGCCTTTGCTGG

TTTTAGGTTTGGCGGCGCTACGTTTTGCTTCACGGAATTTAAAATAGAAG

AGTACGCTTAAAACCACCGATAAAATAACAAATACCGGCAGCG, 86.5° C. @ 4 mM Mg

Annealing temperature for after first extension:
ACCCTTCTTTTTCCTCAATACTGAGCGGCTG (SEQ ID NO: 17), 73.3° C.

CCGGTATTTGTTATTTTATCGGTGGTTTTAAGCGTACTCTTCTATTTTAA

ATTCC (SEQ ID NO: 18), 73.3° C.

Target for second primer binding (SEQ ID NO: 19):
ACCCTTCTTTTTCCTCAATACTGAGCGGCTGCTCGCCTTTGCTGGTTTTA

GGTTTGGCGGCGCTACGTTTTGCTTCACGGAATTTAAAATAGAAGAGTAC
```

-continued

GCTTAAAACCACCGATAAAATAACAAATACCGG, 85.2° C. @ 4 mM Mg

Target for complete primer w/tag binding
(SEQ ID NO: 20):
CGTCGCGACGACCCTTCTTTTTCCTCAATACTGAGCGGCTGCTCGCCTTT

GCTGGTTTTAGGTTTGGCGGCGCTACGTTTTGCTTCACGGAATTTAAAAT

AGAAGAGTACGCTTAAAACCACCGATAAAATAACAAATACCGGCAGCGCG

CTG, 87.8° C. @ 4 mM Mg

Example 2: Amplification of a Target Sequence Using Primers with Tags that Form G-Quadruplexes The following is an example of potential G-quadruplex used in maintaining the DFA amplification bubble, and serving to block extension beyond the bubble.

Mycobacterium avium subsp. paratuberculosis str.
k10, complete genome, Sequence ID: gb|AE016958.1|
(SEQ ID NO: 21):
5'-TCGAATCCCTCTCCCCGCCCGGGCGGTACGACGCGCCGAGGAAGCGG

TGCACCAGGGCGCGCTCGGCGGCCGGGTCCTTGAGCGGCCAGCCCCATAA

CGCCAGGAAGACGCGGATCAGCCACTGCGCCGCCAGCGGGTCGTCGTGGC

CGGGCCCGAGCATCTCGGCGGCCAGGGCCGTCA-3'

(SEQ ID NO: 22):
5'-TACCGCCCGGGCCCGGGCGGTACGACGCGCCGA-3'

(SEQ ID NO: 23):
5'-GGCCGGGCCCGGGCCCGGCCACGACGACCCGCT-3'

Figure 18:
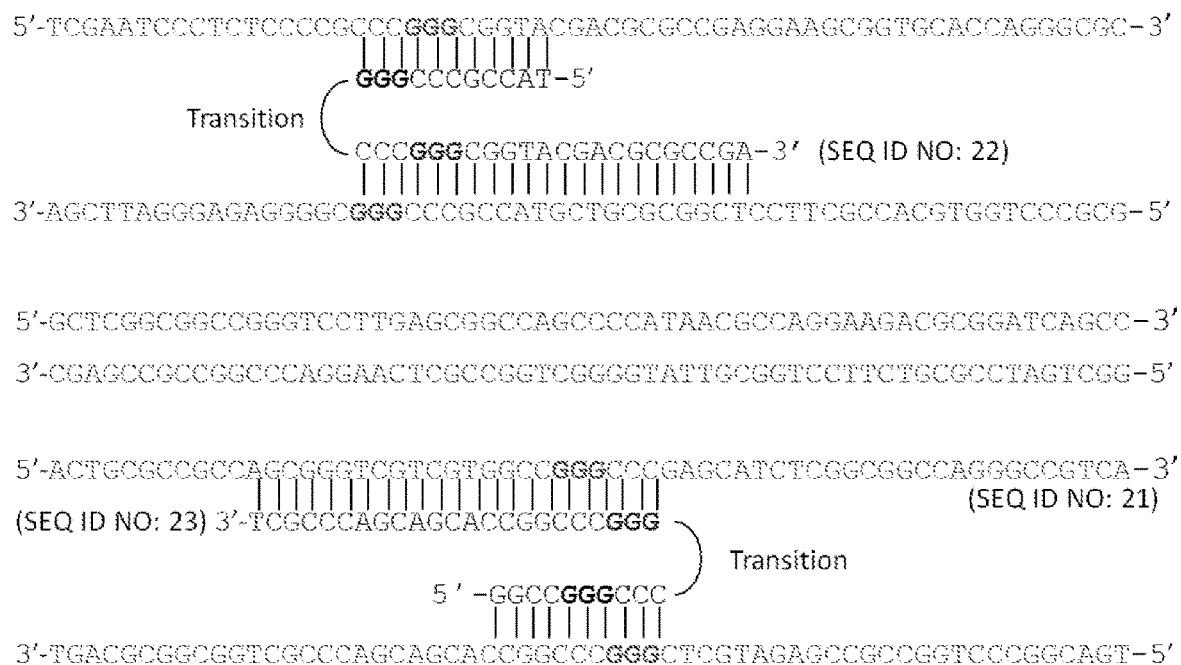
FIG. 18 shows the hybridization of primers (SEQ ID NOs: 22 and 23) to the *Mycobacterium avium* subsp. *paratuberculosis* str. k10 sequence (SEQ ID NO: 21) to form G-quadruplex structures to block extension beyond the bubble.

FIG. 18 shows the hybridization of the above primers to the Mycobacterium avium sequence to form G-quadruplex structures to block extension beyond the bubble.

Figure 25:
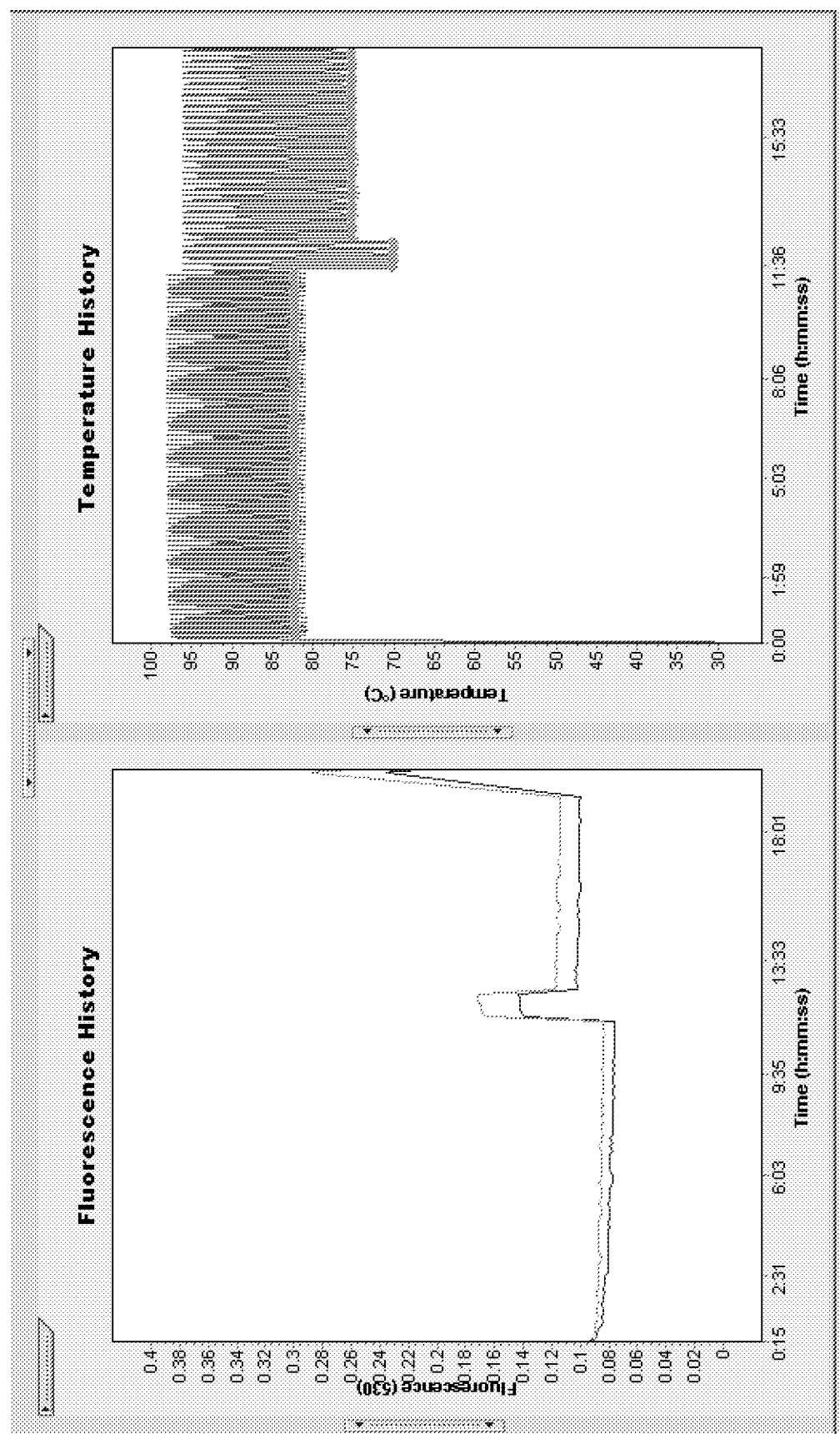
FIG. 25 depicts fluorescence history and temperature history of an amplification described in Example 3.

Example 3: Temperature Dependent Multiplexing of Target and Control Sequences A multi-temperature protocol is followed for development of an internal control for amplification of a Mycobacterial target. In this case, the control amplicon has similar thermal cycling properties to the target amplicon, 94° C. for denaturation and 84° C. for annealing/extension. However, the primers (Mfo1275fmut2, Mfo1490rmut2) have introduced nucleotide mismatches such that the predicted Tm for the target DNA, a Mycobacterium fortuitum sequence (Mfo template), is <80° C. After an initial round of extension that erases the mismatch, however, the predicted Tm returns to 86° C. The initially low affinity of primers for template means that, as shown in FIG. 25, there is no amplification evident for 80 cycles at 94° C.–85° C.—the thermal cycling profile at which the target Mycobacterial species will be amplified. After the target cycling is completed, 80 cycles, the anneal/extend temperature is downshifted for five cycles to 75° C. to enable priming by the control primers, then returned to 77° C. to amplify the internal control species. In this case, $1\times10^7$ to $12\times10^9$ copies of control template are quiescent during the initial 80 cycles, and are then activated and amplified by the second stage of thermal cycling with a Ct of about 40 cycles.

The thermal cycling conditions are: 95° C.–84° C.×80 cycles, 93° C.–72° C.×5 cycles to catch, 93° C.–77° C.×40 cycles.

The input is $1\times10^9$, $1\times10^7$ copies M. fortuitum synthetic template.

Method: introduce mutations that lower initial Tm and return to high Tm after initial extension by polymerase.

Primer Sequences:
Mfo1275fmut2 (SEQ ID NO: 24): CGTGCACACCCG-GCCAAGGTCGTTGCGGCCCAGAG (underlined bases are mismatched to template), Pre catch Tm=80° C. plus effect of 3' mismatch (not predicted by software); post catch Tm=85° C.; wild type Tm=86° C.

Mfo1490rmut2 (SEQ ID NO: 25): ACGGCGTTTTC-GATTGTCGGATCCACCCCGGAGGCCCTGCTCACC (underlined bases are mismatched to template), pre catch Tm=80° C.; post-catch Tm=86° C.; wild type Tm=86° C.

Mfo template (SEQ ID NO: 26): CGTGCACACCCG-GCCGAGGTCGTTGCGGCCGAGATCGACTCG-GTCGCCCCGCGCCA GCGAGTGCCCGCGATCGACG-GTGACCAGGGCCTCCGGGCTGGATCCGACAATCGAA AACGCCGT, Tm=97° C.

Results: control template stays unamplified for 80 cycles, then after temperature shift, the control template amplifies in ~40 cycles.

Figure 26:
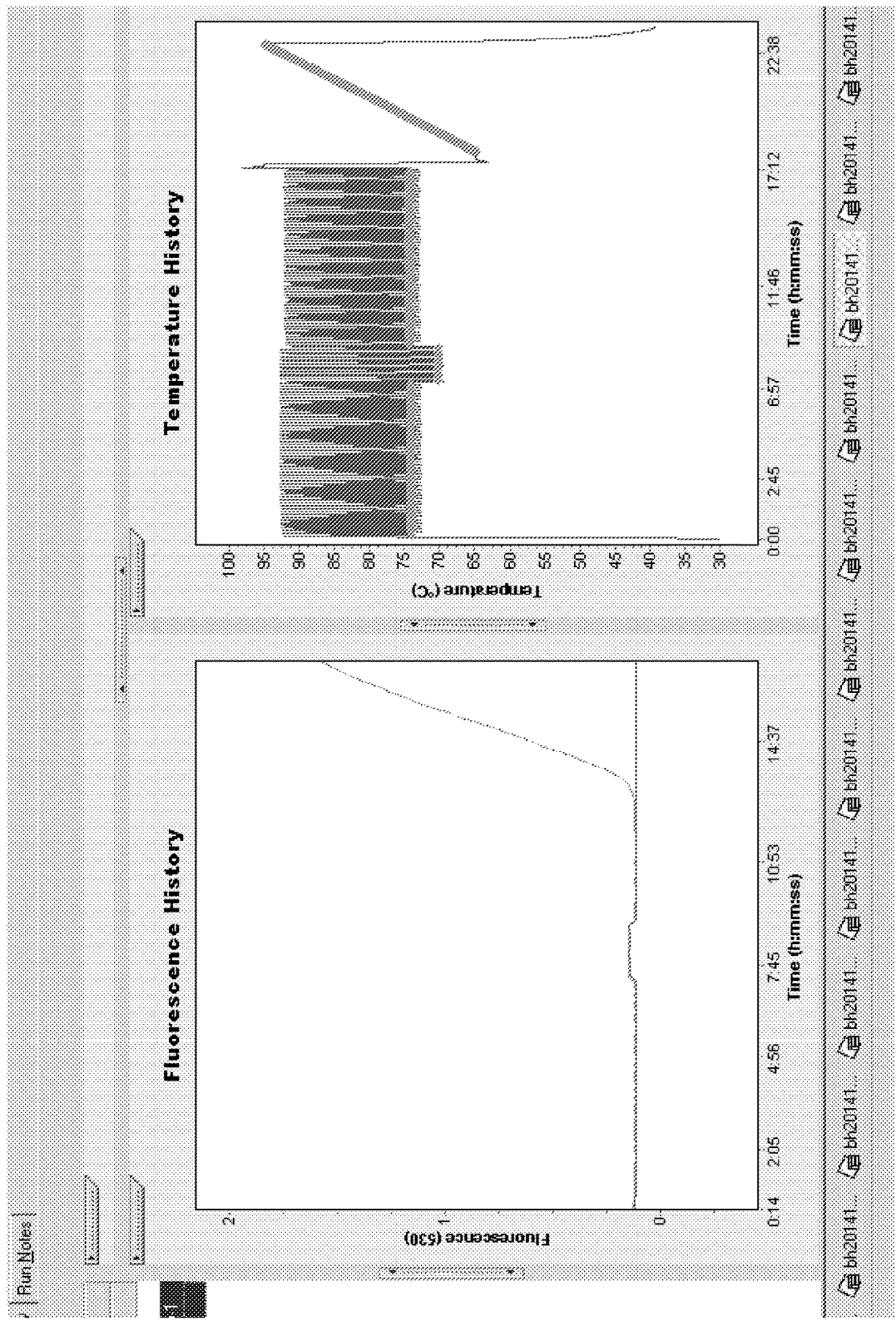
FIG. 26 depicts fluorescence history and temperature history of an amplification described in Example 4.
Figure 27:
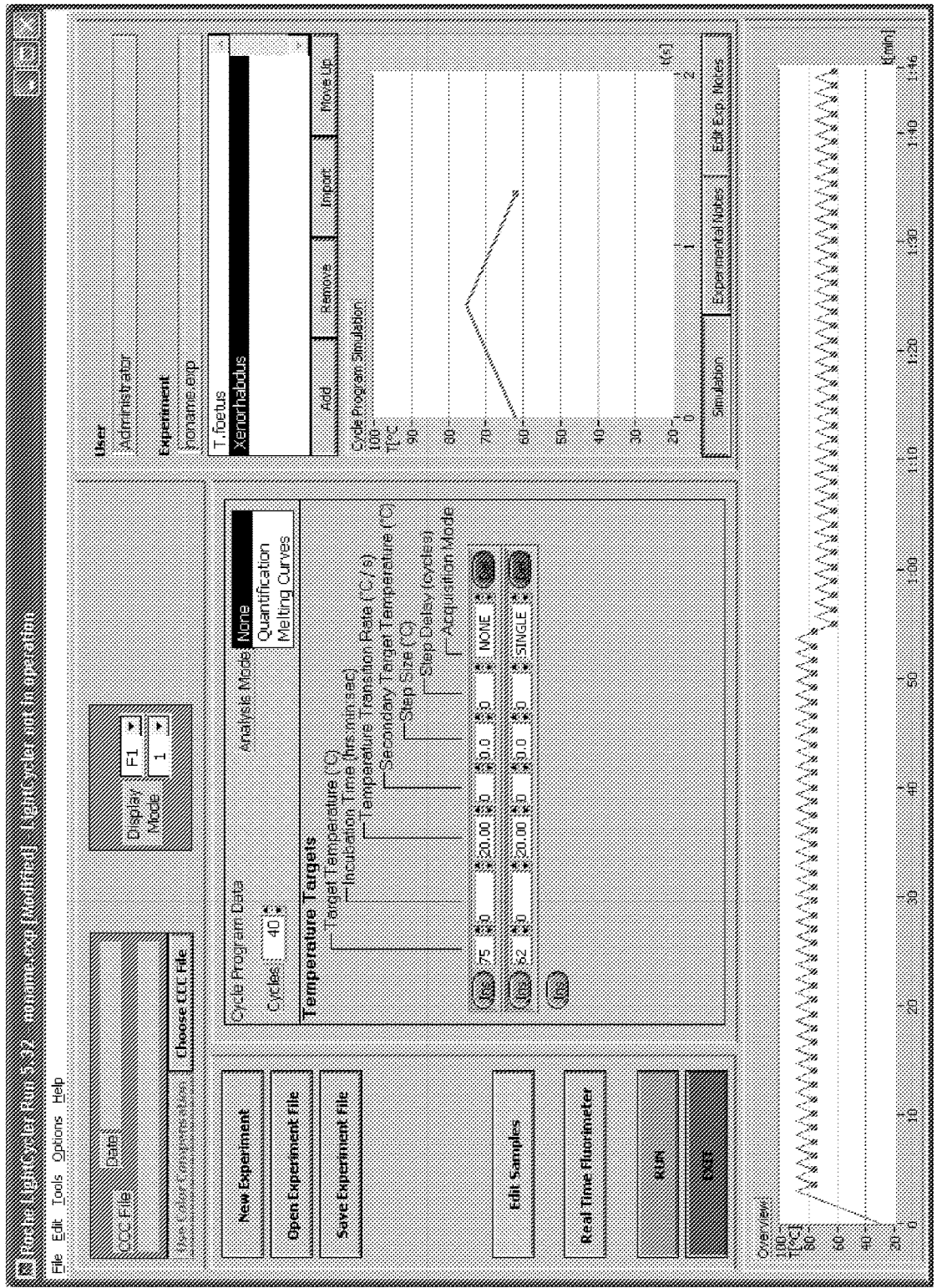
FIG. 27 depicts an exemplary thermal profile for amplification of *Trichomonas foetus* target and reaction control template *Xenorhabdus nematophila*.
Figure 28:
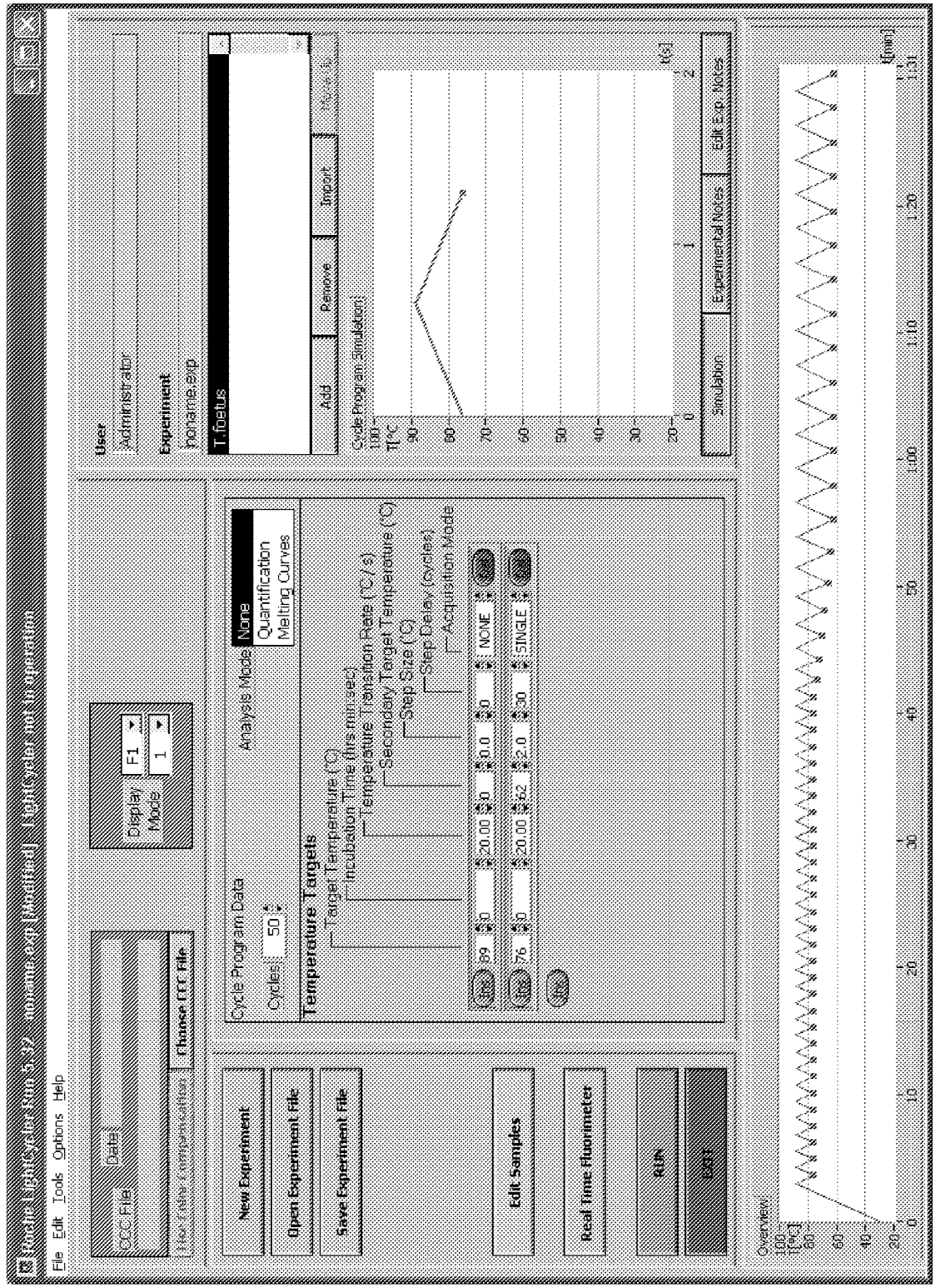
FIG. 28 depicts an exemplary thermal profile for amplification of *Trichomonas foetus* target and reaction control template *Xenorhabdus nematophila*.
Figure 29:
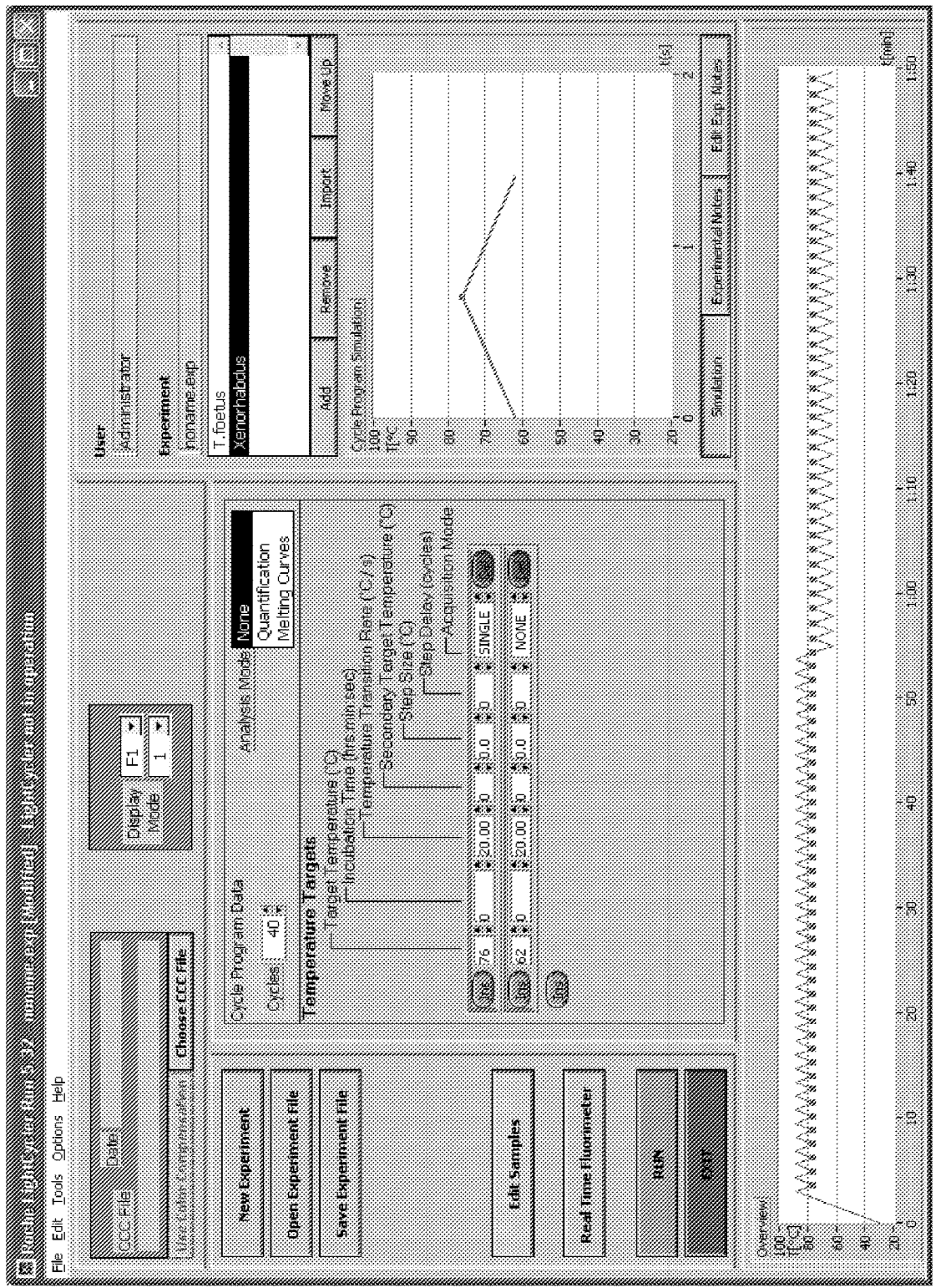
FIG. 29 depicts an exemplary thermal profile for amplification of *Trichomonas foetus* target and reaction control template *Xenorhabdus nematophila*.
Figure 30:
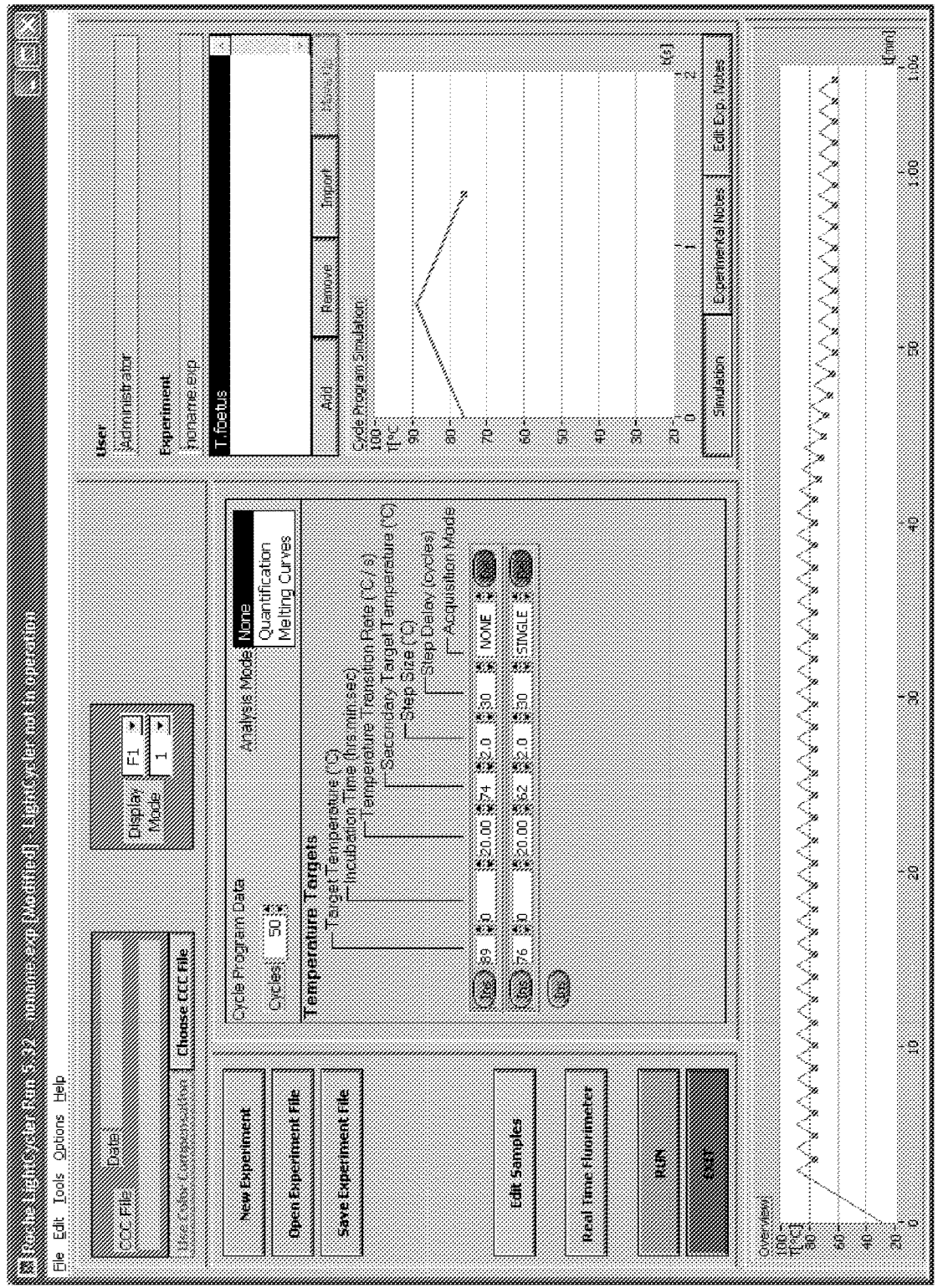
FIG. 30 depicts an exemplary thermal profile for amplification of *Trichomonas foetus* target and reaction control template *Xenorhabdus nematophila*.
Figure 31A:
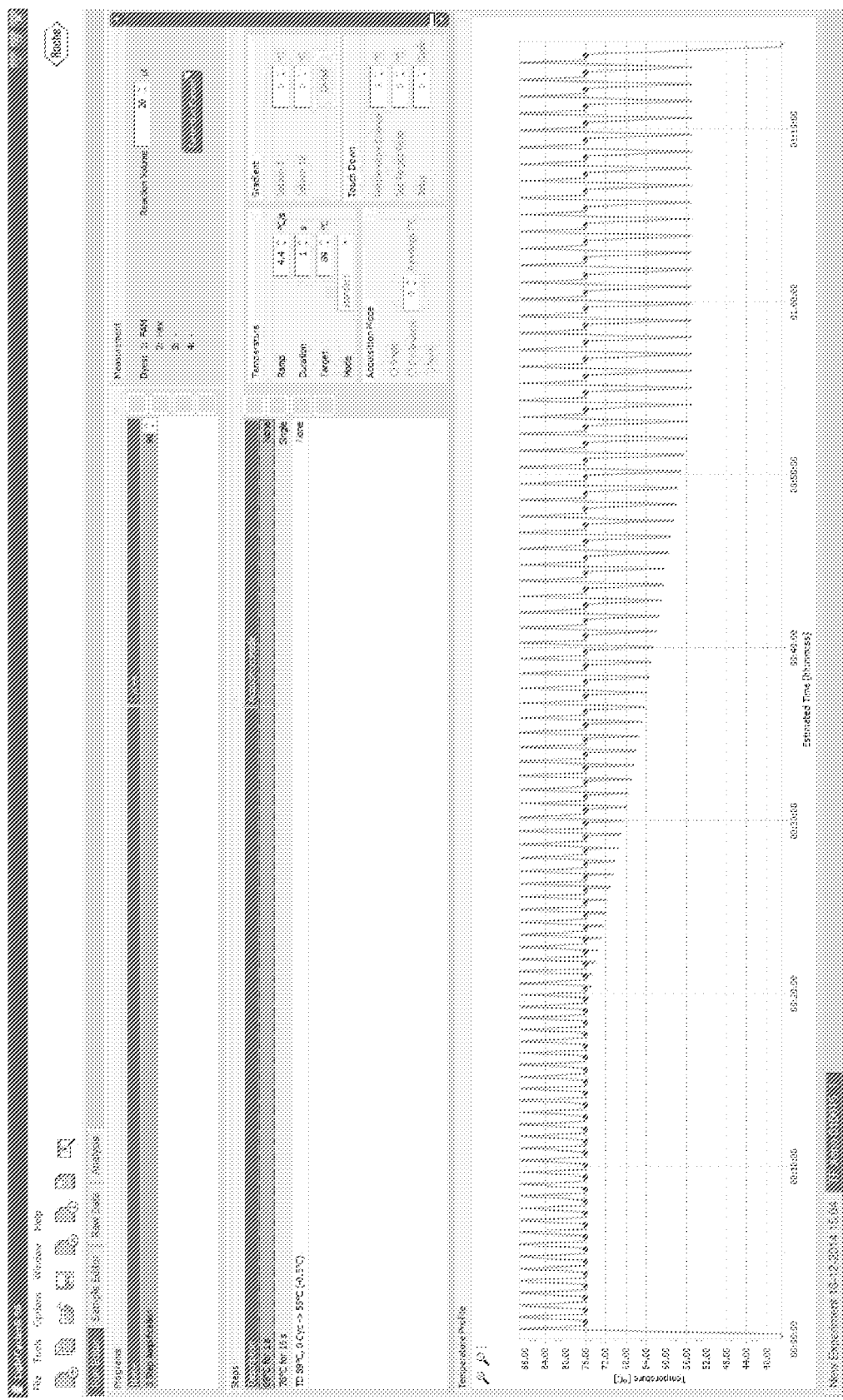
FIG. 31A and FIG. 31B depicts an exemplary thermal profile for amplification of *Trichomonas foetus* target and reaction control template *Xenorhabdus nematophila*.
Figure 31B:
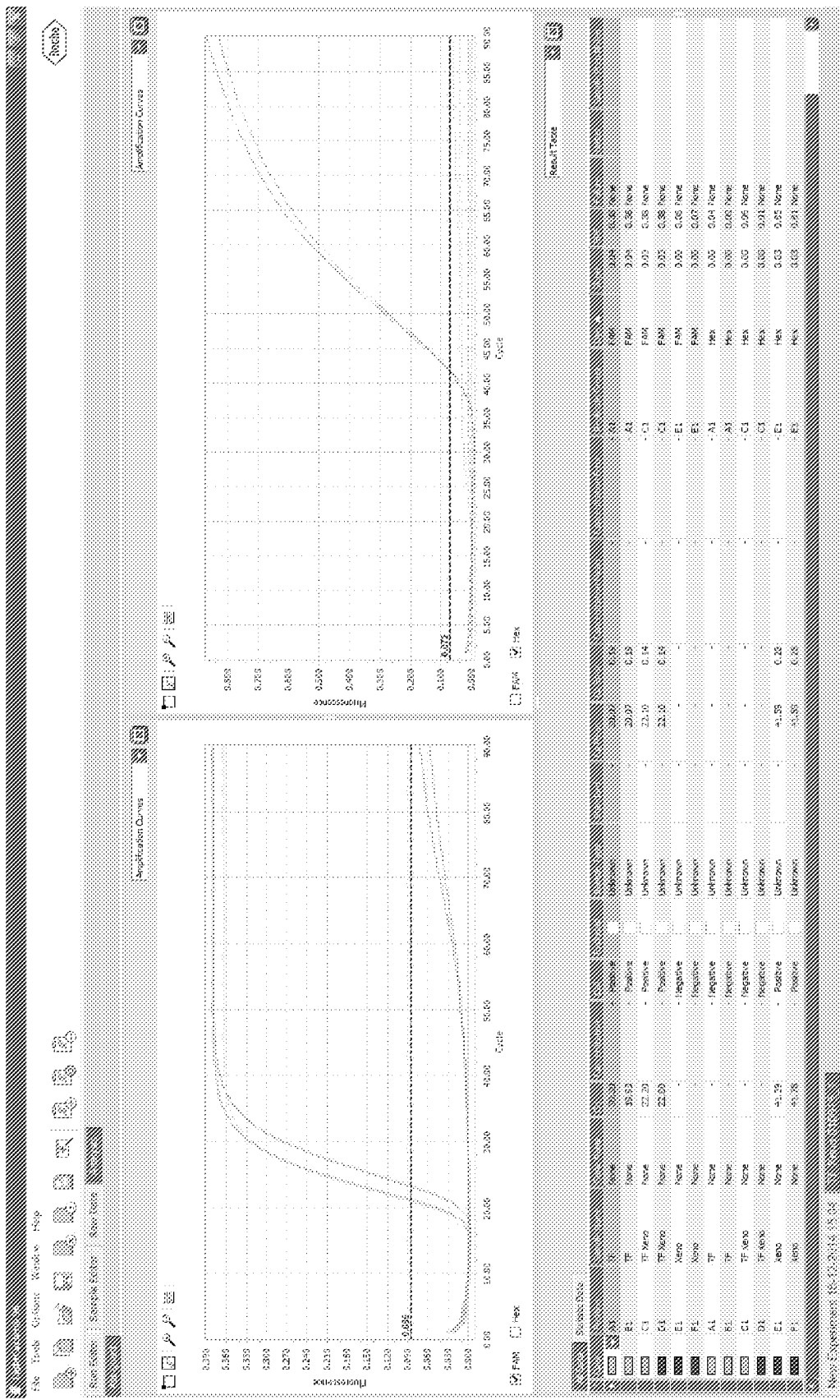

Example 4: Temperature Dependent Multiplexing with Primers Comprising 5' Tails In this example, the internal control primers do not have introduced mismatches to the template, but rather have a lower predicted Tm of 70° C. Each of these primers (SPWX-MF_mut4 and SPWXMR_mut4) bear a 5' GC-rich tail that does not bind to the target sequence, but when extended by the polymerase in the first round of amplification, the Tm becomes 76° C. As in Example 3, these primers do not amplify the template through 50 cycles of 89° C.–76° C. After 50 cycles, the anneal/extend temperature is reduced to 72° C. for 10 cycles then returned to 76° C., after which amplification is seen for the control template (see FIG. 26). The term "catch" refers to the point at which the amplification product begins to achieve full extension.

The thermal cycling conditions are: 89° C.–76° C.×50 cycles, 89° C.–72° C.×10 cycles, 89° C.–76° C.×60 cycles.

The input is Saflager W-34/70 yeast (Spw) genomic DNA diluted 10×.

Method: no mismatched bases, a shortened primer with a 5' tail to increase Tm after catch is made.

Primer sequences:

SPWXMF_mut4 (SEQ ID NO: 27):
<u>CCA GCC</u> ACC CAC CAA TTC CTG TGC CAG AT
(underlined bases are 5' tail), pre-catch
Tm 70° C., post catch is 77° C.

SPWXMR_mut4 (SEQ ID NO: 28):
<u>ACC GGA</u> GGT CAC TTT TGA TGG CCA TGG GTC
TAT (underlined bases are 5' tail), Pre
catch 70° C., post catch 76° C.

Template (SEQ ID NO: 29):
CTC GTT AGA GGG GCT AAA GCT AAC CCA CCA
ATT CCT GTG CCA GAG AAT ATA TAG GGC GGT
GCA TGA ACA ATA GCC GGT AGG TAT GTC AGA
AAA CCT CCA ATG CCA AAC ATT ACT CCT TGA
CAC CGC CTA TAT TTA GAC CCA TGG CCA TCA
AAA GTG ACC CGA GCA CCA TCG TTT GTT G,
Tm = 87° C.

Results: control template stays unamplified for 50 cycles, then after temperature shift, the control template amplifies in ~30 cycles.

Example 5: Temperature Dependent Multiplexing of Target and Control Sequences The following comprises a Duplex example with *Trichomonas foetus* target and reaction control template *Xenorhabdus nematophila*.

A method is described for combining multiple targets in one reaction vessel with each target amplified at discrete stages of the thermal profile. In this Example, the *Trichomonas foetus* represents the desired diagnostic target organism, and the control template *Xenorhabdus nematophila* serves as either the extraction control or as an internal process control. As designed, the *Trichomonas foetus* is amplified in the initial stages of the thermal profile with a higher temperature design, and following a sufficient number of thermal cycles, the reaction transitions to the appropriate conditions to amplify the reaction control target.

```
Xenorhabdus nematophila ATCC 19061 (SEQ ID NO: 30):
TTTATTTTTAGTTATCAATATATCTGAGTTTTATTTTTAGCTACAGTGT

TTTTATTTGTTTTTTAGCAGCCTTACTTAACAGTATTTTGTTAATATCAA

CATATATAAGATATATTATTATTTCTTTACTATGCTCAATAACTCTATCTT

TACATTTAGATATATTACCATCATTTGATTTAATATTTTTCTTGCCTATAT

TTATTTTTGTTTTTATCTATAAATTTAATCTCGTCAAAAAAAGACTATAAT

TATATTGATTAATTTAAGTTTTCAGATGATATAATCAAATTTTATTCCAAT

AATACCAATCATCACTGAAATTGCTTAATTTATACTGAAGATTTGGTTATG

TATTAAATAGTTAATTCTTATCATATACTCCCT

Exemplary forward primer sequence (SEQ ID NO: 31):
TTTTTAGTTATCAATATATCTGAGTTTTATTTTTAGCTACAGTGTTTTTA

TTTGTTTTTTTAGCAGCCTTACTTAACAGTATTTTGTTAATATCAACATAT

ATAAGAT,
Tm = 74° C.

Exemplary forward primer sequence (SEQ ID NO: 51):
TTTTTAGTTATCAATATATCTGAGTTTTATTTTTAGC,
Tm = 62.2° C.

Exemplary reverse primer sequence (SEQ ID NO: 52):
ATCTTATATATGTTGATATTAACAAAATACTGTTAAGT,
Tm = 62.3° C.

Exemplary probe sequence (SEQ ID NO: 53):
CAGTGTTTTTATTTGTTTTTTTAGCAGCCT,
Tm = 65.2° C.

Trichomonas foetus 372 (SEQ ID NO: 54):
CGGTAGGTGAACCTGCCGTTGGATCAGTTTCGTTAATAATTACAAACATAT

TTTTTTAATGTCTATAACTATTTATACAAAATTAAACACATAATCTAAAAA

ATTTAGACCTTAGGCAATGGATGTCTTGGCTTCTTACACGATGAAGAACGT

TGCATAATGCGATAAGCGGCTGGATTAGCTTTCTTTGCGACAAGTTCGATC

TTTGAATGCACATTGCGCGCCGTTTTAGCTTGCTAGAACACGCATATATGT

TACAGTAACCCATATTAATTTAATACCAAATTCTCTTTTTAAGCAAAAGAG

CGAAAAACAAATATGTATTAACAAAAGGGTTCTGTCTCATATAGGAAGACC

CGCTGAACTGAAGCA

Trichomonas foetus 266 (SEQ ID NO: 55):
AGACCTTAGGCAATGGATGTCTTGGCTTCTTACACGATGAAGAACGTTGCA

TAATGCGATAAGCGGCTGGATTAGCTTTCTTTGCGACAAGTTCGATCTTTG

AATGCACATTGCGCGCCGTTTTAGCTTGCTAGAACACGCATATATGTTACA

GTAACCCATATTAATTTAATACCAAATTCTCTTTTTAAGCAAAAGAGCGAA

AAACAAATATGTATTAACAAAAGGGTTCTGTCTCATATAGGAAGACCCGCT

GAACTGAAGCA,
Tm = 85.3° C.

Exemplary forward sequence (SEQ ID NO: 56):
AGACCTTAGGCAATGGATGTCTTGGCTTCTTACACGATGAAGAACG,
Tm = 77.3° C.

Exemplary reverse sequence (SEQ ID NO: 57):
TGCTTCAGTTCAGCGGGTCTTCCTATATGAGACAGAACCCTT,
Tm = 77.3° C.

Exemplary probe sequence (SEQ ID NO: 58):
AAGCGGCTGGATTAGCTTTCTTTGCGACAAGTTCGATCTTTGAATGCACAT TGCGCGCCG,
Tm = 83.1° C.
```

Possible thermal profiles for amplification of *Trichomonas foetus* target and reaction control template *Xenorhabdus nematophila* are depicted in FIGS. 27-31.

Example 6: Temperature Dependent Multiplexing with *Trichomonas* Primers to Detect *Trichomonas* in Cattle The following primers and probes are used in temperature dependent multiplexing to detect *Trichomonas* in cattle.

```
TFXMF (SEQ ID NO: 56):
AGACCTTAGGCAATGGATGTCTTGGCTTCTTACACGATGAAGAACG

TFXMR (SEQ ID NO: 57):
TGCTTCAGTTCAGCGGGTCTTCCTATATGAGACAGAACCCTT

TFXMP2 (SEQ ID NO: 59):
AAGCGGCTGGATTAGCTTTCTTTGCGACAAGTTCGATCTTTGAATGCACA

TTGCGCGCCG
```

The samples for amplification come from Bull tissue. The thermal cycling is from about 89° C. to about 74° C. to amplify the *Trichomonas* target. The thermal cycling is from about 63° C. to about 78° C. to amplify the *Xenorhabdus nematophila* control.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting. Applicants hereby incorporate by reference U.S. application Ser. No. 14/510,939, filed on Oct. 9, 2014, and entitled: Multiplex Probes, in its entirety for all purposes. Further, Applicants hereby incorporate by reference U.S. application Ser. No. 12/951,710, filed on Nov. 22, 2010, and entitled: System and Method for High Resolution Analysis of Nucleic Acids to Detect Sequence Variations, in its entirety for all purposes. Applicants also hereby incorporate by reference U.S. application Ser. No. 12/058,637, filed on Mar. 28, 2008, and entitled: System and Method for High Resolution Analysis of Nucleic Acids to Detect Sequence Variations, which issued as U.S. Pat. No. 7,838,235, on Nov. 23, 2010, in its entirety for all purposes.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A nucleic acid complex, comprising a double-stranded target nucleic acid and a first oligonucleotide primer and a second oligonucleotide primer hybridized thereto,
   wherein the first oligonucleotide primer comprises a 3' end having a sequence substantially complementary to a binding site on the first strand of the target nucleic acid and a 5' end substantially complementary to a binding site on the second strand of the target nucleic acid opposite to the binding she of the 3' end of the first oligonucleotide primer;
   wherein the second oligonucleotide primer comprises a 3' end having a sequence substantially complementary to a binding site on the second strand of the target nucleic acid and a 5' end substantially complementary to a binding site on the first strand of the target nucleic acid opposite to the binding site of the 3' end of the second oligonucleotide primer;
   wherein on the first strand, the binding site of the 3' end of the first oligonucleotide primer is 3' to the binding site of the 5' end of the second oligonucleotide primer; and
   wherein on the second strand, the binding site of the 3' end of the second oligonucleotide primer is 3' to the binding site of the 5' end of the first oligonucleotide primer.

2. The nucleic acid complex of claim 1, wherein each oligonucleotide primer comprises a transition between the 3' end and the 5' end of said oligonucleotide primer.

3. The nucleic acid complex of claim 2, wherein the transition comprises a single nucleotide, a chain of carbons, a multifunctional moiety, modified nucleotides, modified backbones or a combination thereof.

4. The nucleic acid complex of claim 1, wherein the nucleic acid complex comprises a target nucleic acid sequence on the first strand of the target nucleic acid, wherein the target nucleic acid sequence comprises the binding site of the 3' end of the first oligonucleotide primer, the binding site of the 5' end of the second oligonucleotide primer, and the portion of the first strand between said two binding sites; and wherein the Tm of the first oligonucleotide primer and the Tm of the second oligonucleotide primer are within at most 15° C. of the Tm of the target nucleic acid sequence.

5. The nucleic acid complex of claim 1, wherein the Tms of the oligonucleotide primers are within at most 10° C. of the Tm of the target nucleic acid sequence.

6. The nucleic acid complex of claim 1, wherein the Tms of the oligonucleotide primers are within at most 5° C. of the Tm of the target nucleic acid sequence.

7. The nucleic acid complex of claim 1, wherein the Tms of the oligonucleotide primers are within at most 2.5° C. of the Tm of the target nucleic acid sequence.

8. The nucleic acid complex of claim 1, wherein the Tms of the oligonucleotide primers are equal to the Tm of the target nucleic acid sequence.

9. The nucleic acid complex of claim 1, wherein at least one of the 5' ends comprises nucleotide or backbone modifications to optimize annealing of the oligonucleotide primer to the binding site of said 5' end.

10. The nucleic acid complex of claim 1, wherein at least one of the oligonucleotide primers comprises a sequence of cytosine nucleotides adjacent to a first sequence of guanosine nucleotides.

11. The nucleic acid complex of claim 10, wherein the number of nucleotides between the cytosine and guanosine nucleotides is less than 5.

12. The nucleic acid complex of claim 10, wherein the number of nucleotides between the cytosine and guanosine nucleotides is less than 4.

13. The nucleic acid complex of claim 10, wherein the number of nucleotides between the cytosine and guanosine nucleotides is less than 3.

14. The nucleic acid complex of claim 10, wherein the number of nucleotides between the cytosine and guanosine nucleotides is less than 2.

15. The nucleic acid complex of claim 10, wherein the number of nucleotides between the cytosine and guanosine nucleotides is 0.

16. The nucleic acid complex of claim 10, wherein the at least one oligonucleotide primer can form a Guanosine quadruplex structure.

17. The nucleic acid complex of claim 10, wherein the at least one oligonucleotide primer further comprises a second sequence of guanosine nucleotides adjacent to the first sequence of guanosine nucleotides.

18. The nucleic acid complex of claim 17, wherein the second sequence of guanosine nucleotides causes the primer to shift and form a Guanosine quadruplex structure.

19. A method for increasing the melting temperature (Tm) of oligonucleotide primers to be used in a polymerase chain reaction (PCR), comprising:
   (i) selecting a double-stranded target nucleic acid;
   (ii) designing a first oligonucleotide primer comprising a 3' end substantially complementary to a binding site on the first strand of the target nucleic acid and a 5' end substantially complementary to a binding site on the second strand of the target nucleic acid opposite to the binding site of the 3' end of the first oligonucleotide primer;
   (iii) designing a second oligonucleotide primer comprising a 3' end substantially complementary to a binding site on the second strand of the target nucleic acid and a 5' end substantially complementary to a binding site on the first strand of the target nucleic acid opposite to the binding site of the 3' end of the second oligonucleotide primer;
   wherein the first oligonucleotide primer and the second oligonucleotide primer form the nucleic acid complex of claim 1 when incubated with the double-stranded target nucleic acid;
   wherein the double-stranded target nucleic acid contains a target nucleic acid sequence on its first strand that comprises the binding site of the 3' end of the first oligonucleotide primer, the binding site of the 5' end of the second oligonucleotide primer, and the portion of said first strand between said two binding sites; and
   wherein the Tm of the first oligonucleotide primer and the Tm of the second oligonucleotide primer are within at most 15° C. of the Tm of said target nucleic acid sequence; and
   (iv) synthesizing said first and second oligonucleotide primers.

20. The method of claim 19, wherein the Tms of the oligonucleotide primers are within at most 10° C. of the Tm of the target nucleic acid sequence.

21. The method of claim 19, wherein the Tms of the oligonucleotide, primers are within at most 5° C. of the Tm of the target nucleic acid sequence.

22. The method of claim 19, wherein the Tms of the oligonucleotide primers are within at most 2.5° C. of the Tm of the target nucleic acid sequence.

23. The method of claim 19, wherein the Tms of the oligonucleotide primers are equal to the Tm of the target nucleic acid sequence.

24. A method for nucleic acid sequence amplification, comprising:
   (i) generating a solution comprising the nucleic acid complex of claim 1; and
   (ii) amplifying a target nucleic acid sequence in said nucleic acid complex by subjecting the solution to thermal cycling;
   wherein the nucleic acid complex of claim 1 is generated by a process that includes incubating the double-stranded target nucleic acid, the first olignucleotide primer, and the second olignucleotide primer at a temperature selected to minimize non-target nucleic acid sequence denaturation and maximize target nucleic acid sequence denaturation.

* * * * *